US010921312B2

(12) United States Patent
Eisele

(10) Patent No.: US 10,921,312 B2
(45) Date of Patent: *Feb. 16, 2021

(54) GANGLIOSIDES FOR STANDARDIZING AND INCREASING THE SENSITIVITY OF CELLS TO BOTULINUM NEUROTOXINS IN IN VITRO TEST SYSTEMS

(71) Applicant: MERZ PHARMA GMBH & CO. KGAA, Frankfurt am Main (DE)

(72) Inventor: Karl-Heinz Eisele, Frankfurt am Main (DE)

(73) Assignee: MERZ PHARMA GMBH & CO. KGAA, Frankfurt am Main (DE)

(*) Notice: Subject to any disclaimer, the term of this patent is extended or adjusted under 35 U.S.C. 154(b) by 0 days.

This patent is subject to a terminal disclaimer.

(21) Appl. No.: 15/119,553

(22) PCT Filed: Feb. 18, 2015

(86) PCT No.: PCT/EP2015/053403
§ 371 (c)(1),
(2) Date: Aug. 17, 2016

(87) PCT Pub. No.: WO2015/124618
PCT Pub. Date: Aug. 27, 2015

(65) Prior Publication Data
US 2017/0059558 A1 Mar. 2, 2017

(30) Foreign Application Priority Data
Feb. 19, 2014 (EP) ..................................... 14155726

(51) Int. Cl.
*G01N 33/50* (2006.01)
*C12N 5/0793* (2010.01)

(52) U.S. Cl.
CPC ....... *G01N 33/5058* (2013.01); *C12N 5/0619* (2013.01); *C12N 2500/36* (2013.01);
(Continued)

(58) Field of Classification Search
CPC ........... G01N 33/5058; G01N 2333/33; G01N 33/5073; C12N 5/0619; C12N 2501/998;
(Continued)

(56) References Cited

U.S. PATENT DOCUMENTS

2010/0216181 A1 8/2010 Daigh et al.
2010/0279403 A1 11/2010 Rajesh et al.

FOREIGN PATENT DOCUMENTS

WO 2010105234 A1 9/2010
WO 2012135621 A2 10/2012

OTHER PUBLICATIONS

International Search Report in International Application No. PCT/EP2015/053403, dated Apr. 17, 2015.
Altschul et al., "Basic Local Alignment Search Tool," J. Mol. Biol., 1990, 215, pp. 403-410.
Arnon et al., "Botulinum Toxin as a Biological Weapon," JAMA, 2001, vol. 285, No. 8, pp. 1059-1070.
Jason R. Barash and Stephen S. Arnon "A Novel Strain of Clostridium botulinum That Produces Type B and Type H Botulinum Toxins," J. Infect. Dis., 2014, 209, pp. 183-191.
(Continued)

*Primary Examiner* — Gregory S Emch
(74) *Attorney, Agent, or Firm* — J.A. Lindeman & Co., PLLC

(57) ABSTRACT

The present invention pertains to a method for standardizing the sensitivity of induced pluripotent stem cell (iPS)-derived neurons to a neurotoxin polypeptide, comprising the steps of: a) cultivating different batches of induced pluripotent stem cell-derived neurons in a cell culture medium comprising GT1b for at least 3 hours; b) contacting the different batches of induced pluripotent stem cell-derived neurons of step a) with a neurotoxin polypeptide; c) cultivating the different batches of induced pluripotent stem cell-derived neurons of step b) for at least 24 hours in the presence of GT1b under conditions which allow for the neurotoxin polypeptide to exert its biological activity, thereby standardizing the sensitivity of the induced pluripotent stem cell-derived neurons to a neurotoxin polypeptide. The invention further relates to a method for the generation of induced pluripotent stem cell-derived neurons having a standardized sensitivity to a neurotoxin polypeptide, comprising the steps of: a) providing different batches of induced pluripotent stem cell-derived neurons; b) cultivating the different batches of induced pluripotent stem cell-derived neurons of step a) in a cell culture medium comprising GT1b for at least 3 hours, thereby standardizing the sensitivity of the induced pluripotent stem cell-derived neurons to a neurotoxin polypeptide. In addition, encompassed by the present invention is a method for determining the biological activity of a neurotoxin polypeptide, comprising the steps of: a) cultivating induced pluripotent stem cell-derived neurons in a cell culture medium comprising GT1b for at least 3 hours; b) contacting the induced pluripotent stem cell-derived neurons of step a) with a neurotoxin polypeptide; c) cultivating the induced pluripotent stem cell-derived neurons of step b) for at least 24 hours in the presence of GT1b under conditions which allow for the neurotoxin polypeptide to exert its biological activity; and d) determining the biological activity of the neurotoxin polypeptide in said cells. Finally, the invention relates to the use of GT1b for a) standardizing the sensitivity of different batches of induced pluripotent stem cell-derived neurons to a neurotoxin polypeptide; or b) reducing the variability of the sensitivity of different batches of induced pluripotent stem cell-derived neurons to a neurotoxin polypeptide.

10 Claims, 5 Drawing Sheets

Figure 1:
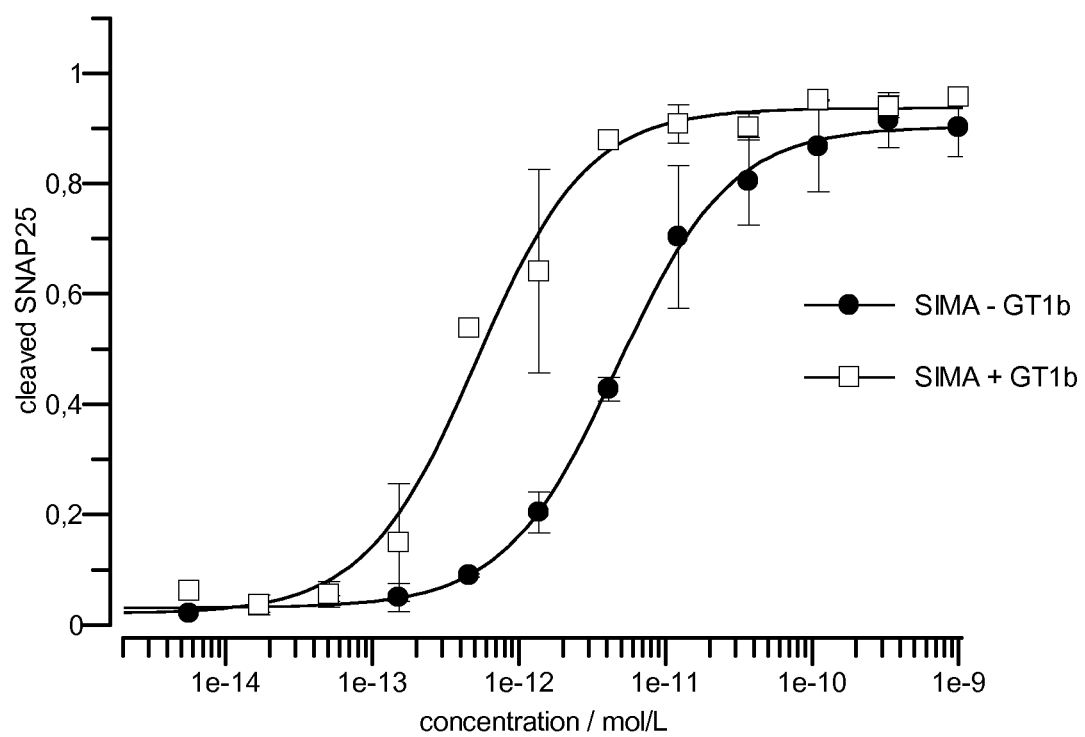

Specification includes a Sequence Listing.

(52) U.S. Cl.
CPC .... *C12N 2501/50* (2013.01); *C12N 2501/998* (2013.01); *C12N 2506/45* (2013.01); *G01N 2333/33* (2013.01)

(58) Field of Classification Search
CPC ............ C12N 2500/36; C12N 2501/50; C12N 2506/45
See application file for complete search history.

(56) References Cited

OTHER PUBLICATIONS

Couesnon et al., "Expression of botulinum neurotoxins A and E, and associated non-toxin genes, during the transition phase and stability at high temperature: analysis by quantitative reverse transcription-PCR," Microbiology, 2006, 152, pp. 759-770.

Dover et al., "Molecular Characterization of a Novel Botulinum Neurotoxin Type H Gene," J. Infect. Dis., 2014, 209, pp. 192-202.

Dressler et al., "Mouse Diaphragm Assay for Detection of Antibodies Against Botulinum Toxin Type B," Movement Disord. vol. 20, No. 12, 2005, pp. 1617-1619.

Fernandez-Salas et al., "Botulinum Neurotoxin Serotype a Specific Cell-Based Potency Assay to Replace the Mouse Bioassay," PLOS One, Nov. 2012, vol. 7, Issue 11, p. e49516.

Audrey Fischer and Mauricio Montal "Single molecule detection of intermediates during botulinum neurotoxin translocation across membranes," PNAS, Jun. 19, 2007, vol. 104, No. 25, pp. 10447-10452.

Desmond G. Higgins and Paul M. Sharp "Fast and sensitive multiple sequence alignments on a microcomputer," CABIOS Commun. vol. 5, No. 2, 1989, pp. 151-153.

Jost et al., "Botulinum Neurotoxin Type A Free of Complexing Proteins (XEOMIN) in Focal Dystonia," Drugs, 2007, 67, (5), pp. 669-683.

J.E. Keller "Recovery from Botulinum Neurotoxin Poisoning in Vivo," Neuroscience, 139, 2006, pp. 629-637.

Krieglstein et al., "Arrangement of disulfide bridges and positions of sulfhydryl groups in tetanus toxin," Eur. J. Biochem., 188, 1990, pp. 39-45.

Krieglstein et al., "Limited proteolysis of tetanus toxin," Eur. J. Biochem., 202, 1991, pp. 41-51.

Krieglstein et al., "Covalent Structure of Botulinum Neurotoxin Type A: Location of Sulfhydryl Groups, and Disulfide Bridges and Identification of C-Termini of Light and Heavy Chains," J. Protein Chem., vol. 13, No. 1, 1994, pp. 49-57.

Saul B. Needleman and Christian D. Wunsch "A General Method Applicable to the Search for Similarities in the Amino Acid Sequence of Two Proteins," J. Mol. Biol., 1970, 48, pp. 443-453.

Pearce et al., "Measurement of Botulinum Toxin Activity: Evaluation of the Lethality Assay," Toxicol. Appl. Pharmacol., 128, 1994, pp. 69-77.

Pellett et al., "Comparison of the primary rat spinal cord cell (RSC) assay and the mouse bioassay for botulinum ieurotoxin type a potency determination," J. Pharmacol. Toxicol. Methods, 61, 2010, pp. 304-310.

Pellett et al., "Sensitive and quantitative detection of botulinum neurotoxin in neurons derived from mouse embryonic stem cells," NIH public Access, Author Manuscript; Biochem. Biophys. Res. Commun., 2011, 404(1); pp. 388-392.

Sabine Pellett "Progress in Cell Based Assays for Botulinum Neurotoxin Detection," NIH Public Access, Author Manuscript; Cuff. Top. Microbiol. Immunol., 2013, 364, pp. 257-285.

Stephen Silberstein "Botulinum Neurotoxins: Origins and Basic Mechanisms of Action," Pain Practice, vol. 4, Issue 1S, 2004, pp. S19-S26.

Temple F. Smith and Michael S. Waterman "Comparison of Biosequences," Adv. Appl. Math 2, 1981, pp. 482-489.

Donald W. Straughan "Progress in Applying the Three Rs to the Potency Testing of Botulinum Toxin Type A," ATLA, 34, 2006, pp. 305-313.

Whitemarsh et al., "Novel Application of Human Neurons Derived from Induced Pluripotent Stem Cells for Highly Sensitive Botulinum Neurotoxin Detection," Toxicol. Sci., 126(2), 2012, pp. 426-435.

Yowler et al., "Botulinum Neurotoxin A Activity Is Dependent upon the Presence of Specific Gangliosides in Neuroblastoma Cells Expressing Synaptotagmin I," J. Biolog. Chem., 2002, vol. 277, No. 38, pp. 32815-32819.

Whitemarsh et al., "Model for Studying Clostridium Botulinum Neurotoxin Using Differentiated Motor Neuron-Like NG108-15 Cells", Biochem. Biophys. Res. Commun. 2012, 427(2), pp. 426-430.

GANGLIOSIDES FOR STANDARDIZING AND INCREASING THE SENSITIVITY OF CELLS TO BOTULINUM NEUROTOXINS IN IN VITRO TEST SYSTEMS

The present invention pertains to a method for standardizing the sensitivity of induced pluripotent stem cell (iPS)-derived neurons to a neurotoxin polypeptide, comprising the steps of: a) cultivating different batches of induced pluripotent stem cell-derived neurons in a cell culture medium comprising GT1b for at least 3 hours; b) contacting the different batches of induced pluripotent stem cell-derived neurons of step a) with a neurotoxin polypeptide; c) cultivating the different batches of induced pluripotent stem cell-derived neurons of step b) for at least 24 hours in the presence of GT1b under conditions which allow for the neurotoxin polypeptide to exert its biological activity, thereby standardizing the sensitivity of the induced pluripotent stem cell-derived neurons to a neurotoxin polypeptide. The invention further relates to a method for the generation of induced pluripotent stem cell-derived neurons having a standardized sensitivity to a neurotoxin polypeptide, comprising the steps of: a) providing different batches of induced pluripotent stem cell-derived neurons; b) cultivating the different batches of induced pluripotent stem cell-derived neurons of step a) in a cell culture medium comprising GT1b for at least 3 hours, thereby standardizing the sensitivity of the induced pluripotent stem cell-derived neurons to a neurotoxin polypeptide. In addition, encompassed by the present invention is a method for determining the biological activity of a neurotoxin polypeptide, comprising the steps of: a) cultivating induced pluripotent stem cell-derived neurons in a cell culture medium comprising GT1b for at least 3 hours; b) contacting the induced pluripotent stem cell-derived neurons of step a) with a neurotoxin polypeptide; c) cultivating the induced pluripotent stem cell-derived neurons of step b) for at least 24 hours in the presence of GT1b under conditions which allow for the neurotoxin polypeptide to exert its biological activity; and d) determining the biological activity of the neurotoxin polypeptide in said cells. Finally, the invention relates to the use of GT1b for a) standardizing the sensitivity of different batches of induced pluripotent stem cell-derived neurons to a neurotoxin polypeptide; or b) reducing the variability of the sensitivity of different batches of induced pluripotent stem cell-derived neurons to a neurotoxin polypeptide.

*Clostridium botulinum* and *Clostridium tetani* produce highly potent neurotoxins, i.e. Botulinum toxins (BoNTs) and Tetanus toxin (TeNT), respectively. These Clostridial neurotoxins (CNTs) specifically bind to neuronal cells and disrupt neurotransmitter release. Each toxin is synthesized as an inactive unprocessed approximately 150 kDa single-chain protein. The posttranslational processing involves formation of disulfide bridges, and limited proteolysis (nicking) by the bacterial protease(s). Active neurotoxin consists of two chains, an N-terminal light chain of approx. 50 kDa and a heavy chain of approx. 100 kDa linked by a disulfide bond. CNTs structurally and functionally consist of three domains, i.e. the catalytic light chain, the heavy chain encompassing the translocation domain (N-terminal half) and the receptor binding domain (C-terminal half); see, e.g., Krieglstein 1990, Eur. J. Biochem. 188, 39; Krieglstein 1991, Eur. J. Biochem. 202, 41; Krieglstein 1994, J. Protein Chem. 13, 49. The Botulinum neurotoxins are synthesized as molecular complexes comprising the 150 kDa neurotoxin protein and associated non-toxic proteins. The complex sizes differ based on the Clostridial strain and the distinct neurotoxin serotypes ranging from 300 kDa, over 500 kDa, and 900 kDa. The non-toxic proteins in these complexes stabilize the neurotoxin and protect it against degradation; see Silberstein 2004, Pain Practice 4, S19-S26.

*Clostridium botulinum* secretes seven antigenically distinct serotypes designated A to G of the Botulinum neurotoxin (BoNT). All serotypes together with the related Tetanus neurotoxin (TeNT) secreted by *Clostridium tetani*, are $Zn^{2+}$-endoproteases that block synaptic exocytosis by cleaving SNARE proteins; see Couesnon, 2006, Microbiology, 152, 759. CNTs cause the flaccid muscular paralysis seen in botulism and tetanus; see Fischer 2007, PNAS 104, 10447.

Despite its toxic effects, the Botulinum toxin complex has been used as a therapeutic agent in a large number of diseases. Botulinum toxin serotype A was approved for human use in the United States in 1989 for the treatment of strabism, blepharospasm, and other disorders. It is commercially available as Botulinum toxin A (BoNT/A) protein preparation, for example, under the trade name BOTOX (Allergan, Inc.) or under the trade name DYSPORT/RELOXIN (Ipsen, Ltd). An improved, complex-free Botulinum toxin A preparation is commercially available under the trade name XEOMIN (Merz Pharmaceuticals, LLC). For therapeutic applications, the preparation is injected directly into the muscle to be treated. At physiological pH, the toxin is released from the protein complex and the desired pharmacological effect takes place. The effect of Botulinum toxin is only temporary, which is the reason why repeated administration of Botulinum toxin may be required to maintain a therapeutic effect.

The Clostridial neurotoxins weaken voluntary muscle strength and are effective therapy for strabism, focal dystonia, including cervical dystonia, and benign essential blepharospasm. They have been further shown to relief hemifacial spasm, and focal spasticity, and moreover, to be effective in a wide range of other indications, such as gastrointestinal disorders, hyperhidrosis, and cosmetic wrinkle correction; see Jost 2007, Drugs 67, 669.

During the manufacturing process of Clostridial neurotoxins, the qualitative and quantitative determination of said neurotoxins as well as the quality control of the biologically active neurotoxin polypeptides is of particular importance. In addition, governmental agencies accept only robust, accurate, precise, reliable, and validated Botulinum toxin potency assays. At present the mouse $LD_{50}$ bioassay, a lethality test, remains the "gold standard" used by pharmaceutical manufacturers to analyze the potency of their preparations; see Arnon et al. (2001), JAMA 285, 1059-1070. However, in recent years, considerable effort has been undertaken to seek for alternative approaches to alleviate the need for animal testing and all the disadvantages, costs and ethical concerns associated with this type of animal-based assays. In addition, the regulatory agencies are engaging pharmaceutical companies to apply the three "Rs" principle to the potency testing of Botulinum neurotoxins: "Reduce, Refine, Replace"; see Straughan, Altern. Lab. Anim. (2006), 34, 305-313. As a consequence, cell-based test systems have been developed in order to provide reasonable alternatives to methods using live animals. Yet, only three cellular test systems are available for the determination of neurotoxin biological activity thus far which have been shown to be sufficiently sensitive to neurotoxin polypeptides. These cell-based test systems include the use of primary neurons isolated from rodent embryos which are differentiated in vitro (Pellett et al. (2011), Biochem. Biophys. Res. Commun. 404, 388-392), neuronal differentiated induced pluripotent stem cells (Whitemarsh et al. (2012), Toxicol. Sci. 126, 426-35), and a clone derived from the SiMa cell line (WO 2010/105234 A1).

However, the isolation of primary neurons requires the killing of animals and is laborious, time consuming and validation of these assays appears to be a challenge. Further, test systems using different primary neurons show large variances. Similarly, the generation of neuronally differentiated induced pluripotent stem cells is difficult and time consuming. In addition, storage of such cells is very problematic. Assays using tumor cell lines are frequently not sensitive enough to BoNT. Moreover, complex differentiation protocols are required for said tumor cell lines which result in large variances and/or high failure rates of assays using said cell lines.

In light of the above, further test systems for the determination of neurotoxin polypeptide activity are highly desirable.

Thus, the technical problem underlying the present invention may be seen as the provision of means and methods complying with the aforementioned needs. The technical problem is solved by the embodiments characterized in the claims and herein below.

In a first aspect, the present invention pertains to a method for the generation of induced pluripotent stem cell (IPS)-derived neurons having a standardized sensitivity to a neurotoxin polypeptide, comprising the steps of:
  a) providing different batches of induced pluripotent stem cell-derived neurons;
  b) cultivating the different batches of induced pluripotent stem cell-derived neurons of step a) in a cell culture medium comprising GT1b for at least 3 hours,
thereby standardizing the sensitivity of the induced pluripotent stem cell-derived neurons to a neurotoxin polypeptide.

In this aspect, different batches of induced pluripotent stem cell-derived neurons are provided, in a first step. The batches can differ, e.g., in the number of passages and/or the number of freeze/thaw cycles and/or in other properties mentioned elsewhere herein. Subsequently, the different batches of induced pluripotent stem cell-derived neurons are cultivated in an appropriate cell culture medium comprising GT1b for at least 3 hours, at least 4 hours, at least 5 hours, at least 6 hours, at least 12 hours, at least 24 hours (1 day), at least 36 hours, at least 48 hours (2 days), at least 72 hours (3 days), at least 4 days, at least 5 days or even longer. Preferably, said cultivation is for a few hours, e.g., for 3 hours, 4 hours, 5 hours, 6 hours or 12 hours. As an appropriate cell culture medium, for example, Neurobasal® Medium comprising B-27® Supplement, iCell® neuron medium (Cellular Dynamics international; CDI) or other cell culture media provided by manufacturer's or providers of induced pluripotent stem cell-derived neurons can be used. It has been found by the present inventors, that, thereby, the variability of the sensitivity of the different batches of induced pluripotent stem cell-derived neurons to a neurotoxin polypeptide can be reduced significantly, in comparison to control batches of induced pluripotent stem cell-derived neurons without GT1b treatment, as set forth in more detail below.

In another aspect, the above-indicated method of the invention further comprises
  c) contacting the different batches of induced pluripotent stem cell-derived neurons of step b) with a neurotoxin polypeptide; and
  d) cultivating the different batches of induced pluripotent stem cell-derived neurons of step c) for at least 24 hours, in the presence of GT1b under conditions which allow for the neurotoxin polypeptide to exert its biological activity.

After cultivating the different batches of induced pluripotent stem cell-derived neurons in a cell culture medium comprising GT1b for at least 3 hours, the different batches of induced pluripotent stem cell-derived neurons can first be contacted and then intoxicated with a neurotoxin polypeptide for at least 24 hours (1 day), at least 36 hours, at least 48 hours (2 days), at least 60 hours, at least 72 hours (3 days), at least 4 days, at least 5 days, at least 6 days, at least 7 days (1 week), at least 2 weeks, at least 3 weeks, at least 4 weeks, at least 5 weeks, at least 6 weeks or even longer, in a next step. Preferably, intoxication is for at least 72 hours or longer. The neurotoxin polypeptide can be, for example, BoNT/A, BoNT/B, BoNT/C1, BoNT/D, BoNT/E, BoNT/F, BoNT/G, BoNT/H or TeNT, or a subtype thereof, as defined in more detail elsewhere herein. The different batches of induced pluripotent stem cell-derived neurons are cultivated for the above-indicated time period in the presence of GT1b under conditions which allow for the neurotoxin polypeptide to exert its biological activity. Appropriate cell culture conditions which allow the neurotoxin polypeptide to exert its biological activity and the biological activity of a neurotoxin polypeptide is as defined elsewhere herein. By this treatment, the variability of the sensitivity of the different batches of induced pluripotent stem cell-derived neurons to said neurotoxin polypeptide can be reduced further, in comparison to control batches of intoxicated induced pluripotent stem cell-derived neurons without GT1b treatment.

In a further aspect, the present invention relates to a method for standardizing the sensitivity of induced pluripotent stem cell (iPS)-derived neurons to a neurotoxin polypeptide, comprising the steps of:
  a) cultivating different batches of induced pluripotent stem cell-derived neurons in a cell culture medium comprising GT1b for at least 3 hours;
  b) contacting the different batches of induced pluripotent stem cell-derived neurons of step a) with a neurotoxin polypeptide;
  c) cultivating the different batches of induced pluripotent stem cell-derived neurons of step b) for at least 24 hours in the presence of GT1b under conditions which allow for the neurotoxin polypeptide to exert its biological activity;
thereby standardizing the sensitivity of the induced pluripotent stem cell-derived neurons to a neurotoxin polypeptide.

In a further aspect, the aforementioned methods of the invention can comprise one or more additional steps. For example, said additional steps can encompass steps for determining the biological activity of a neurotoxin polypeptide as defined herein. To this end, the induced pluripotent stem cell (iPS)-derived neurons which have been cultivated in the presence of GT1b as described herein are brought in contact with a neurotoxin polypeptide as defined herein. The term "contacting" as used in accordance with the in methods of the invention refers to bringing the aforementioned cells and the neurotoxin polypeptide which may be comprised, e.g., in a sample, in physical proximity as to allow physical and/or chemical and/or biological interaction. Suitable conditions which allow for specific interaction are well known to the skilled worker. Said conditions will depend on the cells and neurotoxins to be applied in the methods of the present invention and can be adapted by the skilled artisan without further ado. Moreover, a time being sufficient to allow interaction can also be determined by the skilled worker without further ado. For example, a specific amount of an isolated or recombinant neurotoxin polypeptide or a variant thereof as defined herein or a sample comprising a neurotoxin polypeptide can be added to the GT1b-treated induced pluripotent stem cell (iPS)-derived neurons. Thereafter, the cells are incubated with the neurotoxin polypeptide for at least 24 hours under conditions which allow for the neurotoxin polypeptide to exert its biological activity, again in the presence of GT1b. "Conditions which allow for the neurotoxin polypeptide to exert its biological activity" as used herein are known in the art. Subsequently, the exertion of the biological activity is stopped, for example by the addition of a lysis buffer to the cells, and the biological activity of the neurotoxin polypeptide is determined, for instance, by a Western blot assay specifically detecting the cleaved neurotoxin substrate or a specific ELISA technique. For instance, SNAP-25 is a known substrate of and cleaved by BoNT/A, BoNT/C1 and BoNT/E. VAMP/Synaptobrevin is a substrate of and cleaved by BoNT/B, BoNT/D, BoNT/F, BoNT/G and TeNT, whereas Syntaxin is a substrate of and cleaved by BoNT/C1.

Clostridial neurotoxins are characterized in that they specifically inhibit the secretion of neurotransmitters from pre-synaptic nerve endings. The selectivity for peripheral neurons is mediated by the recognition of two different receptors, SV2 and GT1b. The physiological effect of the neurotoxins is based on the cleavage of a protein of the so-called SNARE complex subsequent to the binding of the receptor and the translocation of the neurotoxin's light chain. The determination of the biological activity of BoNT is an important aspect in the characterization of said neurotoxin proteins and is required, inter alia, by regulatory authorities for the commercial release of BoNT-containing products. A reliable test for the measurement of the biological activity of BoNT is, therefore, basis for research, development and marketing of products containing BoNT. Furthermore, cell-based test systems shall replace the thus far predominant animal tests for ethical reasons. For establishing such cell-based test systems, a sufficient high sensitivity of neuronal cells or cell lines towards Botulinum neurotoxins is essential.

To determine the biological activity of Botulinum toxins in pharmaceutical products, the neuronal cells or cell lines shall have the following properties: First, the cells should be of human, neuronal origin in order to resemble the target as close as possible, i.e. the human patient. Second, the cell system shall be robust towards excipients in the final product and, preferably, also towards impurities in intermediate stages of the production process (process controls). Third, the cell-based test system shall exhibit a dynamic measuring range which allows for the accurate determination of the biological activity of BoNT in a vial (for example, 50 $LD_{50}$U BoNT/A). Considering technical factors such as the solubility of excipients, volumes of cell culture media etc., a BoNT concentration of less than 1 pM has to be determined accurately.

One of the available cell-based test systems having sufficiently high sensitivity to BoNT uses neuronal differentiated induced pluripotent stem cells. The present inventors have evaluated a test system using commercially available human induced pluripotent stem cell-derived neurons (Cellular Dynamics International, Inc., Madison). Said human induced pluripotent stem cell-derived neurons had been obtained as cryopreserved cells and were thawed and cultivated for 4 days according to the manufacturer's manual. Said cells are finally differentiated to neuronal cells characterized in that they do not proliferate any more and exhibit a terminally differentiated, neuronal phenotype which cannot be altered any more. After having formed said phenotype, the cells were incubated with neurotoxin polypeptide for 72 hours. Thereafter, the neurotoxin substrate cleavage product was quantified by Immuno-Western blot analysis of the cell lysates or ELISA methods, as exemplified for the neurotoxin polypeptide BoNT/A, and its substrate SNAP-25. As a result of the evaluation of said test, high sensitivity, reproducibility and intermediate precision of said test system could be confirmed, as long as the test had been carried out by using the same cell batch of the mentioned provider. However, when using different cell batches of said provider, unexplainable high variability with respect to the sensitivity of said cells towards neurotoxin polypeptide was found although the characterization of said cell batches by the provider with regard to cell number, viability, phenotype etc. did not give any clue as regards the mentioned variability. Specifically, the sensitivity (EC50) of different cell batches of the human induced pluripotent stem cell-derived neurons of the provider varied in a range from 1.7 to more than 10 U/ml.

It has surprisingly been found by the present inventors that the external application of gangliosides such as GT1b resulted in a drastic reduction of the variability of the sensitivity between different cell batches of the human induced pluripotent stem cell-derived neurons. This finding is unusual for the following reasons: Firstly, cells exhibiting a neuronal phenotype produce endogenously sufficient GT1b themselves. This has been found, for example, for primary neurons. Moreover, even different preparations of primary neuron cell cultures did not show such variability in the sensitivity towards neurotoxin polypeptides, in the inventors' experience. In addition, such effects could not be observed in neuroblastoma cell line-based tests in which, for example, SiMa cells have been used, neither for different passage numbers nor when testing different cryopreserved batches. Secondly, the provider's manual by Cellular Dynamics International did not contain any information with respect to such variability of the sensitivity of different cell batches of the human induced pluripotent stem cell-derived neurons towards neurotoxin polypeptides. When using the methods of the present invention, said variability could advantageously be reduced by the present inventors from about 30% to about 15% (standard deviation) by cultivating and neurotoxin incubation in the presence of 30 μM GT1b which has been added to the cell culture medium. Accordingly, the methods of the present invention provide for a sensitive, accurate and reproducible cell-based test system in order to determine the biological activity of neurotoxins. Said methods can be used as an alternative to conventional animal-based test systems. Further, the comparatively simple methods of the invention for standardizing the sensitivity of human induced pluripotent stem cell-derived neurons to a neurotoxin polypeptide result in an improved sensitivity of said cells: Whereas an EC50 of about 5 U/ml corresponding to 167 fM has been found for cells without addition of GT1b, an EC50 of about 0.75 U/ml corresponding to 25 fM has been found for cells to which GT1b has been added to the cell culture medium, corresponding to a ~7-fold increase of sensitivity. Accordingly, it has been found by the present inventors that the sensitivity of human induced pluripotent stem cell-derived neurons to a neurotoxin polypeptide can be increased by the addition of GT1b, in comparison to human induced pluripotent stem cell-derived neurons cultivated in the absence of GT1b. Specifically, the sensitivity of each single batch of human induced pluripotent stem cell-derived neurons could be improved by the incubation with said ganglioside. Interestingly, the sensitivity of parental SiMa cells to a neurotoxin polypeptide could also be enhanced by the addition of GT1b. In this case, it was possible to increase the sensitivity of said neuroblastoma cells by a factor of 10, in comparison to SiMa cells not treated with GT1b. These results were not a trivial task or self-evident finding because other neuroblastoma cells such as Neuro2a did not exhibit a comparable increase in sensitivity to the neurotoxin polypeptide upon incubation with GT1b, or only a slight increase, such as SH-SY5Y (DSMZ and ECACC), PC12, or NG108-15 cells, as demonstrated in the following examples.

Accordingly, in another aspect, the present invention pertains to a method for the generation of induced pluripotent stem cell (IPS)-derived neurons or SiMa cells having an increased sensitivity to a neurotoxin polypeptide, comprising the steps of:
 a) providing induced pluripotent stem cell-derived neurons or SiMa cells;
 b) cultivating the induced pluripotent stem cell-derived neurons or SiMa cells of step a) in a cell culture medium comprising GT1b for at least 3 hours,
thereby increasing the sensitivity of the induced pluripotent stem cell-derived neurons or SiMa cells to said neurotoxin polypeptide. In a further aspect, SH-SY5Y cells, PC12 cells, or NG108-15 cells having an increased sensitivity to a neurotoxin polypeptide can be produced, by this method.

In still another aspect, the above-indicated method of the invention further comprises
 c) contacting the induced pluripotent stem cell-derived neurons or SiMa cells of step b) with a neurotoxin polypeptide; and
 d) cultivating the induced pluripotent stem cell-derived neurons or SiMa cells for at least 24 hours, in the presence of GT1b under conditions which allow for the neurotoxin polypeptide to exert its biological activity.
Alternatively, SH-SY5Y cells, PC12 cells, or NG108-15 cells can be used in this aspect, of the method of the invention, as indicated above.

In a further aspect, the present invention relates to a method for determining the biological activity of a neurotoxin polypeptide, comprising the steps of:
 a) cultivating induced pluripotent stem cell-derived neurons or SiMa cells, in a cell culture medium comprising GT1b for at least 3 hours;
 b) contacting the induced pluripotent stem cell-derived neurons or SiMa cells of step a) with a neurotoxin polypeptide;
 c) cultivating the induced pluripotent stem cell-derived neurons or SiMa cells of step b) for at least 24 hours in the presence of GT1b under conditions which allow for the neurotoxin polypeptide to exert its biological activity; and
 d) determining the biological activity of the neurotoxin polypeptide in said cells. SH-SY5Y cells, PC12 cells, or NG108-15 cells can alternatively be used for determining the biological activity of a neurotoxin polypeptide, in other aspects of this method of the invention.

Preferably, single batches of said induced pluripotent stem cell-derived neurons, SiMa cells, SH-SY5Y cells, PC12 cells, or NG108-15 cells are used in the methods of the invention for generating induced pluripotent stem cell-derived neurons, SiMa cells, SH-SY5Y cells, PC12 cells, or NG108-15 cells, having an increased sensitivity to a neurotoxin polypeptide, or in the methods of the invention for increasing the sensitivity of the HI mentioned cells of the invention. It is preferred that the SiMa cells are parental SiMa cells (DSMZ no. ACC164). Preferably, the concentration of GT1b is between 10 and 50 µM, more preferably 30 µM. Cultivating the induced pluripotent stem cell-derived neurons, SiMa cells, SH-SY5Y cells, PC12 cells, or NG108-15 cells in a cell culture medium comprising GT1b is preferably for at least 12 hours, at least 24 hours, at least 36 hours, at least 48 hours, at least 60 hours, at least 72 hours or at least 96 hours, or even longer. Intoxication with the neurotoxin polypeptide is preferably carried out for at least 36 hours, 48 hours, 60 hours, 72 hours, 96 hours or even longer. Preferably, the neurotoxin polypeptide is BoNT/A. The increase of the sensitivity to a neurotoxin polypeptide of GT1b-treated induced pluripotent stem cell-derived neurons is preferably at least 2-fold, at least 3-fold, at least 4-fold, at least 5-fold, at least 6-fold, or at least 6.7-fold, in comparison to induced pluripotent stem cell-derived neurons not treated with GT1b. Further, the increase of the sensitivity to a neurotoxin polypeptide of GT1b-treated SiMa cells is preferably at least 2-fold, at least 3-fold, at least 4-fold, at least 5-fold, at least 6-fold, at least 7-fold, at least 8-fold, at least 9-fold, or at least 10-fold, in comparison to SiMa not treated with GT1b. The increase of the sensitivity to a neurotoxin polypeptide of GT1b-treated SH-SY5Y cells is preferably at least 1.2-fold, at least 1.4-fold, at least 1.6-fold, at least 1.8-fold, or at least 2-fold, in comparison to SH-SY5Y cells not treated with GT1b. The increase of the sensitivity to a neurotoxin polypeptide of GT1b-treated PC12 cells is preferably at least 1.1-fold, at least 1.2-fold, at least 1.3-fold, or at least 1.4-fold, in comparison to PC12 cells not treated with GT1b. Moreover, the increase of the sensitivity to a neurotoxin polypeptide of GT1b-treated NG108-15 cells is preferably at least 1.1-fold, at least 1.2-fold, at least 1.3-fold, at least 1.4-fold, at least 1.5-fold, or at least 1.6-fold, in comparison to NG108-15 cells not treated with GT1b.

The methods of the present invention allow for high dilutions of neurotoxin containing samples to be analyzed. Further, the methods of the invention are robust towards excipients and impurities in the samples to be analyzed which allows for high dilutions of said samples. Such high dilutions of samples are important with respect to excipients and impurities within the samples in order to apply said potentially disturbing substances in a concentration as low as possible.

"Induced pluripotent stem cell (iPS)-derived neuron(s)" as used herein means in a broad sense, a cell which is susceptible to a neurotoxin polypeptide exhibiting the biological properties characteristic for a neurotoxin polypeptide, namely, (a) receptor binding, (b) internalization, (c) translocation across the endosomal membrane into the cytosol, and/or (d) endoproteolytic cleavage of proteins involved in synaptic vesicle membrane fusion. Accordingly, an "induced pluripotent stem cell (iPS)-derived neuron" as referred to herein is susceptible to neurotoxin intoxication. More specifically, "susceptible to neurotoxin intoxication" as denoted herein means a cell that can undergo the overall cellular mechanisms whereby a neurotoxin polypeptide (e.g., BoNT/A) cleaves a neurotoxin substrate (e.g., the BoNT/A substrate SNAP-25) and encompasses the binding of the neurotoxin to its corresponding receptor (e.g. binding of BoNT/A to BoNT/A receptor), the internalization of the neurotoxin/receptor complex, the translocation of the neurotoxin light chain from an intracellular vesicle into the cytoplasm and the proteolytic cleavage of the neurotoxin substrate. Assays for determining the biological activity of a neurotoxin polypeptide are well known in the art and also described elsewhere herein (see, e.g., Pellett et al., Withemarsh et al., loc. cit.) As appreciated by those skilled in the art, the neurotoxin-sensitive cell is preferably able to first uptake a neurotoxin and then undergoes the overall cellular mechanisms listed above. A neurotoxin-sensitive cell as used herein can uptake, e.g., about 100 nanomolar (nM), about 10 nM, about 1 nM, about 500 picomolar (pM), about 400 pM, about 300 pM, about 200 pM, about 100 pM, about 90 pM, about 80 pM, about 70 pM, about 60 pM, about 50 pM, about 40 pM, about 30 pM, about 20 pM, about 10 pM, about 9 pM, about 8 pM, about 7 pM, about 6 pM, about 5 pM, about 4 pM, about 3 pM, about 2 pM, about 1 pM, about 0.5 pM, about 0.1 pM, about 50 fM, about 40 fM, about 30 fM, about 20 fM, about 10 fM, about 5 fM, about 4 fM, about 3 fM, about 2 fM, or about 1 fM of neurotoxin polypeptide, or even less than one of the indicated values. EC50 values above 100 pM have been reported in the literature. By definition, a cell susceptible to neurotoxin intoxication must express, or be engineered to express, at least one neurotoxin receptor and at least one neurotoxin substrate. Receptors and substrates for neurotoxins are described in the art. Accordingly, said cell is preferably susceptible to a biologically active or mature neurotoxin polypeptide as defined herein. Preferably, the neurotoxin-sensitive cell as used herein is susceptible to neurotoxin intoxication by, e.g., about 1 nM or less, 500 pM or less, about 400 pM or less, about 300 pM or less, about 200 pM or less, about 100 pM or less, about 90 pM or less, about 80 pM or less, about 70 pM or less, about 60 pM or less, about 50 pM or less, about 40 pM or less, about 30 pM or less, about 20 pM or less, about 10 pM or less, about 9 pM or less, about 8 pM or less, about 7 pM or less, about 6 pM or less, about 5 pM or less, about 4 pM or less, about 3 pM or less, about 2 pM or less, about 1 pM or less, about 0.9 pM or less, about 0.8 pM or less, about 0.7 pM or less, about 0.6 pM or less, about 0.5 pM or less, about 0.4 pM or less, about 0.3 pM or less, about 0.2 pM or less, about 0.1 pM, about 50 fM or less, about 40 fM or less, about 30 fM or less, about 20 fM or less, about 10 fM or less, about 5 fM or less, about 4 fM or less, about 3 fM or less, about 2 fM or less, or even about 1 fM or less of neurotoxin polypeptide. For example, an extremely low EC50 value of about 3 fM has been found by the present inventors for induced pluripotent stem cell (iPS)-derived neurons to which GT1b has externally been added to the cell culture medium in the methods of the present invention. As known in the art, the "half maximal effective concentration (EC50)" refers to the concentration of a drug, antibody or toxicant which induces a response halfway between the baseline and maximum after some specified exposure time. It is commonly used as a measure of a drug's potency. The EC50 of a graded dose response curve therefore represents the concentration of a compound where 50% of its maximal effect is observed. The EC50 of a quantal dose response curve represents the concentration of a compound where 50% of the population exhibits a response, after an exposure duration. Methods for the identification of cells or cell lines susceptible to neurotoxin intoxication and/or having neurotoxin uptake capacity, i.e. neurotoxin-sensitive cells as defined herein, are known in the art; see, e.g. US 2012/0122128 A1. The biological activity of the neurotoxin polypeptides, in an aspect, results from all of the aforementioned biological properties. Only a few cell-based assays with sufficient high sensitivity towards neurotoxins which can be used for the determination of the biological activity of a neurotoxin have been described in the prior art so far, as indicated elsewhere herein. In vivo assays for assessing the biological activity of neurotoxins include, for example, the already mentioned mouse $LD_{50}$ assay and the ex vivo mouse hemidiaphragm assay as described by Pearce et al. and Dressier et al.; see Pearce 1994, Toxicol. Appl. Pharmacol. 128: 69-77 and Dressier 2005, Mov. Disord. 20:1617-1619. As known to those skilled in the art, the biological activity of neurotoxins is commonly expressed in Mouse $LD_{50}$ Units (MU). One MU is the amount of neurotoxic component, which kills 50% of a specified mouse population after intraperitoneal injection.

More specifically, "induced pluripotent stem cell (iPS)-derived neurons" as used herein are described in the literature; see, for example, Whitemarsh et al., loc. cit; WO 2012/135621; US 2010/0279403 and US 2010/0216181. In particular, human induced pluripotent stem cells (hiPSC) hold great promise for providing various differentiated cell models for in vitro toxigenicity testing. hiPSC-derived neurons were differentiated and cryopreserved, e.g., by Cellular Dynamics International (Madison, Wis.) and consist of an almost pure pan-neuronal population of predominantly gamma aminoisobutyric acidergic and glutamatergic neurons. Said hiPSC-derived neurons are known as iCell® neurons. Western blot and quantitative PCR data showed that these neurons express all the necessary receptors and substrates for BoNT intoxication, according to the provider. BoNT/A intoxication studies demonstrated that the hiPSC-derived neurons reproducibly and quantitatively detect biologically active BoNT/A with high sensitivity. Additionally, the quantitative detection of BoNT serotypes B, C, E, and BoNT/A complex was demonstrated, and BoNT/A specificity was confirmed through antibody protection studies. A direct comparison of BoNT detection using primary rat spinal cord cells and hiPSC-derived neurons showed equal or increased sensitivity, a steeper dose-response curve and a more complete SNARE protein target cleavage for hiPSC-derived neurons; see Whitemarsh et al., loc. cit. These data suggested that neurons derived from hiPSCs provide an ideal and highly sensitive platform for BoNT potency determination, neutralizing antibody detection and for mechanistic studies. In an aspect of the methods of the invention, the induced pluripotent stem cell-derived neurons are mammalian (such as rodent, cynomolgus, macaque or chimpanzee) induced pluripotent stem cell (iPS)-derived neurons, preferably human induced pluripotent stem cell (iPS)-derived neurons. Preferably, said induced pluripotent stem cell-derived neurons are iCell® neurons (Cellular Dynamics International, Inc. (CDI)). According to the provider, iCell® neurons are derived from human induced pluripotent stem (iPS) cells and provide a unique in vitro system for preclinical drug discovery, neurotoxicity testing and disease research. Moreover, iCell® neurons offer high quality and highly pure human neuronal cells that possess typical phenotypic characteristics and functionality of mature neurons. Historically, in vitro models have played an important role in the drug discovery process including use during early stage disease modeling and candidate in the identification as well as pharmacokinetic and safety testing. Because of the complexity of the human brain, scientists currently use simplified models such as primary cells isolated from rodent tissues and transformed cell lines. Issues of biological relevance, reproducibility, and scalability can raise and the reliance on inferior models may result in drug-induced neurotoxicity not being observed until late-stage clinical trials or after marketplace introduction in the field of neurotoxins. iCell® neurons overcome these limitations providing a robust, well characterized highly reproducible in vitro model for preclinical neurotoxin safety testing. iCell® neurons are terminally differentiated from human iPS cells and exhibit neuronal characteristics and functions. iCell® neurons are highly pure, providing biologically relevant and reproducible results. iCell® neurons remain viable and pure in culture for weeks, enabling assessment of both acute and subchronic responses. Further, iCell® neurons are shipped cryopreserved with cell culture media specifically formulated for optimal cell performance. They are simple to thaw and use, according to the provider's manual. However, different batches of iCell® neurons have been found by the present inventors to differ drastically with respect to the sensitivity of said batches to neurotoxin polypeptides. As a result, strong divergences in the measured values of the biological activity of neurotoxins have been obtained for different batches. In order to reduce the variability of the sensitivity of the different batches of iPS-derived neurons to a neurotoxin polypeptide, the external addition of GT1b to the cell culture medium can advantageously be used in accordance with the methods of the invention.

As used herein, the singular forms "a", "an" and "the" include both singular and plural reference unless the context clearly dictates otherwise. By way of example, "a cell" refers to one or more than one cell.

As used herein, the term "about" when qualifying a value of a stated item, number, percentage, or term refers to a range of plus or minus 10 percent, 9 percent, 8 percent, 7 percent, 6 percent, 5 percent, 4 percent, 3 percent, 2 percent or 1 percent of the value of the stated item, number, percentage, or term. Preferred is a range of plus or minus 10 percent.

The terms "comprising", "comprises" and "comprised of" as used herein are synonyms with "including", "includes" or "containing", "contains", and are inclusive or open-ended and do not exclude additional, non-recited members, elements or method steps. Evidently, the term "comprising" encompasses the term "consisting of". More specifically, the term "comprise" as used herein means that the claim encompasses all the listed elements or method steps, but may also include additional, unnamed elements or method steps. For example, a method comprising steps a), b) and c) encompasses, in its narrowest sense, a method which consists of steps a), b) and c). The phrase "consisting of" means that the composition (or device, or method) has the recited elements (or steps) and no more. In contrast, the term "comprises" can encompass also a method including further steps, e.g., steps d) and e), in addition to steps a), b) and c).

In case numerical ranges are used herein such as "GT1b in a concentration from 10 to 50 µM the range includes not only 10 and 50 µM, but also any numerical value in between 10 and 50 µM, for example, 15 µM, 20 µM, 25 µM, 30 µM, 35 µM, 40 µM and 45 µM GT1b.

The term "in vitro" as used herein denotes outside, or external to, the animal or human body. The term "in vitro" as used herein should be understood to include "ex vivo". The term "ex vivo" typically refers to tissues or cells removed from an animal or human body and maintained or propagated outside the body, e.g., in a culture vessel. The term "in vivo" as used herein denotes inside, or internal to, the animal or human body.

The terms "differentiation", "differentiating" or "differentiated" as used herein denote the process by which an unspecialized or a relatively less specialized cell becomes relatively more specialized. In the context of cell ontogeny, the adjective "differentiated" is a relative term. Hence, a "differentiated cell" is a cell that has progressed further down a certain developmental pathway than the cell it is being compared with. A differentiated cell may, for example, be a terminally differentiated cell, i.e., a fully specialized cell that takes up specialized functions in various tissues and organs of an organism, and which may but need not be post-mitotic. For instance, iCell® neurons are terminally differentiated from human iPS cells and exhibit neuronal characteristics and functions. In another example, a differentiated cell may also be a progenitor cell within a differentiation lineage, which can further proliferate and/or differentiate. Similarly, a cell is "relatively more specialized" if it has progressed further down a certain developmental pathway than the cell it is being compared with, wherein the latter is therefore considered "unspecialized" or "relatively less specialized". A relatively more specialized cell may differ from the unspecialized or relatively less specialized cell in one or more demonstrable phenotypic characteristics, such as, for example, the presence, absence or level of expression of particular cellular components or products, e.g., RNA, proteins, specific cellular markers or other substances, activity of certain biochemical pathways, morphological appearance, proliferation capacity and/or kinetics, differentiation potential and/or response to differentiation signals, etc., wherein such characteristics signify the progression of the relatively more specialized cell further along the said developmental pathway.

The term "neurotoxin polypeptide" as used herein denotes Clostridium botulinum and Clostridium tetani neurotoxins (or Clostridial neurotoxins), i.e. Botulinum toxins (BoNTs) and Tetanus toxin (TeNT). Recently, a new Botulinum toxin type, i.e. BoNT/H, has been identified; see Barash and Arnon, J. Infect. Dis. (2014), 209 (2): 183-191. More specifically, said term encompasses BoNT/A, BoNT/B, BoNT/C1, BoNT/D, BoNT/E, BoNT/F, BoNT/G, BoNT/H and Tetanus neurotoxin (TeNT), or subtypes thereof. For example, the subtypes of BoNT/A include BoNT/A1, BoNT/A2, BoNT/A3, BoNT/A4, and BoNT/A5. The BoNT/B subtypes encompass, for instance, BoNT/B1, BoNT/B2, BoNT/B3, BoNT/B4, BoNT/B5, BoNT/B6 and BoNT/B7. The BoNT/C subtypes comprise, e.g., BoNT/C1-1 and BoNT/C1-2. Encompassed is also the BoNT/D-C subtype. The BoNT/E subtypes include, e.g., BoNT/E1, BoNT/E2, BoNT/E3, BoNT/E4, BoNT/E5, BoNT/E6, BoNT/E7, and BoNT/E8. Further, the BoNT/F subtypes comprise, for instance, BoNT/F1, BoNT/F2, BoNT/F3, BoNT/F4, BoNT/F5, BoNT/F6, and BoNT/F7. The neurotoxin polypeptide and, in particular, its light chain and heavy chain are derivable from one of the antigenically different serotypes of Botulinum neurotoxins indicated above. In an aspect, said light and heavy chain of the neurotoxin polypeptide are the light and heavy chain of a neurotoxin selected from the group consisting of: BoNT/A, BoNT/B, BoNT/C1, BoNT/D, BoNT/E, BoNT/F, BoNT/G, BoNT/H or TeNT. In another aspect, the polynucleotide encoding said neurotoxin polypeptides comprises a nucleic acid sequence as shown in SEQ ID NO: 1 (BoNT/A), SEQ ID NO: 3 (BoNT/B), SEQ ID NO: 5 (BoNT/C1), SEQ ID NO: 7 (BoNT/D), SEQ ID NO: 9 (BoNT/E), SEQ ID NO: 11 (BoNT/F), SEQ ID NO: 13 (BoNT/G) or SEQ ID NO: 15 (TeNT). Moreover, encompassed is, in an aspect, a polynucleotide comprising a nucleic acid sequence encoding an amino acid sequence as shown in any one of SEQ ID NO: 2 (BoNT/A), SEQ ID NO: 4 (BoNT/B), SEQ ID NO: 6 (BoNT/C1), SEQ ID NO: 8 (BoNT/D), SEQ ID NO: 10 (BoNT/E), SEQ ID NO: 12 (BoNT/F), SEQ ID NO: 14 (BoNT/G) or SEQ ID NO: 16 (TeNT). Further encompassed is in an aspect of the means and methods of the present invention, a neurotoxin polypeptide comprising or consisting of an amino acid sequence selected from the group consisting of: SEQ ID NO: 2 (BoNT/A), SEQ ID NO: 4 (BoNT/B), SEQ ID NO: 6 (BoNT/C1), SEQ ID NO: 8

(BoNT/D), SEQ ID NO: 10 (BoNT/E), SEQ ID NO: 12 (BoNT/F), SEQ ID NO: 14 (BoNT/G) and SEQ ID NO: 16 (TeNT). The corresponding sequences of BoNT/H are shown in the publication by Dover et al., J. Infect. Dis. (2014), 209 (2): 192-202. Said BoNT/H sequences are also encompassed, in specific aspects of the means and methods of the invention.

In another aspect, the said polynucleotide is a variant of the aforementioned polynucleotides comprising one or more nucleotide substitutions, deletions and/or additions which in still another aspect may result in a polypeptide having one or more amino acid substitutions, deletions and/or additions. Moreover, a variant polynucleotide shall in another aspect comprise a nucleic acid sequence variant being at least 40%, at least 50%, at least 60%, at least 70%, at least 75%, at least 80%, at least 85%, at least 90%, at least 95%, at least 96%, at least 97%, at least 98% or at least 99% identical to the (preferably complete) nucleic acid sequence as shown in any one of SEQ ID NOs: 1, 3, 5, 7, 9, 11, 13 or 15 or the nucleic acid of BoNT/H, or a nucleic acid sequence variant which encodes an amino acid sequence being at least 40%, at least 50%, at least 60%, at least 70%, at least 75%, at least 80%, at least 85%, at least 90%, at least 95%, at least 96%, at least 97%, at least 98% or at least 99% identical to the (preferably complete) amino acid sequence as shown in any one of SEQ ID NOs: 2, 4, 6, 8, 10, 12, 14, or 16 or the amino acid sequence of BoNT/H. The term "identical" as used herein refers to sequence identity characterized by determining the number of identical amino acids between two nucleic acid sequences or two amino acid sequences wherein the sequences are aligned so that the highest order match is obtained. It can be calculated using published techniques or methods codified in computer programs such as, for example, BLASTP, BLASTN or FASTA (Altschul 1990, J Mol Biol 215, 403). The percent identity values are, in one aspect, calculated over the entire amino acid sequence. A series of programs based on a variety of algorithms is available to the skilled worker for comparing different sequences. In this context, the algorithms of Needleman and Wunsch or Smith and Waterman give particularly reliable results. To carry out the sequence alignments, the program PileUp (Higgins 1989, CABIOS 5, 151) or the programs Gap and BestFit (Needleman 1970, J Mol Biol 48; 443; Smith 1981, Adv Appl Math 2, 482), which are part of the GCG software packet (Genetics Computer Group 1991, 575 Science Drive, Madison, Wis., USA 53711), may be used. The sequence identity values recited above in percent (%) are to be determined, in another aspect of the invention, using the program GAP over the entire sequence region with the following settings: Gap Weight: 50, Length Weight: 3, Average Match: 10.000 and Average Mismatch: 0.000, which, unless otherwise specified, shall always be used as standard settings for sequence alignments. The variant of a Clostridial neurotoxin as referred to herein includes, e.g. a Clostridial neurotoxin produced with the aid of human manipulation, including, without limitation, Clostridial neurotoxin produced by genetic engineering or recombinant methods, e.g., using random mutagenesis or rational design, enzymatically modified variants of Clostridial neurotoxins that are modified by the activity of enzymes, such as endo- or exoproteolytic enzymes, or Clostridial neurotoxins produced by chemical synthesis. "Genetic manipulation" refers to methods known in the art for modifying the native Clostridial neurotoxin of any serotype/subtype by means of modifying the gene encoding for the Clostridial neurotoxin or respective nucleic acids like DNA or mRNA. Recombinant methods for genetic engineering of a polynucleotide encoding a neurotoxin polypeptide or a neurotoxin polypeptide are well described in the art; see, e.g. Sambrook, J. & Russell, D. (2001). Molecular Cloning: a Laboratory Manual, 3 rd edn. Cold Spring Harbor, N.Y.: Cold Spring Harbor Laboratory. The neurotoxin polypeptide variant as used herein further encompasses chemically modified neurotoxin polypeptides. "Chemical modification" as used herein refers generally to methods known in the art for modifying the native or recombinant Clostridial neurotoxin of any serotype or subtype by means of chemical reactions or the like; it refers especially to substitutions, deletions, insertions, additions or posttranslational modifications of amino acids of the Clostridial neurotoxin. A chemically modified neurotoxin polypeptide may be one that is modified by pyruvation, phosphorylation, sulfatation, lipidation, pegylation, glycosylation and/or the chemical addition of an amino acid or a polypeptide comprising, e.g., between about two and about 500 amino acids. For example, by incorporating hyaluronic acid or polyvinylpyrrolidone or polyethyleneglycol or mixtures thereof into the neurotoxin polypeptide, the Clostridial neurotoxin, or the toxin which is derived from Clostridial toxin by chemical modification or by genetic manipulation, can be stabilized. In an aspect, each of the aforementioned variant polynucleotides encodes a polypeptide retaining one or more and, in another aspect, all of the biological properties of the respective neurotoxin polypeptide, i.e. the BoNT/A, BoNT/B, BoNT/C1, BoNT/D, BoNT/E, BoNT/F, BoNT/G, BoNT/H or Tetanus Neurotoxin (TeNT). Those of skill in the art will appreciate that full biological activity is maintained only after proteolytic activation, even though it is conceivable that the unprocessed precursor can exert some biological functions or be partially active. "Biological properties" as used herein refers to (a) receptor binding, (b) internalization, (c) translocation across the endosomal membrane into the cytosol, and/or (d) endoproteolytic cleavage of proteins involved in synaptic vesicle membrane fusion. More specifically, the overall cellular mechanisms whereby a neurotoxin (e.g. BoNT/A) cleaves a neurotoxin substrate (e.g. SNAP-25) encompasses the binding of the neurotoxin to its corresponding receptor (e.g. binding of BoNT/A to BoNT/A receptor), the internalization of the neurotoxin/receptor complex, the translocation of the neurotoxin light chain from an intracellular vesicle into the cytoplasm and the proteolytic cleavage of the neurotoxin substrate. In vitro and in vivo assays for determining the biological activity of a neurotoxin polypeptide are well known in the art. In vivo assays for assessing biological activity include the mouse LD50 assay and the ex vivo mouse hemidiaphragm assay as described by Pearce et al. (Pearce 1994, Toxicol Appl Pharmacol 128: 69-77) and Dressler et al. (Dressler 2005, Mov Disord 20:1617-1619, Keller 2006, Neuroscience 139: 629-637). The biological activity is commonly expressed in Mouse Units (MU). As used herein, 1 MU is the amount of neurotoxic component, which kills 50% of a specified mouse population after intraperitoneal injection, i.e. the mouse i.p. LD50. In a further aspect, the variant polynucleotides can encode neurotoxins having improved or altered biological properties, e.g., they may comprise cleavage sites which are improved for enzyme recognition or may be improved for receptor binding or any other property specified above. In some aspects, the neurotoxin polypeptide can be included in a sample. The sample can be, for example, a clinical sample, a biological sample, a food sample, a pharmaceutical or toxicological sample, an antibody sample or the like.

Accordingly, the term "determining the biological activity of a neurotoxin polypeptide" as used herein means measuring the biological activity of a neurotoxin protein, namely, (a) receptor binding, (b) internalization, (c) translocation across the endosomal membrane into the cytosol, and/or (d) endoproteolytic cleavage of proteins involved in synaptic vesicle membrane fusion.

The term "amount" as used herein encompasses the absolute amount of, e.g., a neurotoxin polypeptide or a neurotoxin substrate polypeptide, the relative amount or the concentration of the said polypeptide as well as any value or parameter which correlates thereto or can be derived there from.

The term "determining the amount" of, e.g., a neurotoxin polypeptide or a neurotoxin substrate polypeptide relates to measuring the absolute amount, relative amount or concentration of, e.g., the neurotoxin polypeptide or neurotoxin substrate polypeptide in a quantitative or semi-quantitative manner. Suitable measures for detection are well known to those skilled in the art. It will be understood that the determination of the amount of neurotoxin polypeptides or neurotoxin substrate polypeptides, in an aspect, also requires calibration of the method by applying standard solutions with predefined amounts of neurotoxin polypeptides or neurotoxin substrate polypeptides. How to carry out such a calibration is well known to those skilled in the art.

In an aspect of the methods of the invention, the induced pluripotent stem cell (iPS)-derived neurons are cultivated in a cell culture medium comprising GT1b. The ganglioside GT1b binds to neurotoxin polypeptide and potentially mediates the selectivity of neurotoxins for neurons. Accordingly, GT1b can be used for standardizing the sensitivity of induced pluripotent stem cell (iPS)-derived neurons to a neurotoxin polypeptide. It has been shown by the present inventors that the external addition of GT1b to the iPS-derived neurons reduces drastically the variability of the sensitivity of different batches of said iPS-derived neurons to a neurotoxin polypeptide, in comparison to control batches of iPS-derived neurons treated without GT1b. Preferably, said GT1b is present in a concentration of about 10 to about 50 μM, i.e. in a concentration of about 10 μM, about 15 μM, about 20 μM, about 25 μM, about 30 μM, about 35 μM, about 40 μM, about 45 μM, or about 50 μM, more preferably in a concentration of about 30 μM.

In a further aspect, the present invention relates to a method for determining the biological activity of a neurotoxin polypeptide, comprising the steps of:

a) cultivating induced pluripotent stem cell-derived neurons in a cell culture medium comprising GT1b for at least 3 hours;
b) contacting the induced pluripotent stem cell-derived neurons of step a) with a neurotoxin polypeptide;
c) cultivating the induced pluripotent stem cell-derived neurons of step b) for at least 24 hours in the presence of GT1b under conditions which allow for the neurotoxin polypeptide to exert its biological activity; and
d) determining the biological activity of the neurotoxin polypeptide in said cells.

In a specific aspect of this method of the invention, different batches of induced pluripotent stem cell-derived neurons are used, as defined elsewhere herein.

In one aspect of the methods of the invention, "standardizing of the sensitivity" (of induced pluripotent stem cell-derived neurons to a neurotoxin polypeptide) is a reduction in the variability of the sensitivity of the different batches of induced pluripotent stem cell (iPS)-derived neurons to a neurotoxin polypeptide, in comparison to control batches of induced pluripotent stem cell (iPS)-derived neurons treated under the same conditions, however, without GT1b.

In another aspect, the reduction in the variability of the sensitivity of the different batches of induced pluripotent stem cell (iPS)-derived neurons to a neurotoxin polypeptide is an at least 1.1-fold, at least 1.2-fold, at least 1.3-fold, at least 1.4-fold, at least 1.5-fold, at least 1.6-fold, at least 1.7-fold, at least 1.8-fold, at least 1.9-fold, at least 2-fold, at least 2.1-fold, at least 2.2-fold, at least 2.3-fold, at least 2.4-fold, at least 2.5-fold, or even at least 3-fold reduction, in comparison to control batches of induced pluripotent stem cell (iPS)-derived neurons treated under the same conditions, however, without GT1b.

In other aspects of the methods of the invention, the induced pluripotent stem cell (iPS)-derived neurons are human induced pluripotent stem cell (iPS)-derived neurons. Preferably, said induced pluripotent stem cell (iPS)-derived neurons are iCell® neurons (Cellular Dynamics International; loc. cit.).

In one aspect of the methods of the invention, the different batches of induced pluripotent stem cell (iPS)-derived neurons differ in the number of passages, the number of freeze/thaw cycles, the cultivation conditions, the storage time, the growth time, the differentiation conditions, or combinations thereof.

In another aspect of the methods of the invention, the cell culture medium comprises Neurobasal® Medium, B-27® Supplement (2%), and Glutamin or GlutaMAX™, a formulation of 200 mM (100×) L-alanyl-L-glutamine dipeptide in 0.85% NaCl, (1%). Optionally the cell culture medium can comprise antibiotics (1%), N2 supplement (1%) and/or Serum Albumin (0.2%).

In further aspects of the methods of the invention, GT1b is added in a concentration of 1 to 300 μM, preferably 30 μM.

In another aspect of the methods of the invention, the neurotoxin polypeptide is BoNT/A, BoNT/B, BoNT/C1, BoNT/D, BoNT/E, BoNT/G, BoNT/F, BoNT/H or TeNT, or a subtype thereof.

In a still further aspect of the methods of the invention, the biological activity of the neurotoxin polypeptide is determined by quantification of the neurotoxin-cleaved substrate by Immuno-Western blot analysis, SDS-PAGE immunoblot analysis or ELISA (see, e.g., Pellet et al. (2010), J. Pharmacol. Toxicol. Methods 61, 304-310).

In a further aspect, the invention relates to the use of GT1b for a) standardizing the sensitivity of different batches of induced pluripotent stem cell (iPS)-derived neurons to a neurotoxin polypeptide; or
b) reducing the variability of the sensitivity of different batches of induced pluripotent stem cell (IPS)-derived neurons to a Neurotoxin polypeptide.

Specific aspects of the methods and uses of the present invention are shown in the following Examples.

The Figures show:

FIG. 1: SiMa cells were cultivated and intoxicated as described in Example 2 and the ratio of cleaved to uncleaved SNAP-25 was determined by Western Blot analysis. On the X-axis the concentration of the Botulinum Neurotoxin type is given, whereas on the Y-axis the relative amount of cleaved SNAP-25, i.e. the ratio of cleaved to uncleaved SNAP-25 is plotted. The circles symbolize SiMa cells cultivated without GT1b, the squares symbolize SiMa cells cultivated with 30 μM GT1b. The cultivation with GT1b led to an increase in sensitivity of about 10-fold.

FIG. 2: SH-SY5Y cells were cultivated and intoxicated as described in Example 2 and the ratio of cleaved to uncleaved SNAP-25 was determined by Western Blot analysis. On the X-axis the concentration of the Botulinum Neurotoxin type is given, whereas on the Y-axis the relative amount of cleaved SNAP-25, i.e. the ratio of cleaved to uncleaved SNAP-25 is plotted. The circles symbolize SH-SY5Y cells cultivated without GT1b, the squares symbolize SH-SY5 cells cultivated with 30 µM GT1b. The cultivation with GT1b led to an increase in sensitivity of about 2-fold.

Figure 3:
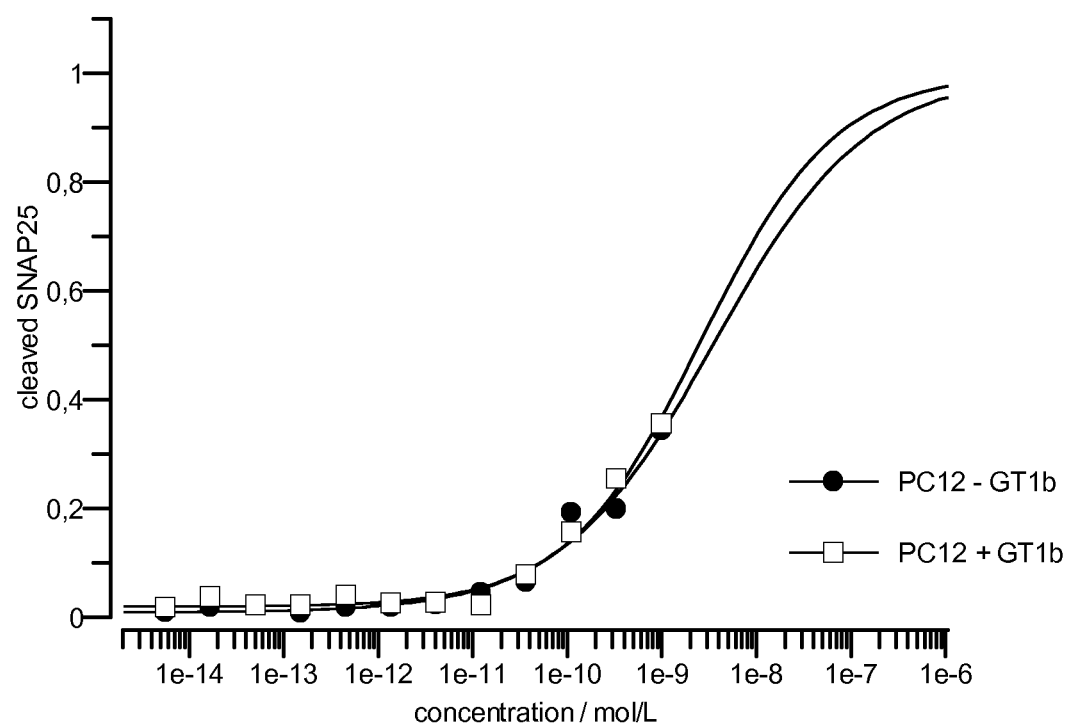

FIG. 3: PC12 cells were cultivated and intoxicated as described in Example 2 and the ratio of cleaved to uncleaved SNAP-25 was determined by Western Blot analysis. On the X-axis the concentration of the Botulinum Neurotoxin type is given, whereas on the Y-axis the relative amount of cleaved SNAP-25, i.e. the ratio of cleaved to uncleaved SNAP-25 is plotted. The circles symbolize PC12 cells cultivated without GT1b, the squares symbolize PC12 cells cultivated with 30 µM GT1b. The cultivation with GT1b led to an increase in sensitivity of about 1.4-fold.

Figure 4:
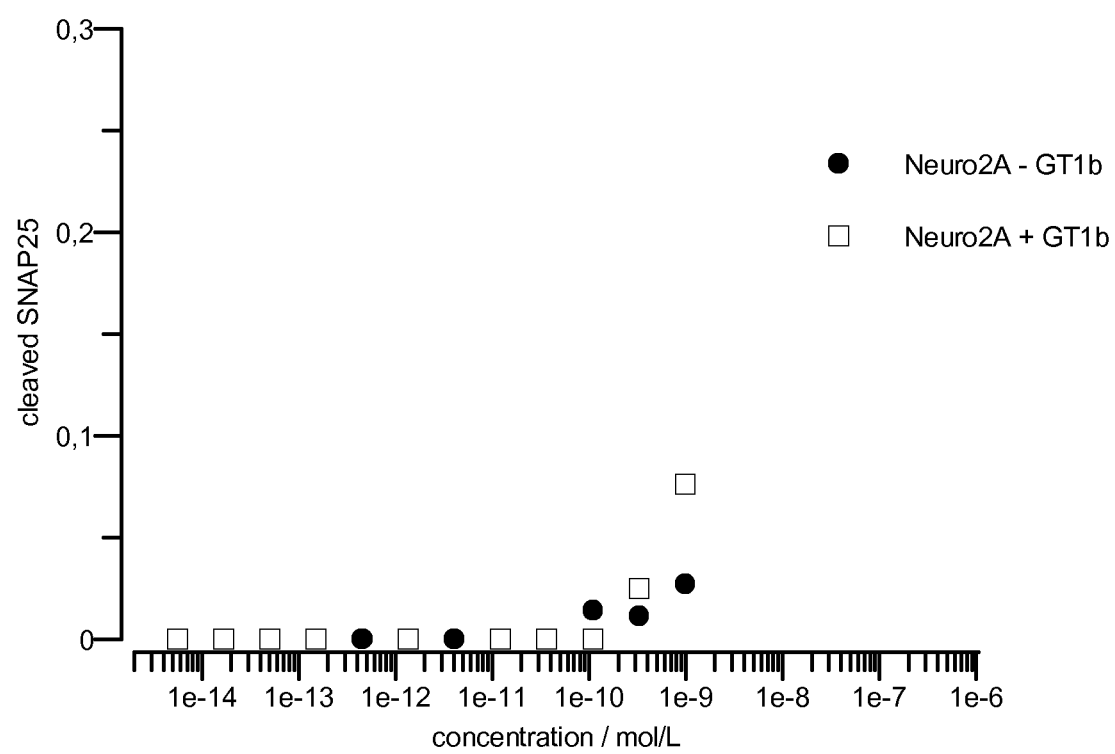

FIG. 4: Neuro2A-cells were cultivated and intoxicated as described in Example 2 and the ratio of cleaved to uncleaved SNAP-25 was determined by Western Blot analysis. On the X-axis the concentration of the Botulinum Neurotoxin type is given, whereas on the Y-axis the relative amount of cleaved SNAP-25, i.e. the ratio of cleaved to uncleaved SNAP-25 is plotted. The circles symbolize Neuro2A cells cultivated without GT1b, the squares symbolize Neuro2A cells cultivated with 30 µM GT1b. At the given neurotoxin concentrations, no complete dose response curve could be observed as well as no increase in sensitivity with GT1b.

Figure 5:
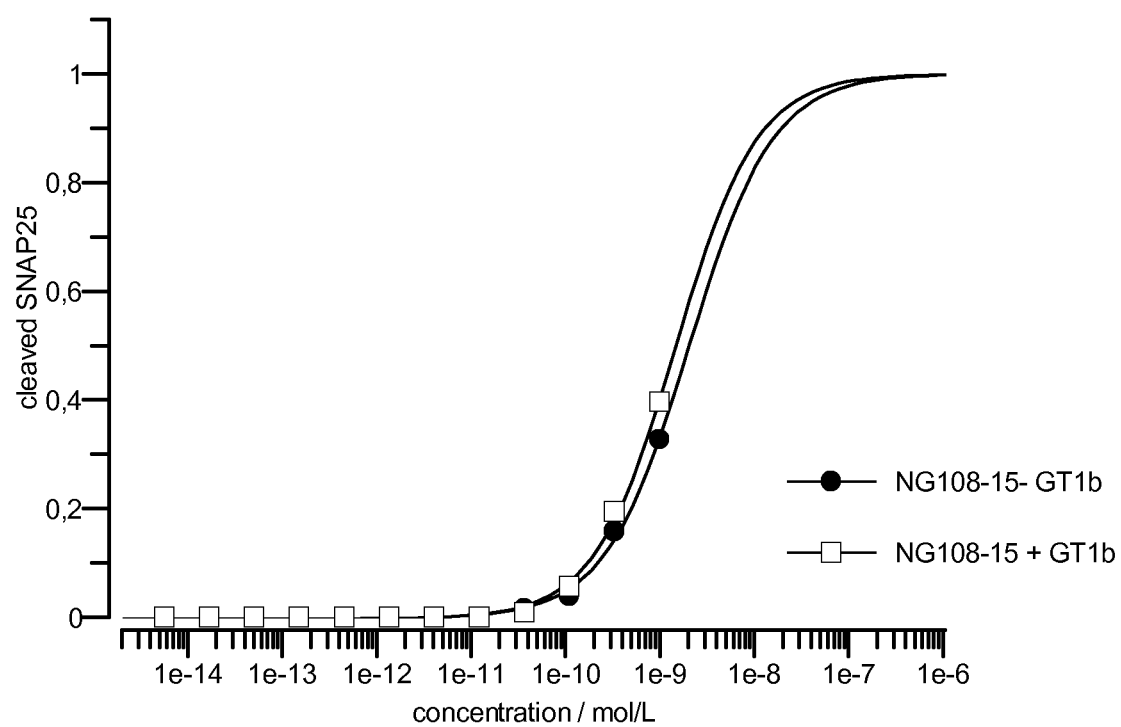

FIG. 5: NG108-15-cells were cultivated and intoxicated as described in Example 2 and the ratio of cleaved to uncleaved SNAP-25 was determined by Western Blot analysis. On the X-axis the concentration of the Botulinum Neurotoxin type is given, whereas on the Y-axis the relative amount of cleaved SNAP-25, i.e. the ratio of cleaved to uncleaved SNAP-25 is plotted. The circles symbolize NG108-15-cells cultivated without GT1b, the squares symbolize NG108-15-cells cultivated with 30 µM GT1b. The cultivation with GT1b led to an increase in sensitivity of about 1.6-fold.

The invention will now be illustrated by the following examples which shall, however, not be construed as limiting the scope of the present invention.

EXAMPLES

Example 1 iCell® neurons were thawed and plated according to the Cellular Dynamics International (CDI) user manual on 96 well plates from 4 different cell batches. 24 hours (h) after plating the medium was replaced by either fresh maintenance medium as described in the user manual or by the same medium supplemented with 30 µM GT1b.

After further 72 h incubation time, the medium was removed and replaced by fresh medium containing BoNT/A in varying concentrations. If cells were grown on GT1b containing medium the fresh medium also contained 30 µM GT1b.

72 h after start of the intoxication, the medium was aspirated and the cells were lysed by addition of 25 µl SDS sample buffer.

The percentage of cleaved SNAP-25 was determined by SDS-PAGE immunoblot analysis, as described in Pellett et al., 2010 (loc. cit.).

The EC50 (concentration of BoNT/A yielding half maximum cleavage of SNAP-25) was calculated by plotting the percent cleaved SNAP-25 versus the BoNT/A concentration.

The resulting EC50 values of the different cell batches with and without addition of GT1b are shown in Table 1.

TABLE 1

|  | EC50 without GT1b | EC50 with GT1b |
| --- | --- | --- |
| Batch 02 | 2.84 U/ml | 0.65 U/ml |
| Batch 03 | 5.37 U/ml | 0.89 U/ml |
| Batch 04 | 6.40 U/ml | 0.77 U/ml |
| Batch 05 | 5.47 U/ml | 0.68 U/ml |
| Mean | 5.02 U/ml | 0.75 U/ml |
| RSD | 30.3% | 14.6% |

Despite the higher sensitivity resulting from the addition of GT1b lowering the EC50 from ~5.0 to ~0.75 U/mL, the relative standard deviation of the EC50 values of the batches is reduced from ~30% to ~15%.

Example 2

Cultivation and differentiation of SiMa cells (see FIG. 1): A vial containing SiMa-cells was thawed and re-suspended in culture medium (90% RPMI 1640+10% h.i. FBS+2 mM L-glutamine+/−30 µM GT1b) to a final density of 30,000 cells/mL. The cells were seeded on poly-D-lysine coated 96-well microtiter plates at 3,000 cells/well and incubated for 72 hours at 37° C., 95% $O_2$/5% $CO_2$ under a saturated water vapor atmosphere. After 72 hours, the medium was exchanged to serum-free medium (MEM+2% B27+1% N2+2% Non-essential amino acids+2 mM L-glutamine+/−30 µM GT1b) containing Botulinum neurotoxin type A in concentrations ranging from $1.0*10^{-9}$ to $5.65*10^{-15}$ M. After 72 hours of incubation as indicated above, the medium was removed, the cells were re-suspended in lysis buffer (20 mM Tris/HCl, 20 mM NaCl, 2 mM $MgCl_2$, 0.5% Triton X-100, 5 U/mL benzonase at pH 8.0), mixed with RotiLoad 1 SDS sample buffer and subjected to Western Blot analysis to determine the ratio of cleaved SNAP-25/uncleaved SNAP-25 as described in Whitemarsh et al. (2012), Toxicol. Sci. 126, 426-35, using an antibody generated in mice (Synaptic Systems SySy111111).

Figure 2:
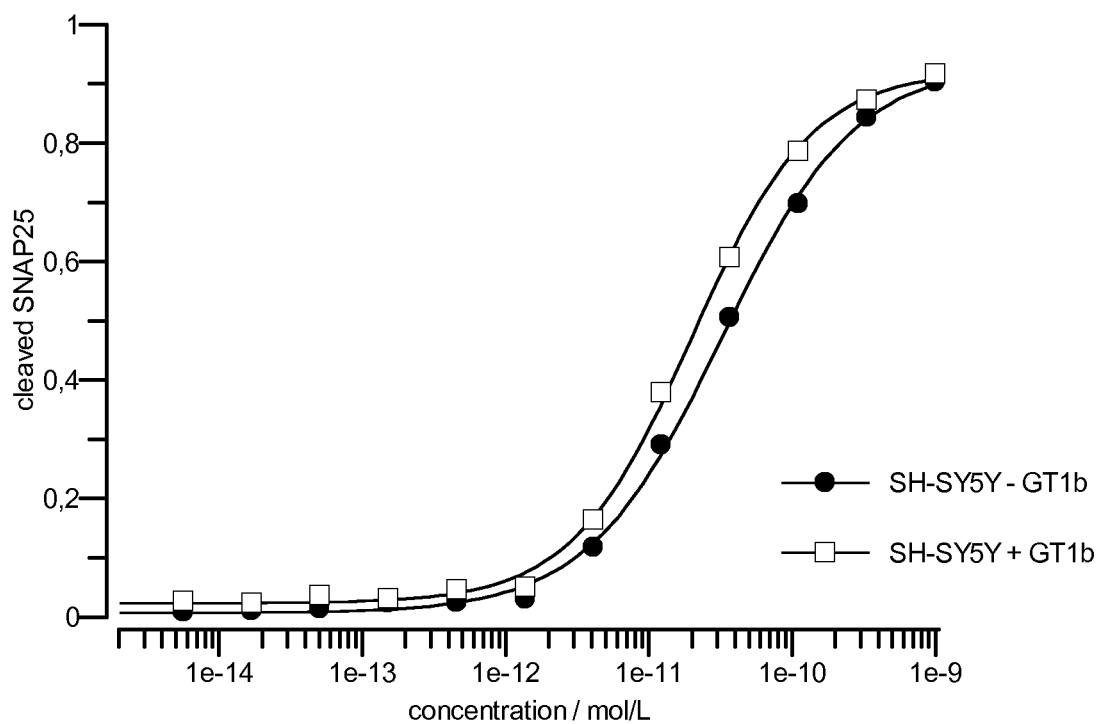

Cultivation and differentiation of SH-SY5Y cells (see FIG. 2): A vial containing SH-SY5Y-cells was thawed and re-suspended in culture medium (85% MEM:F12+15% h.i. FBS+/−30 µM GT1b) to a final density of 60,000 cells/mL. The cells were seeded on uncoated 96-well microtiter plates at 6,000 cells/well and incubated for 24 hours at 37° C., 95% $O_2$/5% $CO_2$ under a saturated water vapor atmosphere. The medium was then supplemented with Nerve Growth factor (100 ng/ml) and Aphidicoline (0.3 mM)+/−30 µM GT1b. This medium was exchanged every 2-3 days. After 17 days of incubation, the medium was exchanged to fresh medium containing Botulinum neurotoxin type A in concentrations ranging from $1.0*10^{-9}$ to $5.65*10^{-15}$ M. After 72 hours of incubation as indicated above, the medium was removed, the cells were re-suspended in lysis buffer (20 mM Tris/HCl, 20 mM NaCl, 2 mM $MgCl_2$, 0.5% Triton X-100, 5 U/mL benzonase at pH 8.0), mixed with RotiLoad 1 SDS sample buffer and subjected to Western blot analysis to determine the ratio of cleaved SNAP-25/uncleaved SNAP-25 as described in Whitemarsh et al. (2012), Toxicol. Sci. 126, 426-35, using an antibody produced in mice (Synaptic Systems SySy111111).

Cultivation and differentiation of PC12 cells (see FIG. 3): A vial containing PC12 cells was thawed and re-suspended in culture medium (85% RPMI 1640+10% horse serum+5% h.i. FBS+/−30 µM GT1b) to a final density of 25,000 cells/mL. The cells were seeded on collagen coated 96-well microtiter plates at 2,500 cells/well and incubated for 72 hours at 37° C., 95% $O_2$/5% $CO_2$ under a saturated water vapor atmosphere. The medium was then supplemented with Nerve Growth factor (100 ng/ml)+/−30 μM GT1b. This medium was exchanged every 2-3 days. After 11 days of incubation, the medium was exchanged to fresh medium containing Botulinum neurotoxin type A in concentrations ranging from $1.0*10^{-9}$ to $5.65*10^{-15}$ M. After 72 hours of incubation as indicated above, the medium was removed, the cells were re-suspended in lysis buffer (20 mM Tris/HCl, 20 mM NaCl, 2 mM $MgCl_2$, 0.55% Triton X-100, 5 U/mL benzonase at pH 8.0), mixed with RotiLoad 1 SDS sample buffer and subjected to Western blot analysis to determine the ratio of cleaved SNAP-25/uncleaved SNAP-25 as described in Whitemarsh et al. (2012), Toxicol. Sci. 126, 426-35, using an antibody generated in mice (SYNAPTIC Systems SySy111111).

Cultivation and differentiation of Neuro2A cells (see FIG. 4): A vial containing Neuro2A cells was thawed and re-suspended in culture medium (90% DMEM+10% h.i. FBS+/−30 μM GT1b) to a final density of 20,000 cells/mL. The cells were seeded on 96-well microtiter plates at 2,000 cells/well and incubated for 24 hours at 37° C., 95% $O_2$/5% $CO_2$ under a saturated water vapor atmosphere. The medium was exchanged by serum-free DMEM+/−30 μM GT1b followed by 3 days of incubation at 37° C. Then the medium was exchanged to fresh serum-free medium containing 0.2% BSA+/−30 μM GT1b and Botulinum neurotoxin type A in concentrations ranging from $1.0*10^{-9}$ to $5.65*10^{-15}$ M. After 72 hours of incubation as indicated above, the medium was removed, the cells were re-suspended in lysis buffer (20 mM Tris/HCl, 20 mM NaCl, 2 mM $MgCl_2$, 0.5% Triton X-100, 5 U/mL benzonase at pH 8.0), mixed with RotiLoad 1 SDS sample buffer and subjected to Western blot analysis to determine the ratio of cleaved SNAP-25/uncleaved SNAP-25 as described in Whitemarsh et al. (2012), Toxicol. Sci. 126, 426-35, using an antibody produced in mice (SYNAPTIC Systems SySy111111).

Cultivation and differentiation of NG108-15 cells (see FIG. 5): A vial containing SH-SY5Y cells was thawed and re-suspended in culture medium (90% DMEM+10% h.i. FBS+/−30 μM GT1b) to a final density of 60,000 cells/mL. The cells were seeded on 96-well microtiter plates at 6,000 cells/well and incubated for 72 hours at 37° C., 95% $O_2$/5% $CO_2$ under a saturated water vapor atmosphere. The medium was then supplemented with dibutyryl-cAMP (1 mM)+/−30 μM GT1b. This Medium was exchanged every 2-3 days. After 5 days of incubation, the medium was exchanged to fresh medium containing Botulinum neurotoxin type A in concentrations ranging from $1.0*10^{-9}$ to $5.65*10^{-15}$ M. After 72 hours of incubation as indicated above, the medium was removed, the cells were re-suspended in lysis buffer (20 mM Tris/HCl, 20 mM NaCl, 2 mM $MgCl_2$, 0.5% Triton X-100, 5 U/mL benzonase at pH 8.0), mixed with RotiLoad 1 SDS sample buffer and subjected to Western blot analysis to determine the ratio of cleaved SNAP-25/uncleaved SNAP-25 as described in Whitemarsh et al. (2012), Toxicol. Sci. 126, 426-35 using an antibody generated in mice (Synaptic Systems SySy111111).

The invention claimed is:

1. A method for standardizing the sensitivity of induced pluripotent stem cell (iPS)-derived neurons to a neurotoxin polypeptide, comprising the steps of:
  a) measuring the sensitivity of neurons from different batches of induced pluripotent stem cell-derived neurons to a neurotoxin polypeptide to establish variability in sensitivity across the different batches;
  b) cultivating neurons from said different batches of induced pluripotent stem cell-derived neurons in a cell culture medium comprising GT1b for at least 3 hours;
  c) contacting the neurons of step b) with a neurotoxin polypeptide;
  d) cultivating neurons of step c) for at least 24 hours in the presence of GT1b under conditions which allow for the neurotoxin polypeptide to exert its biological activity;
  e) measuring the sensitivity of the different batches of induced pluripotent stem cell-derived neurons to a neurotoxin polypeptide in step d) to establish a reduction in variability in sensitivity across the different batches relative to the variability in sensitivity across the different batches in step a).

2. The method of claim 1, wherein the reduction in the variability of the sensitivity of the different batches of induced pluripotent stem cell-derived neurons to a neurotoxin polypeptide is an at least 1.5-fold or at least 2-fold reduction.

3. The method of claim 1, wherein the induced pluripotent stem cell-derived neurons are human induced pluripotent stem cell-derived neurons.

4. The method of claim 1, wherein the different batches of induced pluripotent stem cell-derived neurons differ in the number of passages, the number of freeze/thaw cycles, the cultivation conditions, the storage time, the growth time, the differentiation conditions, or combinations thereof.

5. The method of claim 1, wherein the cell culture medium comprises Neurobasal medium, B27 Supplement (2%), and Glutamin or Glutamax (1%).

6. The method of any of claim 1, wherein GT1b is added in a concentration of 1 to 300 µM.

7. The method of claim 1, wherein the neurotoxin polypeptide is BoNT/A, BoNT/B, BoNT/C1, BoNT/D, BoNT/E, BoNT/F, BoNT/G, BoNT/H or TeNT, or a subtype thereof.

8. The method of claim 1, wherein the sensitivity of induced pluripotent stem cell-derived neurons to a neurotoxin polypeptide is measured by quantification of the neurotoxin-cleaved substrate.

9. The method of claim 8, wherein neurotoxin-cleaved substrate is quantified by Immuno-Western blot analysis, SDS-PAGE Immunoblot analysis or ELISA.

10. A method for determining the biological activity of a neurotoxin polypeptide, comprising the steps of:
  a) measuring the sensitivity of neurons from different batches of induced pluripotent stem cell-derived neurons to a neurotoxin polypeptide;

b) cultivating neurons from said different batches of induced pluripotent stem cell-derived neurons in a cell culture medium comprising 1 to 300 µM GT1b for at least 3 hours;

c) contacting the neurons of step b) with a neurotoxin polypeptide selected from BoNT/A, BoNT/B, BoNT/C1, BoNT/D, BoNT/E, BoNT/F, BoNT/G, BoNT/H or TeNT, or a subtype thereof;

d) cultivating neurons of step c) for at least 24 hours in the presence of 1 to 300 µM GT1b under conditions which allow for the neurotoxin polypeptide to exert its biological activity;

e) measuring the sensitivity of the different batches of induced pluripotent stem cell-derived neurons to a neurotoxin polypeptide in step d) wherein the sensitivity of the neurons of step d) is increased at least 2-fold, in comparison to the sensitivity neurons from step a).

* * * * *

SEQUENCE LISTING

```
<160> NUMBER OF SEQ ID NOS: 16

<210> SEQ ID NO 1
<211> LENGTH: 3891
<212> TYPE: DNA
<213> ORGANISM: Clostridium botulinum

<400> SEQUENCE: 1
atgccatttg ttaataaaca atttaattat aaagatcctg taaatggtgt tgatattgct      60
tatataaaaa ttccaaatgc aggacaaatg caaccagtaa aagcttttaa aattcataat     120
aaaatatggg ttattccaga aagagataca tttacaaatc ctgaagaagg agatttaaat     180
ccaccaccag aagcaaaaca agttccagtt tcatattatg attcaacata tttaagtaca     240
gataatgaaa aagataatta tttaaaggga gttacaaaat tatttgagag aatttattca     300
actgatcttg gaagaatgtt gttaacatca atagtaaggg gaataccatt ttggggtgga     360
agtacaatag atacagaatt aaaagttatt gatactaatt gtattaatgt gatacaacca     420
gatggtagtt atagatcaga agaacttaat ctagtaataa taggaccctc agctgatatt     480
atacagtttg aatgtaaaag ctttggacat gaagttttga atcttacgcg aaatggttat     540
ggctctactc aatacattag atttagccca gatttttacat ttggttttga ggagtcactt     600
gaagttgata caaatcctct tttaggtgca ggcaaatttg ctacagatcc agcagtaaca     660
ttagcacatg aacttataca tgctggacat agattatatg gaatagcaat taatccaaat     720
agggttttta aagtaaatac taatgcctat tatgaaatga gtgggttaga agtaagcttt     780
gaggaactta gaacatttgg gggacatgat gcaaagttta tagatagttt acaggaaaac     840
gaatttcgtc tatattatta taataagttt aaagatatag caagtacact taataaagct     900
aaatcaatag taggtactac tgcttcatta cagtatatga aaaatgtttt taaagagaaa     960
```

```
tatctcctat ctgaagatac atctggaaaa ttttcggtag ataaattaaa atttgataag   1020
ttatacaaaa tgttaacaga gatttacaca gaggataatt ttgttaagtt ttttaaagta   1080
cttaacagaa aaacatattt gaattttgat aaagccgtat ttaagataaa tatagtacct   1140
aaggtaaatt acacaatata tgatggattt aatttaagaa atacaaattt agcagcaaac   1200
tttaatggtc aaaatacaga aattaataat atgaattttta ctaaactaaa aaattttact   1260
ggattgtttg aatttttataa gttgctatgt gtaagaggga taataacttc taaaactaaa   1320
tcattagata aaggatacaa taaggcatta aatgatttat gtatcaaagt taataattgg   1380
gacttgtttt ttagtccttc agaagataat tttactaatg atctaaataa aggagaagaa   1440
attacatctg atactaatat agaagcagca gaagaaaata ttagtttaga tttaatacaa   1500
caatattatt taacctttaa ttttgataat gaacctgaaa atatttcaat agaaaatctt   1560
tcaagtgaca ttataggcca attagaactt atgcctaata tagaaagatt tcctaatgga   1620
aaaaagtatg agttagataa atatactatg ttccattatc ttcgtgctca agaatttgaa   1680
catggtaaat ctaggattgc tttaacaaat tctgttaacg aagcattatt aaatcctagt   1740
cgtgtttata catttttttc ttcagactat gtaaagaaag ttaataaagc tacggaggca   1800
gctatgtttt taggctgggt agaacaatta gtatatgatt ttaccgatga aactagcgaa   1860
gtaagtacta cggataaaat tgcggatata actataatta ttccatatat aggacctgct   1920
ttaaatatag gtaatatgtt atataaagat gattttgtag gtgctttaat attttcagga   1980
gctgttattc tgttagaatt tataccagag attgcaatac ctgtattagg tacttttgca   2040
cttgtatcat atattgcgaa taaggttcta accgttcaaa caatagataa tgctttaagt   2100
aaaagaaatg aaaaatggga tgaggtctat aaatatatag taacaaattg gttagcaaag   2160
gttaatacac agattgatct aataagaaaa aaaatgaaag aagctttaga aaatcaagca   2220
gaagcaacaa aggctataat aaactatcag tataatcaat atactgagga agagaaaaat   2280
aatattaatt ttaatattga tgatttaagt tcgaaactta atgagtctat aaataaagct   2340
atgattaata taaataaatt tttgaatcaa tgctctgttt catatttaat gaattctatg   2400
atcccttatg gtgttaaacg gttagaagat tttgatgcta gtcttaaaga tgcattatta   2460
aagtatatat atgataatag aggaaccttta attggtcaag tagatagatt aaaagataaa   2520
gttaataata cacttagtac agatatacct tttcagcttt ccaaatacgt agataatcaa   2580
agattattat ctacatttac tgaatatatt aagaatatta ttaatacttc tatattgaat   2640
ttaagatatg aaagtaatca tttaatagac ttatctaggt atgcatcaaa aataaatatt   2700
ggtagtaaag taaattttga tccaatagat aaaaatcaaa ttcaattatt taatttagaa   2760
agtagtaaaa ttgaggtaat tttaaaaaat gctattgtat ataatagtat gtatgaaaat   2820
tttagtacta gcttttggat aagaattcct aagtattttta acagtataag tctaaataat   2880
gaatatacaa taataaattg tatggaaaat aattcaggat ggaaagtatc acttaattat   2940
ggtgaaataa tctggacttt acaggatact caggaaataa aacaaagagt agtttttaaa   3000
tacagtcaaa tgattaatat atcagattat ataaacagat ggattttgt aactatcact   3060 aataatagat aaataactc taaaatttat ataaatggaa gattaataga tcaaaaacca   3120
atttcaaatt taggtaatat tcatgctagt aataatataa tgtttaaatt agatggttgt   3180
agagatacac atagatatat ttggataaaa tattttaatc ttttttgataa ggaattaaat   3240 gaaaagaaa tcaaagattt atatgataat caatcaaatt caggtatttt aaaagacttt   3300
```

-continued

```
tggggtgatt atttacaata tgataaacca tactatatgt taaatttata tgatccaaat    3360
aaatatgtcg atgtaaataa tgtaggtatt agaggttata tgtatcttaa agggcctaga    3420
ggtagcgtaa tgactacaaa catttattta aattcaagtt tgtataggggg gacaaaattt   3480 attataaaaa aatatgcttc tggaaataaa gataatattg ttagaaataa tgatcgtgta    3540
tatattaatg tagtagttaa aaataaagaa tataggttag ctactaatgc atcacaggca    3600
ggcgtagaaa aaatactaag tgcattagaa atacctgatg taggaaatct aagtcaagta    3660
gtagtaatga agtcaaaaaa tgatcaagga ataacaaata aatgcaaaat gaatttacaa    3720
gataataatg ggaatgatat aggctttata ggatttcatc agtttaataa atagctaaa     3780 ctagtagcaa gtaattggta taatagacaa atagaaagat ctagtaggac tttgggttgc    3840
tcatgggaat ttattcctgt agatgatgga tggggagaaa ggccactgta a             3891
```

<210> SEQ ID NO 2
<211> LENGTH: 1296
<212> TYPE: PRT
<213> ORGANISM: Clostridium botulinum

<400> SEQUENCE: 2

```
Met Pro Phe Val Asn Lys Gln Phe Asn Tyr Lys Asp Pro Val Asn Gly
1               5                   10                  15

Val Asp Ile Ala Tyr Ile Lys Ile Pro Asn Ala Gly Gln Met Gln Pro
            20                  25                  30

Val Lys Ala Phe Lys Ile His Asn Lys Ile Trp Val Ile Pro Glu Arg
        35                  40                  45

Asp Thr Phe Thr Asn Pro Glu Glu Gly Asp Leu Asn Pro Pro Pro Glu
    50                  55                  60

Ala Lys Gln Val Pro Val Ser Tyr Tyr Asp Ser Thr Tyr Leu Ser Thr
65                  70                  75                  80

Asp Asn Glu Lys Asp Asn Tyr Leu Lys Gly Val Thr Lys Leu Phe Glu
                85                  90                  95

Arg Ile Tyr Ser Thr Asp Leu Gly Arg Met Leu Leu Thr Ser Ile Val
            100                 105                 110

Arg Gly Ile Pro Phe Trp Gly Gly Ser Thr Ile Asp Thr Glu Leu Lys
        115                 120                 125

Val Ile Asp Thr Asn Cys Ile Asn Val Ile Gln Pro Asp Gly Ser Tyr
    130                 135                 140

Arg Ser Glu Glu Leu Asn Leu Val Ile Ile Gly Pro Ser Ala Asp Ile
145                 150                 155                 160

Ile Gln Phe Glu Cys Lys Ser Phe Gly His Glu Val Leu Asn Leu Thr
                165                 170                 175

Arg Asn Gly Tyr Gly Ser Thr Gln Tyr Ile Arg Phe Ser Pro Asp Phe
            180                 185                 190

Thr Phe Gly Phe Glu Glu Ser Leu Glu Val Asp Thr Asn Pro Leu Leu
        195                 200                 205

Gly Ala Gly Lys Phe Ala Thr Asp Pro Ala Val Thr Leu Ala His Glu
    210                 215                 220

Leu Ile His Ala Gly His Arg Leu Tyr Gly Ile Ala Ile Asn Pro Asn
225                 230                 235                 240

Arg Val Phe Lys Val Asn Thr Asn Ala Tyr Tyr Glu Met Ser Gly Leu
                245                 250                 255

Glu Val Ser Phe Glu Glu Leu Arg Thr Phe Gly Gly His Asp Ala Lys
            260                 265                 270
```

```
Phe Ile Asp Ser Leu Gln Glu Asn Glu Phe Arg Leu Tyr Tyr Asn
            275                 280                 285
Lys Phe Lys Asp Ile Ala Ser Thr Leu Asn Lys Ala Lys Ser Ile Val
290                 295                 300
Gly Thr Thr Ala Ser Leu Gln Tyr Met Lys Asn Val Phe Lys Glu Lys
305                 310                 315                 320
Tyr Leu Leu Ser Glu Asp Thr Ser Gly Lys Phe Ser Val Asp Lys Leu
                325                 330                 335
Lys Phe Asp Lys Leu Tyr Lys Met Leu Thr Glu Ile Tyr Thr Glu Asp
            340                 345                 350
Asn Phe Val Lys Phe Phe Lys Val Leu Asn Arg Lys Thr Tyr Leu Asn
            355                 360                 365
Phe Asp Lys Ala Val Phe Lys Ile Asn Ile Val Pro Lys Val Asn Tyr
            370                 375                 380
Thr Ile Tyr Asp Gly Phe Asn Leu Arg Asn Thr Asn Leu Ala Ala Asn
385                 390                 395                 400
Phe Asn Gly Gln Asn Thr Glu Ile Asn Asn Met Asn Phe Thr Lys Leu
                405                 410                 415
Lys Asn Phe Thr Gly Leu Phe Glu Phe Tyr Lys Leu Leu Cys Val Arg
            420                 425                 430
Gly Ile Ile Thr Ser Lys Thr Lys Ser Leu Asp Lys Gly Tyr Asn Lys
            435                 440                 445
Ala Leu Asn Asp Leu Cys Ile Lys Val Asn Asn Trp Asp Leu Phe Phe
            450                 455                 460
Ser Pro Ser Glu Asp Asn Phe Thr Asn Asp Leu Asn Lys Gly Glu Glu
465                 470                 475                 480
Ile Thr Ser Asp Thr Asn Ile Glu Ala Ala Glu Glu Asn Ile Ser Leu
                485                 490                 495
Asp Leu Ile Gln Gln Tyr Tyr Leu Thr Phe Asn Phe Asp Asn Glu Pro
                500                 505                 510
Glu Asn Ile Ser Ile Glu Asn Leu Ser Ser Asp Ile Ile Gly Gln Leu
            515                 520                 525
Glu Leu Met Pro Asn Ile Glu Arg Phe Pro Asn Gly Lys Lys Tyr Glu
            530                 535                 540
Leu Asp Lys Tyr Thr Met Phe His Tyr Leu Arg Ala Gln Glu Phe Glu
545                 550                 555                 560
His Gly Lys Ser Arg Ile Ala Leu Thr Asn Ser Val Asn Glu Ala Leu
                565                 570                 575
Leu Asn Pro Ser Arg Val Tyr Thr Phe Phe Ser Ser Asp Tyr Val Lys
            580                 585                 590
Lys Val Asn Lys Ala Thr Glu Ala Ala Met Phe Leu Gly Trp Val Glu
            595                 600                 605
Gln Leu Val Tyr Asp Phe Thr Asp Glu Thr Ser Glu Val Ser Thr Thr
            610                 615                 620
Asp Lys Ile Ala Asp Ile Thr Ile Ile Pro Tyr Ile Gly Pro Ala
625                 630                 635                 640
Leu Asn Ile Gly Asn Met Leu Tyr Lys Asp Asp Phe Val Gly Ala Leu
                645                 650                 655
Ile Phe Ser Gly Ala Val Ile Leu Leu Glu Phe Ile Pro Glu Ile Ala
            660                 665                 670
Ile Pro Val Leu Gly Thr Phe Ala Leu Val Ser Tyr Ile Ala Asn Lys
            675                 680                 685
Val Leu Thr Val Gln Thr Ile Asp Asn Ala Leu Ser Lys Arg Asn Glu
```

```
                690             695             700
Lys Trp Asp Glu Val Tyr Lys Tyr Ile Val Thr Asn Trp Leu Ala Lys
705             710             715             720

Val Asn Thr Gln Ile Asp Leu Ile Arg Lys Met Lys Glu Ala Leu
            725             730             735

Glu Asn Gln Ala Glu Ala Thr Lys Ala Ile Ile Asn Tyr Gln Tyr Asn
            740             745             750

Gln Tyr Thr Glu Glu Lys Asn Asn Ile Asn Phe Asn Ile Asp Asp
            755             760             765

Leu Ser Ser Lys Leu Asn Glu Ser Ile Asn Lys Ala Met Ile Asn Ile
        770             775             780

Asn Lys Phe Leu Asn Gln Cys Ser Val Ser Tyr Leu Met Asn Ser Met
785             790             795             800

Ile Pro Tyr Gly Val Lys Arg Leu Glu Asp Phe Asp Ala Ser Leu Lys
            805             810             815

Asp Ala Leu Leu Lys Tyr Ile Tyr Asp Asn Arg Gly Thr Leu Ile Gly
            820             825             830

Gln Val Asp Arg Leu Lys Asp Lys Val Asn Asn Thr Leu Ser Thr Asp
            835             840             845

Ile Pro Phe Gln Leu Ser Lys Tyr Val Asp Asn Gln Arg Leu Leu Ser
850             855             860

Thr Phe Thr Glu Tyr Ile Lys Asn Ile Ile Asn Thr Ser Ile Leu Asn
865             870             875             880

Leu Arg Tyr Glu Ser Asn His Leu Ile Asp Leu Ser Arg Tyr Ala Ser
            885             890             895

Lys Ile Asn Ile Gly Ser Lys Val Asn Phe Asp Pro Ile Asp Lys Asn
            900             905             910

Gln Ile Gln Leu Phe Asn Leu Glu Ser Ser Lys Ile Glu Val Ile Leu
            915             920             925

Lys Asn Ala Ile Val Tyr Asn Ser Met Tyr Glu Asn Phe Ser Thr Ser
930             935             940

Phe Trp Ile Arg Ile Pro Lys Tyr Phe Asn Ser Ile Ser Leu Asn Asn
945             950             955             960

Glu Tyr Thr Ile Ile Asn Cys Met Glu Asn Asn Ser Gly Trp Lys Val
            965             970             975

Ser Leu Asn Tyr Gly Glu Ile Ile Trp Thr Leu Gln Asp Thr Gln Glu
            980             985             990

Ile Lys Gln Arg Val Val Phe Lys Tyr Ser Gln Met Ile Asn Ile Ser
            995             1000            1005

Asp Tyr Ile Asn Arg Trp Ile Phe Val Thr Ile Thr Asn Asn Arg
    1010            1015            1020

Leu Asn Asn Ser Lys Ile Tyr Ile Asn Gly Arg Leu Ile Asp Gln
    1025            1030            1035

Lys Pro Ile Ser Asn Leu Gly Asn Ile His Ala Ser Asn Asn Ile
    1040            1045            1050

Met Phe Lys Leu Asp Gly Cys Arg Asp Thr His Arg Tyr Ile Trp
    1055            1060            1065

Ile Lys Tyr Phe Asn Leu Phe Asp Lys Glu Leu Asn Glu Lys Glu
    1070            1075            1080

Ile Lys Asp Leu Tyr Asp Asn Gln Ser Asn Ser Gly Ile Leu Lys
    1085            1090            1095

Asp Phe Trp Gly Asp Tyr Leu Gln Tyr Asp Lys Pro Tyr Tyr Met
    1100            1105            1110
```

| | | | | | | | | | | |
|---|---|---|---|---|---|---|---|---|---|---|
|Leu|Asn|Leu|Tyr|Asp|Pro|Asn|Lys|Tyr|Val|Asp Val Asn Asn Val|
|1115| | | |1120| | | |1125| | |
|Gly|Ile|Arg|Gly|Tyr|Met|Tyr|Leu|Lys|Gly|Pro Arg Gly Ser Val|
|1130| | | |1135| | | |1140| | |
|Met|Thr|Thr|Asn|Ile|Tyr|Leu|Asn|Ser|Ser|Leu Tyr Arg Gly Thr|
|1145| | | |1150| | | |1155| | |
|Lys|Phe|Ile|Ile|Lys|Lys|Tyr|Ala|Ser|Gly|Asn Lys Asp Asn Ile|
|1160| | | |1165| | | |1170| | |
|Val|Arg|Asn|Asn|Asp|Arg|Val|Tyr|Ile|Asn|Val Val Lys Asn|
|1175| | | |1180| | | |1185| | |
|Lys|Glu|Tyr|Arg|Leu|Ala|Thr|Asn|Ala|Ser|Gln Ala Gly Val Glu|
|1190| | | |1195| | | |1200| | |
|Lys|Ile|Leu|Ser|Ala|Leu|Glu|Ile|Pro|Asp|Val Gly Asn Leu Ser|
|1205| | | |1210| | | |1215| | |
|Gln|Val|Val|Val|Met|Lys|Ser|Lys|Asn|Asp|Gln Gly Ile Thr Asn|
|1220| | | |1225| | | |1230| | |
|Lys|Cys|Lys|Met|Asn|Leu|Gln|Asp|Asn|Gly|Asn Asp Ile Gly|
|1235| | | |1240| | | |1245| | |
|Phe|Ile|Gly|Phe|His|Gln|Phe|Asn|Asn|Ile|Ala Lys Leu Val Ala|
|1250| | | |1255| | | |1260| | |
|Ser|Asn|Trp|Tyr|Asn|Arg|Gln|Ile|Glu|Arg|Ser Ser Arg Thr Leu|
|1265| | | |1270| | | |1275| | |
|Gly|Cys|Ser|Trp|Glu|Phe|Ile|Pro|Val|Asp|Asp Gly Trp Gly Glu|
|1280| | | |1285| | | |1290| | |
|Arg|Pro|Leu| | | | | | | | |
|1295| | | | | | | | | | |

```
<210> SEQ ID NO 3
<211> LENGTH: 3876
<212> TYPE: DNA
<213> ORGANISM: Clostridium botulinum

<400> SEQUENCE: 3
atgccagtta caataaataa ttttaattat aatgatccta ttgataataa taatattatt      60
atgatggagc ctccatttgc gagaggtacg gggagatatt ataaagcttt taaaatcaca     120
gatcgtattt ggataatacc ggaaagatat acttttggat ataaacctga ggattttaat     180
aaaagttccg gtattttta tagagatgtt tgtgaatatt atgatccaga ttacttaaat     240
actaatgata aaagaatat attttacaa acaatgatca agttattaa tagaatcaaa       300
tcaaaaccat tgggtgaaaa gttattagag atgattataa atggtatacc ttatcttgga    360
gatagacgtg ttccactcga agagtttaac acaaacattg ctagtgtaac tgttaataaa    420
ttaatcagta atccaggaga agtggagcga aaaaaaggta ttttcgcaaa tttaataata    480
tttgacctg gccagtttt aaatgaaaat gagactatag ataggtat acaaaatcat        540
tttgcatcaa gggaaggctt cggggggtata atgcaaatga gttttgccc agaatatgta    600
agcgtattta taatgttca agaaaacaaa ggcgcaagta tatttaatag acgtggatat    660
ttttcagatc cagccttgat attaatgcat gaacttatac atgttttaca tggattatat    720
ggcattaaag tagatgattt accaattgta ccaatgaaa aaaattttt tatgcaatct     780
acagatgcta tacaggcaga agaactatat acatttggag acaagatcc cagcatcata    840
actccttcta cggataaaag tatctatgat aaagttttgc aaaattttag agggatagtt    900
gatagactta acaaggtttt agtttgcata tcagatccta acattaatat aatatatat    960
```

```
aaaaataaat ttaaagataa atataaattc gttgaagatt ctgagggaaa atatagtata    1020
gatgtagaaa gttttgataa attatataaa agcttaatgt ttggttttac agaaactaat    1080
atagcagaaa attataaaat aaaaactaga gcttcttatt ttagtgattc cttaccacca    1140
gtaaaaataa aaaatttatt agataatgaa atctatacta tagaggaagg gtttaatata    1200
tctgataaag atatggaaaa agaatataga ggtcagaata aagctataaa taaacaagct    1260
tatgaagaaa ttagcaagga gcatttggct gtatataaga tacaaatgtg taaaagtgtt    1320
aaagctccag gaatatgtat tgatgttgat aatgaagatt tgttctttat agctgataaa    1380
aatagttttt cagatgattt atctaaaaac gaaagaatag aatataatac acagagtaat    1440
tatatagaaa atgacttccc tataaatgaa ttaattttag atactgattt aataagtaaa    1500
atagaattac caagtgaaaa tacagaatca cttactgatt ttaatgtaga tgttccagta    1560
tatgaaaaac aacccgctat aaaaaaaatt tttacagatg aaaataccat ctttcaatat    1620
ttatactctc agacatttcc tctagatata agagatataa gtttaacatc ttcatttgat    1680
gatgcattat tattttctaa caaagtttat tcattttttt ctatggatta tattaaaact    1740
gctaataaag tggtagaagc aggattattt gcaggttggg tgaaacagat agtaaatgat    1800
tttgtaatcg aagctaataa aagcaatact atggataaaa ttgcagatat atctctaatt    1860
gttccttata taggattagc tttaaatgta ggaaatgaaa cagctaaagg aaattttgaa    1920
aatgcttttg agattgcagg agccagtatt ctactagaat ttataccaga acttttaata    1980
cctgtagttg gagccttttt attagaatca tatattgaca ataaaaataa aattattaaa    2040
acaatagata atgctttaac taaaagaaat gaaaaatgga gtgatatgta cggattaata    2100
gtagcgcaat ggctctcaac agttaatact caattttata caataaaaga gggaatgtat    2160
aaggctttaa attatcaagc acaagcattg gaagaaataa taaaatacag atataatata    2220
tattctgaaa aagaaaagtc aaatattaac atcgatttta atgatataaa ttctaaactt    2280
aatgagggta ttaaccaagc tatagataat ataaataatt ttataaatgg atgttctgta    2340
tcatatttaa tgaaaaaaat gattccatta gctgtagaaa aattactaga ctttgataat    2400
actctcaaaa aaaatttgtt aaattatata gatgaaaata aattatattt gattggaagt    2460
gcagaatatg aaaaatcaaa agtaaataaa tacttgaaaa ccattatgcc gtttgatctt    2520
tcaatatata ccaatgatac aatactaata gaaatgttta taaatataa tagcgaaatt    2580 ttaaataata ttatcttaaa tttaagatat aaggataata atttaataga tttatcagga    2640
tatggggcaa aggtagaggt atatgatgga gtcgagctta atgataaaaa tcaatttaaa    2700
ttaactagtt cagcaaatag taagattaga gtgactcaaa atcagaatat catatttaat    2760
agtgtgttcc ttgattttag cgttagcttt tggataagaa tacctaaata taagaatgat    2820
ggtatacaaa attatattca taatgaatat acaataatta attgtatgaa aaataattcg    2880
ggctggaaaa tatctattag gggtaatagg ataaatggga cttttaattga tataaatgga    2940 aaaaccaaat cggtattttt tgaatataac ataagagaag atatatcaga gtatataaat    3000
agatggtttt ttgtaactat tactaataat ttgaataacg ctaaaattta tattaatggt    3060
aagctagaat caaatacaga tattaaagat ataagagaag ttattgctaa tggtgaaata    3120
atatttaaat tagatggtga tatagataga acacaattta tttggatgaa atatttcagt    3180
atttttaata cggaattaag tcaatcaaat attgaagaaa gatataaaat tcaatcatat    3240
agcgaatatt taaaagattt ttggggaaat cctttaatgt acaataaaga atattatatg    3300
```

-continued

```
tttaatgcgg ggaataaaaa ttcatatatt aaactaaaga aagattcacc tgtaggtgaa    3360
attttaacac gtagcaaata taatcaaaat tctaaatata taaattatag agatttatat    3420
attggagaaa aatttattat aagaagaaag tcaaattctc aatctataaa tgatgatata    3480
gttagaaaag aagattatat atatctagat tttttttaatt taaatcaaga gtggagagta    3540
```
(note: line 3540 is reproduced as printed)

```
gttagaaaag aagattatat atatctagat tttttttaatt taaatcaaga gtggagagta    3540
tatacctata aatattttaa gaaagaggaa gaaaaattgt ttttagctcc tataagtgat    3600
tctgatgagt ttacaatac tatacaaata aaagaatatg atgaacagcc aacatatagt    3660
tgtcagttgc tttttaaaaa agatgaagaa agtactgatg agatagggat gattggtatt    3720
catcgtttct acgaatctgg aattgtattt gaagagtata aagattattt ttgtataagt    3780
aaatggtact taaagagggt aaaaaggaaa ccatataatt taaaattggg atgtaattgg    3840 cagттттaттc ctaaagatga agggtggact gaataa                             3876
```

<210> SEQ ID NO 4
<211> LENGTH: 1291
<212> TYPE: PRT
<213> ORGANISM: Clostridium botulinum

<400> SEQUENCE: 4

```
Met Pro Val Thr Ile Asn Asn Phe Asn Tyr Asn Asp Pro Ile Asp Asn
1               5                   10                  15

Asn Asn Ile Ile Met Met Glu Pro Pro Phe Ala Arg Gly Thr Gly Arg
            20                  25                  30

Tyr Tyr Lys Ala Phe Lys Ile Thr Asp Arg Ile Trp Ile Ile Pro Glu
        35                  40                  45

Arg Tyr Thr Phe Gly Tyr Lys Pro Glu Asp Phe Asn Lys Ser Ser Gly
    50                  55                  60

Ile Phe Asn Arg Asp Val Cys Glu Tyr Tyr Asp Pro Asp Tyr Leu Asn
65                  70                  75                  80

Thr Asn Asp Lys Lys Asn Ile Phe Leu Gln Thr Met Ile Lys Leu Phe
                85                  90                  95

Asn Arg Ile Lys Ser Lys Pro Leu Gly Glu Lys Leu Leu Glu Met Ile
            100                 105                 110

Ile Asn Gly Ile Pro Tyr Leu Gly Asp Arg Arg Val Pro Leu Glu Glu
        115                 120                 125

Phe Asn Thr Asn Ile Ala Ser Val Thr Val Asn Lys Leu Ile Ser Asn
    130                 135                 140

Pro Gly Glu Val Glu Arg Lys Lys Gly Ile Phe Ala Asn Leu Ile Ile
145                 150                 155                 160

Phe Gly Pro Gly Pro Val Leu Asn Glu Asn Glu Thr Ile Asp Ile Gly
                165                 170                 175

Ile Gln Asn His Phe Ala Ser Arg Glu Gly Phe Gly Gly Ile Met Gln
            180                 185                 190

Met Lys Phe Cys Pro Glu Tyr Val Ser Val Phe Asn Asn Val Gln Glu
        195                 200                 205

Asn Lys Gly Ala Ser Ile Phe Asn Arg Arg Gly Tyr Phe Ser Asp Pro
    210                 215                 220

Ala Leu Ile Leu Met His Glu Leu Ile His Val Leu His Gly Leu Tyr
225                 230                 235                 240

Gly Ile Lys Val Asp Asp Leu Pro Ile Val Pro Asn Glu Lys Lys Phe
                245                 250                 255

Phe Met Gln Ser Thr Asp Ala Ile Gln Ala Glu Glu Leu Tyr Thr Phe
            260                 265                 270
```

-continued

Gly Gly Gln Asp Pro Ser Ile Ile Thr Pro Ser Thr Asp Lys Ser Ile
            275                 280                 285
Tyr Asp Lys Val Leu Gln Asn Phe Arg Gly Ile Val Asp Arg Leu Asn
290                 295                 300
Lys Val Leu Val Cys Ile Ser Asp Pro Asn Ile Asn Ile Asn Ile Tyr
305                 310                 315                 320
Lys Asn Lys Phe Lys Asp Lys Tyr Lys Phe Val Glu Asp Ser Glu Gly
                325                 330                 335
Lys Tyr Ser Ile Asp Val Glu Ser Phe Asp Lys Leu Tyr Lys Ser Leu
            340                 345                 350
Met Phe Gly Phe Thr Glu Thr Asn Ile Ala Glu Asn Tyr Lys Ile Lys
        355                 360                 365
Thr Arg Ala Ser Tyr Phe Ser Asp Ser Leu Pro Pro Val Lys Ile Lys
370                 375                 380
Asn Leu Leu Asp Asn Glu Ile Tyr Thr Ile Glu Glu Gly Phe Asn Ile
385                 390                 395                 400
Ser Asp Lys Asp Met Glu Lys Glu Tyr Arg Gly Gln Asn Lys Ala Ile
                405                 410                 415
Asn Lys Gln Ala Tyr Glu Glu Ile Ser Lys Glu His Leu Ala Val Tyr
            420                 425                 430
Lys Ile Gln Met Cys Lys Ser Val Lys Ala Pro Gly Ile Cys Ile Asp
        435                 440                 445
Val Asp Asn Glu Asp Leu Phe Phe Ile Ala Asp Lys Asn Ser Phe Ser
    450                 455                 460
Asp Asp Leu Ser Lys Asn Glu Arg Ile Glu Tyr Asn Thr Gln Ser Asn
465                 470                 475                 480
Tyr Ile Glu Asn Asp Phe Pro Ile Asn Glu Leu Ile Leu Asp Thr Asp
                485                 490                 495
Leu Ile Ser Lys Ile Glu Leu Pro Ser Glu Asn Thr Glu Ser Leu Thr
            500                 505                 510
Asp Phe Asn Val Asp Val Pro Val Tyr Glu Lys Gln Pro Ala Ile Lys
        515                 520                 525
Lys Ile Phe Thr Asp Glu Asn Thr Ile Phe Gln Tyr Leu Tyr Ser Gln
530                 535                 540
Thr Phe Pro Leu Asp Ile Arg Asp Ile Ser Leu Thr Ser Ser Phe Asp
545                 550                 555                 560
Asp Ala Leu Leu Phe Ser Asn Lys Val Tyr Ser Phe Phe Ser Met Asp
                565                 570                 575
Tyr Ile Lys Thr Ala Asn Lys Val Val Glu Ala Gly Leu Phe Ala Gly
            580                 585                 590
Trp Val Lys Gln Ile Val Asn Asp Phe Val Ile Glu Ala Asn Lys Ser
        595                 600                 605
Asn Thr Met Asp Lys Ile Ala Asp Ile Ser Leu Ile Val Pro Tyr Ile
610                 615                 620
Gly Leu Ala Leu Asn Val Gly Asn Glu Thr Ala Lys Gly Asn Phe Glu
625                 630                 635                 640
Asn Ala Phe Glu Ile Ala Gly Ala Ser Ile Leu Leu Glu Phe Ile Pro
                645                 650                 655
Glu Leu Leu Ile Pro Val Val Gly Ala Phe Leu Leu Glu Ser Tyr Ile
            660                 665                 670
Asp Asn Lys Asn Lys Ile Ile Lys Thr Ile Asp Asn Ala Leu Thr Lys
        675                 680                 685
Arg Asn Glu Lys Trp Ser Asp Met Tyr Gly Leu Ile Val Ala Gln Trp

```
            690             695             700
Leu Ser Thr Val Asn Thr Gln Phe Tyr Thr Ile Lys Glu Gly Met Tyr
705                 710             715                 720

Lys Ala Leu Asn Tyr Gln Ala Gln Ala Leu Glu Glu Ile Ile Lys Tyr
                725             730              735

Arg Tyr Asn Ile Tyr Ser Glu Lys Glu Lys Ser Asn Ile Asn Ile Asp
                740             745             750

Phe Asn Asp Ile Asn Ser Lys Leu Asn Glu Gly Ile Asn Gln Ala Ile
            755             760             765

Asp Asn Ile Asn Asn Phe Ile Asn Gly Cys Ser Val Ser Tyr Leu Met
            770             775             780

Lys Lys Met Ile Pro Leu Ala Val Glu Lys Leu Leu Asp Phe Asp Asn
785             790             795             800

Thr Leu Lys Lys Asn Leu Leu Asn Tyr Ile Asp Glu Asn Lys Leu Tyr
                805             810             815

Leu Ile Gly Ser Ala Glu Tyr Glu Lys Ser Lys Val Asn Lys Tyr Leu
                820             825             830

Lys Thr Ile Met Pro Phe Asp Leu Ser Ile Tyr Thr Asn Asp Thr Ile
                835             840             845

Leu Ile Glu Met Phe Asn Lys Tyr Asn Ser Glu Ile Leu Asn Asn Ile
850             855             860

Ile Leu Asn Leu Arg Tyr Lys Asp Asn Asn Leu Ile Asp Leu Ser Gly
865             870             875             880

Tyr Gly Ala Lys Val Glu Val Tyr Asp Gly Val Glu Leu Asn Asp Lys
                885             890             895

Asn Gln Phe Lys Leu Thr Ser Ser Ala Asn Ser Lys Ile Arg Val Thr
                900             905             910

Gln Asn Gln Asn Ile Ile Phe Asn Ser Val Phe Leu Asp Phe Ser Val
                915             920             925

Ser Phe Trp Ile Arg Ile Pro Lys Tyr Lys Asn Asp Gly Ile Gln Asn
                930             935             940

Tyr Ile His Asn Glu Tyr Thr Ile Ile Asn Cys Met Lys Asn Asn Ser
945             950             955             960

Gly Trp Lys Ile Ser Ile Arg Gly Asn Arg Ile Ile Trp Thr Leu Ile
                965             970             975

Asp Ile Asn Gly Lys Thr Lys Ser Val Phe Phe Glu Tyr Asn Ile Arg
                980             985             990

Glu Asp Ile Ser Glu Tyr Ile Asn Arg Trp Phe Phe Val Thr Ile Thr
                995             1000            1005

Asn Asn Leu Asn Asn Ala Lys Ile Tyr Ile Asn Gly Lys Leu Glu
        1010            1015            1020

Ser Asn Thr Asp Ile Lys Asp Ile Arg Glu Val Ile Ala Asn Gly
        1025            1030            1035

Glu Ile Ile Phe Lys Leu Asp Gly Asp Ile Asp Arg Thr Gln Phe
        1040            1045            1050

Ile Trp Met Lys Tyr Phe Ser Ile Phe Asn Thr Glu Leu Ser Gln
        1055            1060            1065

Ser Asn Ile Glu Glu Arg Tyr Lys Ile Gln Ser Tyr Ser Glu Tyr
        1070            1075            1080

Leu Lys Asp Phe Trp Gly Asn Pro Leu Met Tyr Asn Lys Glu Tyr
        1085            1090            1095

Tyr Met Phe Asn Ala Gly Asn Lys Asn Ser Tyr Ile Lys Leu Lys
        1100            1105            1110
```

```
Lys Asp Ser Pro Val Gly Glu Ile Leu Thr Arg Ser Lys Tyr Asn
1115                1120                1125

Gln Asn Ser Lys Tyr Ile Asn Tyr Arg Asp Leu Tyr Ile Gly Glu
1130                1135                1140

Lys Phe Ile Ile Arg Arg Lys Ser Asn Ser Gln Ser Ile Asn Asp
1145                1150                1155

Asp Ile Val Arg Lys Glu Asp Tyr Ile Tyr Leu Asp Phe Phe Asn
1160                1165                1170

Leu Asn Gln Glu Trp Arg Val Tyr Thr Tyr Lys Tyr Phe Lys Lys
1175                1180                1185

Glu Glu Glu Lys Leu Phe Leu Ala Pro Ile Ser Asp Ser Asp Glu
1190                1195                1200

Phe Tyr Asn Thr Ile Gln Ile Lys Glu Tyr Asp Glu Gln Pro Thr
1205                1210                1215

Tyr Ser Cys Gln Leu Leu Phe Lys Lys Asp Glu Glu Ser Thr Asp
1220                1225                1230

Glu Ile Gly Leu Ile Gly Ile His Arg Phe Tyr Glu Ser Gly Ile
1235                1240                1245

Val Phe Glu Glu Tyr Lys Asp Tyr Phe Cys Ile Ser Lys Trp Tyr
1250                1255                1260

Leu Lys Glu Val Lys Arg Lys Pro Tyr Asn Leu Lys Leu Gly Cys
1265                1270                1275

Asn Trp Gln Phe Ile Pro Lys Asp Glu Gly Trp Thr Glu
1280                1285                1290

<210> SEQ ID NO 5
<211> LENGTH: 3843
<212> TYPE: DNA
<213> ORGANISM: Clostridium botulinum

<400> SEQUENCE: 5
atgccaataa caattaacaa cttttaattat tcagatcctg ttgataataa aaatatttta     60
tatttagata ctcatttaaa tacattagct aatgagcctg aaaaagcctt tcgcattata    120
gggaatatat gggtaatacc cgatagattt tcaagagatt ctaatccaaa tttaaataaa    180
cctcctcgag ttacaagccc taaaagtggt tattatgatc ctaattattt gagtactgat    240
tctgaaaaag tacattttt aaaagaaatt ataaagttat ttaaagaat taactctaga    300 gaaataggag aagaattaat atatagactt gcaacagaca taccctttcc tgggaataac    360
aatactccaa ttaatacttt tgattttgat gtagatttta acagtgttga tgttaaaact    420
agacaaggta caactgggt taaaactggt agtataaatc ctagtgttat aataactgga    480
cctagagaaa acattataga cccagaaact tctacgttta aattaactaa caatactttt    540
gcggcacaag aaggatttgg tgctttatca ataatttcaa tatcacctag atttatgcta    600
acatatagta tgcaactaa taatgtagga gagggtagat tttctaagtc tgaattttgc    660
atggatccaa tactaatttt aatgcatgaa cttaatcatg caatgcataa tttatatgga    720
atagctatac caaatgatca aagaatttca tctgtaacta gtaatatttt ttattctcaa    780
tataaggtga aattagagta tgcagaaata tatgcatttg gaggtccaac tatagacctt    840
attcctaaaa gtgcaaggaa atattttgag gaaaaggcat ggattatta tagatccata    900 gctaaaagac ttaatagtat aactactgca aatccttcaa gctttaataa atatatagga    960
gaatataaac agaaacttat tagaaagtat agattcgtag tagaatcttc aggtgaagtt   1020
```

```
gcagtagatc gtaataagtt tgctgagtta tataaagaac ttacacaaat atttacagaa      1080
tttaactacg ctaaaatata taatgtacaa aataggaaaa tatatctttc aaatgtatat      1140
actccggtta cggcaaatat attagacgat aatgtttatg atatacaaaa tggatttaac      1200
atacctaaaa gtaatttaaa tgtactattt atgggtcaaa atttatctcg aaatccagca      1260
ttaagaaaag tcaatcctga aaatatgctt tatttattta caaaattttg ccataaagca      1320
atagatggta gatcattata taataaaaca ttagattgta gagagctttt agttaaaaat      1380
actgacttac cctttatagg tgatattagt gatatcaaaa ctgatatatt tttaagcaaa      1440
gatattaatg aagaaactga agttatagac tatccggaca atgtttcagt ggatcaagtt      1500
attctcagta agaatacctc agaacatgga caactagatt tattataccc tattattgaa      1560
ggtgagagtc aagtattacc gggagagaat caagtctttt atgataatag aactcaaaat      1620
gttgattatt tgaattctta ttattaccta gaatctcaaa aactaagtga taatgttgaa      1680
gattttactt ttacgacatc aattgaggaa gctttggata atagtggaaa agtatatact      1740
tactttccta aactagctga taaagtaaat acgggtgttc aaggtggttt atttttaatg      1800
tgggcaaatg atgtagttga agattttact acaaatattc taagaaaaga tacattagat      1860
aaaatatcag atgtatcagc tattattccc tatataggac ctgcattaaa tataagtaat      1920
tctgtaagaa ggggaaattt tactgaagca tttgcagtta ccggtgtaac tattttatta      1980
gaagcgtttc aagaatttac aatacctgca cttggtgcat ttgtgattta tagtaaggtt      2040
caagaaagaa acgagattat taaaactata gataattgtt tagaacaaag gattaaaaga      2100
tggaaagatt catatgaatg gatgatagga acgtggttat ccaggattac tactcaattt      2160
aataatataa gttatcaaat gtatgattct ttaaattatc aggcagatgc aatcaaagat      2220
aaaatagatt tagaatataa aaaatactca ggaagtgata agaaaaatat aaaaagtcaa      2280
gttgaaaatt taaaaaatag tttagatata aaaatctcgg aagcaatgaa taatataaat      2340
aaatttatac gagaatgttc tgtaacatac ttatttaaaa atatgctccc taagtaatt      2400 gatgaattaa ataagtttga tttaaaaact aaaacagaat taattaatct tatagatagt      2460
cataatatta ttctagttgg tgaagtagat agattaaaag caaaagtaaa tgagagtttt      2520
gaaaatacaa tacccttaa tatttttca tatactaata attctttatt aaaagatata      2580
attaatgaat atttcaatag tattaatgat tcaaaatttt tgagcttaca aaacaaaaaa      2640
aatgctttag tggatacatc aggatataat gcagaagtga ggctagaagg tgatgttcaa      2700
gttaatacga tatatacaaa tgattttaaa ttaagtagtt caggagataa aattatagta      2760
aatttaaata ataatatttt atatagcgct atttatgaga actctagtgt tagttttttgg      2820 attaagatat ctaaagattt aactaattct cataatgaat atacaataat taatagtata      2880
aaacaaaatt ctgggtggaa attatgtatt aggaatggca atatagaatg gatttttacaa      2940 gatattaata gaaagtataa agtttaatt tttgattata gtgaatcatt aagtcataca      3000
ggatatacaa ataaatggtt ttttgttact ataactaata atataatggg gtatatgaaa      3060
ctttatataa atggagaatt aaagcagagt gaaagaattg aagatttaaa tgaggttaag      3120
ttagataaaa ccatagtatt tggaatagat gagaatatag atgagaatca gatgctttgg      3180
attagagatt ttaatatttt ttctaaagaa ttaagcaatg aagatattaa tattgtatat      3240
gagggacaaa tattaagaaa tgttattaaa gattattggg gaaatccttt gaagtttgat      3300
acagaatatt atattattaa tgataattat atagatagt atatagcacc taaaagtaat      3360
atacttgtac ttgttcagta tccagataga tctaaattat atactggaaa tcctattact      3420
```

```
attaaatcag tatctgataa gaatccttat agtagaattt taaatggaga taatataatg      3480
tttcatatgt tatataatag tgggaaatat atgataataa gagatactga tacaatatat      3540
gcaatagaag gaagagagtg ttcaaaaaat tgtgtatatg cattaaaatt acagagtaat      3600
ttaggtaatt atggtatagg tatatttagt ataaaaaata ttgtatctca aaataaaatat     3660 tgtagtcaaa ttttctctag ttttatgaaa aatacaatgc ttctagcaga tatatataaa      3720
ccttggagat tttcttttga aaatgcatac acgccagttg cagtaactaa ttatgagaca      3780
aaactattat caacttcatc tttttggaaa tttatttcta gggatccagg atgggtagag      3840
taa                                                                    3843

<210> SEQ ID NO 6
<211> LENGTH: 1280
<212> TYPE: PRT
<213> ORGANISM: Clostridium botulinum

<400> SEQUENCE: 6

Met Pro Ile Thr Ile Asn Asn Phe Asn Tyr Ser Asp Pro Val Asp Asn
1               5                   10                  15

Lys Asn Ile Leu Tyr Leu Asp Thr His Leu Asn Thr Leu Ala Asn Glu
            20                  25                  30

Pro Glu Lys Ala Phe Arg Ile Ile Gly Asn Ile Trp Val Ile Pro Asp
        35                  40                  45

Arg Phe Ser Arg Asp Ser Asn Pro Asn Leu Asn Lys Pro Pro Arg Val
    50                  55                  60

Thr Ser Pro Lys Ser Gly Tyr Tyr Asp Pro Asn Tyr Leu Ser Thr Asp
65                  70                  75                  80

Ser Glu Lys Asp Thr Phe Leu Lys Glu Ile Ile Lys Leu Phe Lys Arg
                85                  90                  95

Ile Asn Ser Arg Glu Ile Gly Glu Glu Leu Ile Tyr Arg Leu Ala Thr
            100                 105                 110

Asp Ile Pro Phe Pro Gly Asn Asn Asn Thr Pro Ile Asn Thr Phe Asp
        115                 120                 125

Phe Asp Val Asp Phe Asn Ser Val Asp Val Lys Thr Arg Gln Gly Asn
    130                 135                 140

Asn Trp Val Lys Thr Gly Ser Ile Asn Pro Ser Val Ile Ile Thr Gly
145                 150                 155                 160

Pro Arg Glu Asn Ile Ile Asp Pro Glu Thr Ser Thr Phe Lys Leu Thr
                165                 170                 175

Asn Asn Thr Phe Ala Ala Gln Glu Gly Phe Gly Ala Leu Ser Ile Ile
            180                 185                 190

Ser Ile Ser Pro Arg Phe Met Leu Thr Tyr Ser Asn Ala Thr Asn Asn
        195                 200                 205

Val Gly Glu Gly Arg Phe Ser Lys Ser Glu Phe Cys Met Asp Pro Ile
    210                 215                 220

Leu Ile Leu Met His Glu Leu Asn His Ala Met His Asn Leu Tyr Gly
225                 230                 235                 240

Ile Ala Ile Pro Asn Asp Gln Arg Ile Ser Ser Val Thr Ser Asn Ile
                245                 250                 255

Phe Tyr Ser Gln Tyr Lys Val Lys Leu Glu Tyr Ala Glu Ile Tyr Ala
            260                 265                 270

Phe Gly Gly Pro Thr Ile Asp Leu Ile Pro Lys Ser Ala Arg Lys Tyr
        275                 280                 285
```

```
Phe Glu Glu Lys Ala Leu Asp Tyr Tyr Arg Ser Ile Ala Lys Arg Leu
    290                 295                 300

Asn Ser Ile Thr Thr Ala Asn Pro Ser Ser Phe Asn Lys Tyr Ile Gly
305                 310                 315                 320

Glu Tyr Lys Gln Lys Leu Ile Arg Lys Tyr Arg Phe Val Val Glu Ser
                325                 330                 335

Ser Gly Glu Val Ala Val Asp Arg Asn Lys Phe Ala Glu Leu Tyr Lys
            340                 345                 350

Glu Leu Thr Gln Ile Phe Thr Glu Phe Asn Tyr Ala Lys Ile Tyr Asn
        355                 360                 365

Val Gln Asn Arg Lys Ile Tyr Leu Ser Asn Val Tyr Thr Pro Val Thr
370                 375                 380

Ala Asn Ile Leu Asp Asp Asn Val Tyr Asp Ile Gln Asn Gly Phe Asn
385                 390                 395                 400

Ile Pro Lys Ser Asn Leu Asn Val Leu Phe Met Gly Gln Asn Leu Ser
                405                 410                 415

Arg Asn Pro Ala Leu Arg Lys Val Asn Pro Glu Asn Met Leu Tyr Leu
            420                 425                 430

Phe Thr Lys Phe Cys His Lys Ala Ile Asp Gly Arg Ser Leu Tyr Asn
        435                 440                 445

Lys Thr Leu Asp Cys Arg Glu Leu Leu Val Lys Asn Thr Asp Leu Pro
450                 455                 460

Phe Ile Gly Asp Ile Ser Asp Ile Lys Thr Asp Ile Phe Leu Ser Lys
465                 470                 475                 480

Asp Ile Asn Glu Glu Thr Glu Val Ile Asp Tyr Pro Asp Asn Val Ser
                485                 490                 495

Val Asp Gln Val Ile Leu Ser Lys Asn Thr Ser Glu His Gly Gln Leu
            500                 505                 510

Asp Leu Leu Tyr Pro Ile Ile Glu Gly Glu Ser Gln Val Leu Pro Gly
        515                 520                 525

Glu Asn Gln Val Phe Tyr Asp Asn Arg Thr Gln Asn Val Asp Tyr Leu
530                 535                 540

Asn Ser Tyr Tyr Tyr Leu Glu Ser Gln Lys Leu Ser Asp Asn Val Glu
545                 550                 555                 560

Asp Phe Thr Phe Thr Thr Ser Ile Glu Glu Ala Leu Asp Asn Ser Gly
                565                 570                 575

Lys Val Tyr Thr Tyr Phe Pro Lys Leu Ala Asp Lys Val Asn Thr Gly
            580                 585                 590

Val Gln Gly Gly Leu Phe Leu Met Trp Ala Asn Asp Val Val Glu Asp
        595                 600                 605

Phe Thr Thr Asn Ile Leu Arg Lys Asp Thr Leu Asp Lys Ile Ser Asp
610                 615                 620

Val Ser Ala Ile Ile Pro Tyr Ile Gly Pro Ala Leu Asn Ile Ser Asn
625                 630                 635                 640

Ser Val Arg Arg Gly Asn Phe Thr Glu Ala Phe Ala Val Thr Gly Val
                645                 650                 655

Thr Ile Leu Leu Glu Ala Phe Gln Glu Phe Thr Ile Pro Ala Leu Gly
            660                 665                 670

Ala Phe Val Ile Tyr Ser Lys Val Gln Glu Arg Asn Glu Ile Ile Lys
        675                 680                 685

Thr Ile Asp Asn Cys Leu Glu Gln Arg Ile Lys Arg Trp Lys Asp Ser
690                 695                 700

Tyr Glu Trp Met Ile Gly Thr Trp Leu Ser Arg Ile Thr Thr Gln Phe
```

-continued

```
            705                 710                 715                 720
        Asn Asn Ile Ser Tyr Gln Met Tyr Asp Ser Leu Asn Tyr Gln Ala Asp
                        725                 730                 735
        Ala Ile Lys Asp Lys Ile Asp Leu Glu Tyr Lys Lys Tyr Ser Gly Ser
                        740                 745                 750
        Asp Lys Glu Asn Ile Lys Ser Gln Val Glu Asn Leu Lys Asn Ser Leu
                        755                 760                 765
        Asp Ile Lys Ile Ser Glu Ala Met Asn Asn Ile Asn Lys Phe Ile Arg
                        770                 775                 780
        Glu Cys Ser Val Thr Tyr Leu Phe Lys Asn Met Leu Pro Lys Val Ile
        785                 790                 795                 800
        Asp Glu Leu Asn Lys Phe Asp Leu Lys Thr Lys Thr Glu Leu Ile Asn
                        805                 810                 815
        Leu Ile Asp Ser His Asn Ile Ile Leu Val Gly Glu Val Asp Arg Leu
                        820                 825                 830
        Lys Ala Lys Val Asn Glu Ser Phe Glu Asn Thr Ile Pro Phe Asn Ile
                        835                 840                 845
        Phe Ser Tyr Thr Asn Asn Ser Leu Leu Lys Asp Ile Ile Asn Glu Tyr
                        850                 855                 860
        Phe Asn Ser Ile Asn Asp Ser Lys Ile Leu Ser Leu Gln Asn Lys Lys
        865                 870                 875                 880
        Asn Ala Leu Val Asp Thr Ser Gly Tyr Asn Ala Glu Val Arg Leu Glu
                        885                 890                 895
        Gly Asp Val Gln Val Asn Thr Ile Tyr Thr Asn Asp Phe Lys Leu Ser
                        900                 905                 910
        Ser Ser Gly Asp Lys Ile Ile Val Asn Leu Asn Asn Asn Ile Leu Tyr
                        915                 920                 925
        Ser Ala Ile Tyr Glu Asn Ser Ser Val Ser Phe Trp Ile Lys Ile Ser
                        930                 935                 940
        Lys Asp Leu Thr Asn Ser His Asn Glu Tyr Thr Ile Ile Asn Ser Ile
        945                 950                 955                 960
        Lys Gln Asn Ser Gly Trp Lys Leu Cys Ile Arg Asn Gly Asn Ile Glu
                        965                 970                 975
        Trp Ile Leu Gln Asp Ile Asn Arg Lys Tyr Lys Ser Leu Ile Phe Asp
                        980                 985                 990
        Tyr Ser Glu Ser Leu Ser His Thr Gly Tyr Thr Asn Lys Trp Phe Phe
                        995                 1000                1005
        Val Thr Ile Thr Asn Asn Ile Met Gly Tyr Met Lys Leu Tyr Ile
            1010                1015                1020
        Asn Gly Glu Leu Lys Gln Ser Glu Arg Ile Glu Asp Leu Asn Glu
            1025                1030                1035
        Val Lys Leu Asp Lys Thr Ile Val Phe Gly Ile Asp Glu Asn Ile
            1040                1045                1050
        Asp Glu Asn Gln Met Leu Trp Ile Arg Asp Phe Asn Ile Phe Ser
            1055                1060                1065
        Lys Glu Leu Ser Asn Glu Asp Ile Asn Ile Val Tyr Glu Gly Gln
            1070                1075                1080
        Ile Leu Arg Asn Val Ile Lys Asp Tyr Trp Gly Asn Pro Leu Lys
            1085                1090                1095
        Phe Asp Thr Glu Tyr Tyr Ile Ile Asn Asp Asn Tyr Ile Asp Arg
            1100                1105                1110
        Tyr Ile Ala Pro Lys Ser Asn Ile Leu Val Leu Val Gln Tyr Pro
            1115                1120                1125
```

```
Asp Arg Ser Lys Leu Tyr Thr Gly Asn Pro Ile Thr Ile Lys Ser
        1130                1135                1140

Val Ser Asp Lys Asn Pro Tyr Ser Arg Ile Leu Asn Gly Asp Asn
        1145                1150                1155

Ile Met Phe His Met Leu Tyr Asn Ser Gly Lys Tyr Met Ile Ile
        1160                1165                1170

Arg Asp Thr Asp Thr Ile Tyr Ala Ile Glu Gly Arg Glu Cys Ser
        1175                1180                1185

Lys Asn Cys Val Tyr Ala Leu Lys Leu Gln Ser Asn Leu Gly Asn
        1190                1195                1200

Tyr Gly Ile Gly Ile Phe Ser Ile Lys Asn Ile Val Ser Gln Asn
        1205                1210                1215

Lys Tyr Cys Ser Gln Ile Phe Ser Ser Phe Met Lys Asn Thr Met
        1220                1225                1230

Leu Leu Ala Asp Ile Tyr Lys Pro Trp Arg Phe Ser Phe Glu Asn
        1235                1240                1245

Ala Tyr Thr Pro Val Ala Val Thr Asn Tyr Glu Thr Lys Leu Leu
        1250                1255                1260

Ser Thr Ser Ser Phe Trp Lys Phe Ile Ser Arg Asp Pro Gly Trp
        1265                1270                1275

Val Glu
    1280

<210> SEQ ID NO 7
<211> LENGTH: 3858
<212> TYPE: DNA
<213> ORGANISM: Clostridium botulinum

<400> SEQUENCE: 7
atgacatggc cagtaaaaga ttttaattat agtgatcctg ttaatgacaa tgatatatta      60
tatttaagaa taccacaaaa taagttaatt actacacctg taaaagcttt tatgattact     120
caaaatattt gggtaatacc agaaagattt tcatcagata ctaatccaag tttaagtaaa     180
ccgcctagac ctacttcaaa gtatcaaagt tattatgatc ctagttattt atctactgat     240
gagcaaaaag atacattttt aaaagggatt ataaaattat ttaaaagaat aatgaaaga      300
gatataggaa aaaaattaat aaattattta gtagttggtt caccttttat gggagattca     360
agtacgcctg aagatacatt tgattttaca cgtcatacta ctaatattgc agttgaaaag     420
tttgaaaatg gtagttggaa agtaacaaat attataacac aagtgtatt gatatttgga     480
ccacttccta atatattaga ctatacagca tcccttacat tgcaaggaca acaatcaaat     540
ccatcatttg aagggtttgg aacattatct atactaaaag tagcacctga attttttgtta    600
acatttagtg atgtaacatc taatcaaagt tcagctgtat taggcaaatc tatatttttgt   660
atggatccag taatagcttt aatgcatgag ttaacacatt ctttgcatca attgtatgga    720
ataaatatac catctgataa aaggattcgt ccacaagtta gcgagggatt tttttctcaa    780
gatggaccca acgtacaatt tgaggaatta tacacatttg aggatcagat gttgaaata     840
atacctcaaa ttgaaagatt acaattaaga gaaaaagcat taggtcacta taagatata    900
gcgaaaagac ttaataatat taataaaact attccttcta gttggagtag taatatagat    960
aaatataaaa aaatatttct tgaaaagtat aattttgata agataataac aggaaatttt    1020
gttgtaaata ttgataaatt caatagctta tattcagact tgactaatgt tatgtcagaa    1080
gttgtttatt cttcgcaata taatgttaaa aacaggactc attattttc aaagcattat    1140
```

```
ctacctgtat ttgcaaatat attagatgat aatatttata ctataataaa cggttttaat    1200
ttaacaacta aaggttttaa tatagaaaat tcgggtcaga atatagaaag gaatcctgca    1260
ctacaaaaac ttagttcaga aagtgtagta gatttgttta caaaagtatg tttaagatta    1320
acaagaaata gtagagatga ttcaacatgt attcaagtta aaaataatac attaccttat    1380
gtagctgata aagatagcat ttcacaagaa atatttgaaa gtcaaattat tacagatgag    1440
actaatgtag aaaattattc agataatttt tcattagatg aatctatttt agatgcaaaa    1500
gtccctacta atcctgaagc agtagatcca ctgttaccca atgttaatat ggaacccttta   1560 aatgttccag gtgaagaaga agtatttat gatgatatta ctaaagatgt tgattattta    1620
aactcttatt attatttgga agcccaaaaa ttaagtaata atgttgaaaa tattactctt    1680
acaacttcag ttgaagaagc attaggttat agcaataaga tatacacatt tttacctagc    1740
ttagctgaaa aagtgaataa aggtgttcaa gcaggtttat tcttaaattg ggcgaatgaa    1800
gtagttgagg atttttactac aaatattatg aaaaaagata cattggataa aatatcagat    1860
gtatcagcca taattccata tataggacct gccttaaata taggaaattc agcattaagg    1920
ggaaacttta agcaagcatt tgcaacagct ggtgtagctt ttttgttaga aggatttcca    1980
gagtttacaa tacctgcact cggtgtatttt acctttata gttctattca agaaagagag    2040
aaaattatta aaactataga aaattgttta gaacaaagag ttaagagatg gaaagattca    2100
tatcaatgga tggtatcaaa ttggttgtca agaattacta ctcgatttaa tcatataagt    2160
tatcaaatgt atgattcttt gagttatcag gcagatgcaa tcaaagctaa aatagattta    2220
gaatataaaa aatactcagg aagtgataaa gaaaatataa aaagtcaagt tgaaaattta    2280
aaaaatagtt tagatgtaaa aatctcggaa gcaatgaata atataaataa attatacga    2340 gaatgttctg taacatactt atttaaaaat atgctcccta aagtaattga tgaattaaat    2400
aagtttgatt taaaaactaa aacagaatta attaatctta tagatagtca taatattatt    2460
ctagttggtg aagtagatag attaaaagca aaagtaaatg agagttttga aaatacaata    2520 cccttttaata ttttttcata tactaataat tctttattaa aagatatgat taatgaatat   2580
ttcaatagta ttaatgattc aaaaattttg agcttacaaa ataaaaaaaa tactttgatg    2640
gatacatcag atataacgc agaagtgaga gtagaaggca atgttcagct taatccaata    2700
tttccatttg actttaaatt aggtagttca ggggatgata gaggtaaagt tatagtaacc    2760
cagaatgaaa atattgtata taatgctatg tatgaaagtt ttagtattag ttttttggatt   2820 aggataaata aatgggtaag taatttacct ggatatacta taattgatag tgttaaaaat    2880
aactcaggtt ggagtatagg tattattagt aatttttttag tgtttacttt aaaacaaaat    2940
gaaaatagtg aacaagatat aaactttagt tatgatatat caaagaatgc tgcgggatat    3000
aataaatggt ttttttgtaac tattactacc aatatgatgg gaaatatgat gatttatata    3060
aatgaaaaat taatagatac tataaaagtt aaagagttaa ctggaattaa ttttagcaaa    3120
actataacat ttcaaatgaa taaaattcca atactggct taattacctc agattctgat    3180
aacatcaata tgtggataag ggatttttat atctttgcta aagaattaga tgataaagat    3240
attaatatat tatttaatag cttgcaatat actaatgttg taaaagatta ttggggaaat    3300
gatttaagat atgataaaga atattacatg attaacgtaa attatatgaa tagatatatg    3360
tctaaaaaag gcaatggaat tgttttttaat acacgtaaaa ataataatga cttcaatgaa    3420 ggatatataaaa ttataataaaa aagaattaga ggaaatacaa atgatactag agtacgagga    3480
```

-continued

```
gaaaatgtat tatattttaa tactacaatt gataacaaac aatatagttt aggtatgtat    3540
aaaccttcta gaaatctagg gactgattta gttccactag gtgcattgga tcaaccaatg    3600
gatgagatac gtaaatatgg ttcgtttata atacaaccat gcaatacttt tgattactat    3660
gcatcacaat tattttttgtc aagtaatgca acaacaaata ggcttggaat actatcaatt    3720
ggtagttata gtttcaaact tggagatgac tattggttta atcacgaata tttaattcct    3780
gttataaaaa tagagcatta tgcttcatta ttagaatcaa catcaactca ttgggttttt    3840
gtacctgcaa gtgaataa                                                  3858
```

<210> SEQ ID NO 8
<211> LENGTH: 1285
<212> TYPE: PRT
<213> ORGANISM: Clostridium botulinum

<400> SEQUENCE: 8

```
Met Thr Trp Pro Val Lys Asp Phe Asn Tyr Ser Asp Pro Val Asn Asp
1               5                   10                  15

Asn Asp Ile Leu Tyr Leu Arg Ile Pro Gln Asn Lys Leu Ile Thr Thr
            20                  25                  30

Pro Val Lys Ala Phe Met Ile Thr Gln Asn Ile Trp Val Ile Pro Glu
        35                  40                  45

Arg Phe Ser Ser Asp Thr Asn Pro Ser Leu Ser Lys Pro Pro Arg Pro
    50                  55                  60

Thr Ser Lys Tyr Gln Ser Tyr Tyr Asp Pro Ser Tyr Leu Ser Thr Asp
65                  70                  75                  80

Glu Gln Lys Asp Thr Phe Leu Lys Gly Ile Ile Lys Leu Phe Lys Arg
                85                  90                  95

Ile Asn Glu Arg Asp Ile Gly Lys Lys Leu Ile Asn Tyr Leu Val Val
            100                 105                 110

Gly Ser Pro Phe Met Gly Asp Ser Ser Thr Pro Glu Asp Thr Phe Asp
        115                 120                 125

Phe Thr Arg His Thr Thr Asn Ile Ala Val Glu Lys Phe Glu Asn Gly
    130                 135                 140

Ser Trp Lys Val Thr Asn Ile Ile Thr Pro Ser Val Leu Ile Phe Gly
145                 150                 155                 160

Pro Leu Pro Asn Ile Leu Asp Tyr Thr Ala Ser Leu Thr Leu Gln Gly
                165                 170                 175

Gln Gln Ser Asn Pro Ser Phe Glu Gly Phe Gly Thr Leu Ser Ile Leu
            180                 185                 190

Lys Val Ala Pro Glu Phe Leu Leu Thr Phe Ser Asp Val Thr Ser Asn
        195                 200                 205

Gln Ser Ser Ala Val Leu Gly Lys Ser Ile Phe Cys Met Asp Pro Val
    210                 215                 220

Ile Ala Leu Met His Glu Leu Thr His Ser Leu His Gln Leu Tyr Gly
225                 230                 235                 240

Ile Asn Ile Pro Ser Asp Lys Arg Ile Arg Pro Gln Val Ser Glu Gly
                245                 250                 255

Phe Phe Ser Gln Asp Gly Pro Asn Val Gln Phe Glu Glu Leu Tyr Thr
            260                 265                 270

Phe Gly Gly Ser Asp Val Glu Ile Ile Pro Gln Ile Glu Arg Leu Gln
        275                 280                 285

Leu Arg Glu Lys Ala Leu Gly His Tyr Lys Asp Ile Ala Lys Arg Leu
    290                 295                 300
```

```
Asn Asn Ile Asn Lys Thr Ile Pro Ser Ser Trp Ser Asn Ile Asp
305                 310                 315                 320

Lys Tyr Lys Lys Ile Phe Ser Glu Lys Tyr Asn Phe Asp Lys Asp Asn
            325                 330                 335

Thr Gly Asn Phe Val Val Asn Ile Asp Lys Phe Asn Ser Leu Tyr Ser
            340                 345                 350

Asp Leu Thr Asn Val Met Ser Glu Val Val Tyr Ser Ser Gln Tyr Asn
            355                 360                 365

Val Lys Asn Arg Thr His Tyr Phe Ser Lys His Tyr Leu Pro Val Phe
370                 375                 380

Ala Asn Ile Leu Asp Asp Asn Ile Tyr Thr Ile Ile Asn Gly Phe Asn
385                 390                 395                 400

Leu Thr Thr Lys Gly Phe Asn Ile Glu Asn Ser Gly Gln Asn Ile Glu
            405                 410                 415

Arg Asn Pro Ala Leu Gln Lys Leu Ser Ser Glu Ser Val Val Asp Leu
            420                 425                 430

Phe Thr Lys Val Cys Leu Arg Leu Thr Arg Asn Ser Arg Asp Asp Ser
            435                 440                 445

Thr Cys Ile Gln Val Lys Asn Asn Thr Leu Pro Tyr Val Ala Asp Lys
450                 455                 460

Asp Ser Ile Ser Gln Glu Ile Phe Glu Ser Gln Ile Ile Thr Asp Glu
465                 470                 475                 480

Thr Asn Val Glu Asn Tyr Ser Asp Asn Phe Ser Leu Asp Glu Ser Ile
            485                 490                 495

Leu Asp Ala Lys Val Pro Thr Asn Pro Glu Ala Val Asp Pro Leu Leu
            500                 505                 510

Pro Asn Val Asn Met Glu Pro Leu Asn Val Pro Gly Glu Glu Glu Val
            515                 520                 525

Phe Tyr Asp Asp Ile Thr Lys Asp Val Asp Tyr Leu Asn Ser Tyr Tyr
            530                 535                 540

Tyr Leu Glu Ala Gln Lys Leu Ser Asn Asn Val Glu Asn Ile Thr Leu
545                 550                 555                 560

Thr Thr Ser Val Glu Glu Ala Leu Gly Tyr Ser Asn Lys Ile Tyr Thr
            565                 570                 575

Phe Leu Pro Ser Leu Ala Glu Lys Val Asn Lys Gly Val Gln Ala Gly
            580                 585                 590

Leu Phe Leu Asn Trp Ala Asn Glu Val Val Glu Asp Phe Thr Thr Asn
            595                 600                 605

Ile Met Lys Lys Asp Thr Leu Asp Lys Ile Ser Asp Val Ser Ala Ile
610                 615                 620

Ile Pro Tyr Ile Gly Pro Ala Leu Asn Ile Gly Asn Ser Ala Leu Arg
625                 630                 635                 640

Gly Asn Phe Lys Gln Ala Phe Ala Thr Ala Gly Val Ala Phe Leu Leu
            645                 650                 655

Glu Gly Phe Pro Glu Phe Thr Ile Pro Ala Leu Gly Val Phe Thr Phe
            660                 665                 670

Tyr Ser Ser Ile Gln Glu Arg Glu Lys Ile Ile Lys Thr Ile Glu Asn
            675                 680                 685

Cys Leu Glu Gln Arg Val Lys Arg Trp Lys Asp Ser Tyr Gln Trp Met
            690                 695                 700

Val Ser Asn Trp Leu Ser Arg Ile Thr Thr Arg Phe Asn His Ile Ser
705                 710                 715                 720

Tyr Gln Met Tyr Asp Ser Leu Ser Tyr Gln Ala Asp Ala Ile Lys Ala
```

```
                725                 730                 735
Lys Ile Asp Leu Glu Tyr Lys Lys Tyr Ser Gly Ser Asp Lys Glu Asn
                    740                 745                 750

Ile Lys Ser Gln Val Glu Asn Leu Lys Asn Ser Leu Asp Val Lys Ile
                    755                 760                 765

Ser Glu Ala Met Asn Asn Ile Asn Lys Phe Ile Arg Glu Cys Ser Val
                    770                 775                 780

Thr Tyr Leu Phe Lys Asn Met Leu Pro Lys Val Ile Asp Glu Leu Asn
785                 790                 795                 800

Lys Phe Asp Leu Lys Thr Lys Thr Glu Leu Ile Asn Leu Ile Asp Ser
                    805                 810                 815

His Asn Ile Ile Leu Val Gly Glu Val Asp Arg Leu Lys Ala Lys Val
                    820                 825                 830

Asn Glu Ser Phe Glu Asn Thr Ile Pro Phe Asn Ile Phe Ser Tyr Thr
                    835                 840                 845

Asn Asn Ser Leu Leu Lys Asp Met Ile Asn Glu Tyr Phe Asn Ser Ile
                    850                 855                 860

Asn Asp Ser Lys Ile Leu Ser Leu Gln Asn Lys Lys Asn Thr Leu Met
865                 870                 875                 880

Asp Thr Ser Gly Tyr Asn Ala Glu Val Arg Val Glu Gly Asn Val Gln
                    885                 890                 895

Leu Asn Pro Ile Phe Pro Phe Asp Phe Lys Leu Gly Ser Ser Gly Asp
                    900                 905                 910

Asp Arg Gly Lys Val Ile Val Thr Gln Asn Glu Asn Ile Val Tyr Asn
                    915                 920                 925

Ala Met Tyr Glu Ser Phe Ser Ile Ser Phe Trp Ile Arg Ile Asn Lys
                    930                 935                 940

Trp Val Ser Asn Leu Pro Gly Tyr Thr Ile Ile Asp Ser Val Lys Asn
945                 950                 955                 960

Asn Ser Gly Trp Ser Ile Gly Ile Ile Ser Asn Phe Leu Val Phe Thr
                    965                 970                 975

Leu Lys Gln Asn Glu Asn Ser Glu Gln Asp Ile Asn Phe Ser Tyr Asp
                    980                 985                 990

Ile Ser Lys Asn Ala Ala Gly Tyr Asn Lys Trp Phe Phe Val Thr Ile
                    995                 1000                1005

Thr Thr Asn Met Met Gly Asn Met Met Ile Tyr Ile Asn Gly Lys
                    1010                1015                1020

Leu Ile Asp Thr Ile Lys Val Lys Glu Leu Thr Gly Ile Asn Phe
                    1025                1030                1035

Ser Lys Thr Ile Thr Phe Gln Met Asn Lys Ile Pro Asn Thr Gly
                    1040                1045                1050

Leu Ile Thr Ser Asp Ser Asp Asn Ile Asn Met Trp Ile Arg Asp
                    1055                1060                1065

Phe Tyr Ile Phe Ala Lys Glu Leu Asp Asp Lys Asp Ile Asn Ile
                    1070                1075                1080

Leu Phe Asn Ser Leu Gln Tyr Thr Asn Val Val Lys Asp Tyr Trp
                    1085                1090                1095

Gly Asn Asp Leu Arg Tyr Asp Lys Glu Tyr Tyr Met Ile Asn Val
                    1100                1105                1110

Asn Tyr Met Asn Arg Tyr Met Ser Lys Lys Gly Asn Gly Ile Val
                    1115                1120                1125

Phe Asn Thr Arg Lys Asn Asn Asn Asp Phe Asn Glu Gly Tyr Lys
                    1130                1135                1140
```

| | | | | | | | | | | |
|---|---|---|---|---|---|---|---|---|---|---|
|Ile|Ile|Ile|Lys|Arg|Ile|Arg|Gly|Asn|Thr|Asn|Asp|Thr|Arg|Val|
| |1145| | | |1150| | | |1155| |

Arg Gly Glu Asn Val Leu Tyr Phe Asn Thr Thr Ile Asp Asn Lys
    1160            1165            1170

Gln Tyr Ser Leu Gly Met Tyr Lys Pro Ser Arg Asn Leu Gly Thr
    1175            1180            1185

Asp Leu Val Pro Leu Gly Ala Leu Asp Gln Pro Met Asp Glu Ile
    1190            1195            1200

Arg Lys Tyr Gly Ser Phe Ile Ile Gln Pro Cys Asn Thr Phe Asp
    1205            1210            1215

Tyr Tyr Ala Ser Gln Leu Phe Leu Ser Ser Asn Ala Thr Thr Asn
    1220            1225            1230

Arg Leu Gly Ile Leu Ser Ile Gly Ser Tyr Ser Phe Lys Leu Gly
    1235            1240            1245

Asp Asp Tyr Trp Phe Asn His Glu Tyr Leu Ile Pro Val Ile Lys
    1250            1255            1260

Ile Glu His Tyr Ala Ser Leu Leu Glu Ser Thr Ser Thr His Trp
    1265            1270            1275

Val Phe Val Pro Ala Ser Glu
    1280            1285

<210> SEQ ID NO 9
<211> LENGTH: 3756
<212> TYPE: DNA
<213> ORGANISM: Clostridium botulinum

<400> SEQUENCE: 9

```
atgccaaaaa ttaatagttt taattataat gatcctgtta atgatagaac aattttatat      60
attaaaccag gcggttgtca agaattttat aaatcattta atattatgaa aaatatttgg     120
ataattccag agagaaatgt aattggtaca accccccaag attttcatcc gcctacttca     180
ttaaaaaatg gagatagtag ttattatgac cctaattatt tacaaagtga tgaagaaaag     240
gatagatttt aaaaatagt cacaaaaata tttaatagaa taaataataa tctttcagga     300
gggattttat tagaagaact gtcaaaagct aatccatatt tagggaatga atactcca     360
gataatcaat tccatattgg tgatgcatca gcagttgaga ttaaattctc aaatggtagc     420
caagacatac tattacctaa tgttattata atgggagcag agcctgattt atttgaaact     480
aacagttcca atatttctct aagaaataat tatatgccaa gcaatcaccg ttttggatca     540
atagctatag taacattctc acctgaatat tcttttagat ttaatgataa ttgtatgaat     600
gaatttattc aagatcctgc tcttacatta atgcatgaat taatacattc attacatgga     660
ctatatgggg ctaaagggat tactacaaag tatactataa cacaaaaaca aaatccccta     720
ataacaaata taagaggtac aaatattgaa gaattcttaa cttttggagg tactgattta     780
aacattatta ctagtgctca gtccaatgat atctatacta atcttctagc tgattataaa     840
aaaatagcgt ctaaacttag caaagtacaa gtatctaatc cactacttaa tccttataaa     900
gatgttttg aagcaaagta tggattagat aaagatgcta gcggaattta ttcggtaaat     960
ataaacaaat ttaatgatat ttttaaaaaa ttatacagct ttacggaatt tgatttacga    1020
actaaatttc aagttaaatg taggcaaact tatattggac agtataaata cttcaaactt    1080
tcaaacttgt taatgattc tatttataat atatcagaag gctataatat aaataattta    1140
aaggtaaatt ttagaggaca gaatgcaaat ttaaatccta gaattattac accaattaca    1200
```

```
ggtagaggac tagtaaaaaa aatcattaga ttttgtaaaa atattgtttc tgtaaaaggc    1260
ataaggaaat caatatgtat cgaaataaat aatggtgagt tattttttgt ggcttccgag    1320
aatagttata atgatgataa tataaatact cctaaagaaa ttgacgatac agtaacttca    1380
aataataatt atgaaaatga tttagatcag gttattttaa attttaatag tgaatcagca    1440
cctggacttt cagatgaaaa attaaattta actatccaaa atgatgctta tataccaaaa    1500
tatgattcta atggaacaag tgatatagaa caacatgatg ttaatgaact taatgtattt    1560
ttctatttag atgcacagaa agtgcccgaa ggtgaaaata atgtcaatct cacctcttca    1620
attgatacag cattattaga acaacctaaa atatatacat tttttcatc agaatttatt     1680 aataatgtca ataaacctgt gcaagcagca ttatttgtaa gctggataca acaagtgtta    1740
gtagatttta ctactgaagc taaccaaaaa agtactgttg ataaaattgc agatatttct    1800
atagttgttc catatatagg tcttgcttta aatataggaa atgaagcaca aaaaggaaat    1860
tttaaagatg cacttgaatt attaggagca ggtatttat tagaatttga acccgagctt     1920
ttaattccta caatttagt attcacgata aaatcttttt taggttcatc tgataataaa     1980
aataaagtta ttaaagcaat aaataatgca ttgaaagaaa gagatgaaaa atggaaagaa    2040
gtatatagtt ttatagtatc gaattggatg actaaaatta atacacaatt taataaaaga    2100
aaagaacaaa tgtatcaagc tttacaaaat caagtaaatg caattaaaac aataatagaa    2160
tctaagtata atagttatac tttagaggaa aaaaatgagc ttacaaataa atatgatatt    2220
aagcaaatag aaaatgaact taatcaaaag gtttctatag caatgaataa tatagacagg    2280
ttcttaactg aaagttctat atcctatta atgaaaataa taaatgaagt aaaaattaat    2340
aaattaagag aatatgatga gaatgtcaaa acgtatttat tgaattatat tatacaacat    2400
ggatcaatct tgggagagag tcagcaagaa ctaaattcta tggtaactga taccctaaat    2460
aatagtattc cttttaagct ttcttcttat acagatgata aaatttttaat ttcatatttt   2520 aataaattct ttaagagaat taaaagtagt tcagttttaa atatgagata taaaaaatgat   2580 aaatacgtag atacttcagg atatgattca atatataaata ttaatggaga tgtatataaa   2640
tatccaacta ataaaaatca atttggaata tataatgata aacttagtga agttaatata    2700
tctcaaaatg attacattat atatgataat aaatataaaa attttagtat tagttttgg     2760 gtaagaattc ctaactatga taataagata gtaaatgtta ataatgaata cactataata    2820
aattgtatga gagataataa ttcaggatgg aaagtatctc ttaatcataa tgaaataatt    2880
tggacattcg aagataatcg aggaattaat caaaaattag catttaacta tggtaacgca    2940 aatggtatt ctgattatat aaataagtgg attttgtaa ctataactaa tgatagatta     3000
ggagattcta aactttatat taatggaaat ttaatagatc aaaaatcaat tttaaattta   3060
ggtaatattc atgttagtga caatatatta tttaaaatag ttaattgtag ttatacaaga    3120
tatattggta ttgatatttt taatattttt gataaagaat tagatgaaac agaaattcaa    3180
actttatata gcaatgaacc taatacaaat attttgaagg ttttttgggg aaattatttg    3240
ctttatgaca aagaatacta tttattaaat gtgttaaaac caaataactt tattgatagg    3300
agaaaagatt ctactttaag cattaataat ataagaagca ctattctttt agctaataga    3360
ttatatagtg gaataaaagt taaaatacaa agagttaata atagtagtac taacgataat    3420
cttgttagaa agaatgatca ggtatatatt aattttgtag ccagcaaaac tcacttattt    3480
ccattatatg ctgatacagc taccacaaat aaagagaaaa caataaaaaat atcatcatct   3540 ggcaatagat ttaatcaagt agtagttatg aattcagtag gaaattgtac aatgaatttt    3600
```

```
aaaaataata atgaaataa tattgggttg ttaggtttca aggcagatac tgtcgttgct   3660
agtacttggt attatacaca tatgagagat catacaaaca gcaatggatg tttttggaac   3720
tttatttctg aagaacatgg atggcaagaa aaataa                            3756
```

<210> SEQ ID NO 10
<211> LENGTH: 1251
<212> TYPE: PRT
<213> ORGANISM: Clostridium botulinum

<400> SEQUENCE: 10

```
Met Pro Lys Ile Asn Ser Phe Asn Tyr Asn Asp Pro Val Asn Asp Arg
1               5                   10                  15

Thr Ile Leu Tyr Ile Lys Pro Gly Gly Cys Gln Glu Phe Tyr Lys Ser
            20                  25                  30

Phe Asn Ile Met Lys Asn Ile Trp Ile Ile Pro Glu Arg Asn Val Ile
        35                  40                  45

Gly Thr Thr Pro Gln Asp Phe His Pro Pro Thr Ser Leu Lys Asn Gly
    50                  55                  60

Asp Ser Ser Tyr Tyr Asp Pro Asn Tyr Leu Gln Ser Asp Glu Glu Lys
65                  70                  75                  80

Asp Arg Phe Leu Lys Ile Val Thr Lys Ile Phe Asn Arg Ile Asn Asn
                85                  90                  95

Asn Leu Ser Gly Gly Ile Leu Leu Glu Leu Ser Lys Ala Asn Pro
            100                 105                 110

Tyr Leu Gly Asn Asp Asn Thr Pro Asp Asn Gln Phe His Ile Gly Asp
        115                 120                 125

Ala Ser Ala Val Glu Ile Lys Phe Ser Asn Gly Ser Gln Asp Ile Leu
    130                 135                 140

Leu Pro Asn Val Ile Ile Met Gly Ala Glu Pro Asp Leu Phe Glu Thr
145                 150                 155                 160

Asn Ser Ser Asn Ile Ser Leu Arg Asn Asn Tyr Met Pro Ser Asn His
                165                 170                 175

Arg Phe Gly Ser Ile Ala Ile Val Thr Phe Ser Pro Glu Tyr Ser Phe
            180                 185                 190

Arg Phe Asn Asp Asn Cys Met Asn Glu Phe Ile Gln Asp Pro Ala Leu
        195                 200                 205

Thr Leu Met His Glu Leu Ile His Ser Leu His Gly Leu Tyr Gly Ala
    210                 215                 220

Lys Gly Ile Thr Thr Lys Tyr Thr Ile Thr Gln Lys Gln Asn Pro Leu
225                 230                 235                 240

Ile Thr Asn Ile Arg Gly Thr Asn Ile Glu Glu Phe Leu Thr Phe Gly
                245                 250                 255

Gly Thr Asp Leu Asn Ile Ile Thr Ser Ala Gln Ser Asn Asp Ile Tyr
            260                 265                 270

Thr Asn Leu Leu Ala Asp Tyr Lys Lys Ile Ala Ser Lys Leu Ser Lys
        275                 280                 285

Val Gln Val Ser Asn Pro Leu Leu Asn Pro Tyr Lys Asp Val Phe Glu
    290                 295                 300

Ala Lys Tyr Gly Leu Asp Lys Asp Ala Ser Gly Ile Tyr Ser Val Asn
305                 310                 315                 320

Ile Asn Lys Phe Asn Asp Ile Phe Lys Lys Leu Tyr Ser Phe Thr Glu
                325                 330                 335

Phe Asp Leu Arg Thr Lys Phe Gln Val Lys Cys Arg Gln Thr Tyr Ile
```

```
                340                 345                 350
Gly Gln Tyr Lys Tyr Phe Lys Leu Ser Asn Leu Leu Asn Asp Ser Ile
            355                 360                 365
Tyr Asn Ile Ser Glu Gly Tyr Asn Ile Asn Asn Leu Lys Val Asn Phe
        370                 375                 380
Arg Gly Gln Asn Ala Asn Leu Asn Pro Arg Ile Ile Thr Pro Ile Thr
385                 390                 395                 400
Gly Arg Gly Leu Val Lys Lys Ile Ile Arg Phe Cys Lys Asn Ile Val
                405                 410                 415
Ser Val Lys Gly Ile Arg Lys Ser Ile Cys Ile Glu Ile Asn Asn Gly
            420                 425                 430
Glu Leu Phe Phe Val Ala Ser Glu Asn Ser Tyr Asn Asp Asp Asn Ile
        435                 440                 445
Asn Thr Pro Lys Glu Ile Asp Asp Thr Val Thr Ser Asn Asn Asn Tyr
    450                 455                 460
Glu Asn Asp Leu Asp Gln Val Ile Leu Asn Phe Asn Ser Glu Ser Ala
465                 470                 475                 480
Pro Gly Leu Ser Asp Glu Lys Leu Asn Leu Thr Ile Gln Asn Asp Ala
                485                 490                 495
Tyr Ile Pro Lys Tyr Asp Ser Asn Gly Thr Ser Asp Ile Glu Gln His
            500                 505                 510
Asp Val Asn Glu Leu Asn Val Phe Phe Tyr Leu Asp Ala Gln Lys Val
        515                 520                 525
Pro Glu Gly Glu Asn Asn Val Asn Leu Thr Ser Ser Ile Asp Thr Ala
    530                 535                 540
Leu Leu Glu Gln Pro Lys Ile Tyr Thr Phe Phe Ser Ser Glu Phe Ile
545                 550                 555                 560
Asn Asn Val Asn Lys Pro Val Gln Ala Ala Leu Phe Val Ser Trp Ile
                565                 570                 575
Gln Gln Val Leu Val Asp Phe Thr Thr Glu Ala Asn Gln Lys Ser Thr
            580                 585                 590
Val Asp Lys Ile Ala Asp Ile Ser Ile Val Val Pro Tyr Ile Gly Leu
        595                 600                 605
Ala Leu Asn Ile Gly Asn Glu Ala Gln Lys Gly Asn Phe Lys Asp Ala
    610                 615                 620
Leu Glu Leu Leu Gly Ala Gly Ile Leu Leu Glu Phe Glu Pro Glu Leu
625                 630                 635                 640
Leu Ile Pro Thr Ile Leu Val Phe Thr Ile Lys Ser Phe Leu Gly Ser
                645                 650                 655
Ser Asp Asn Lys Asn Lys Val Ile Lys Ala Ile Asn Asn Ala Leu Lys
            660                 665                 670
Glu Arg Asp Glu Lys Trp Lys Glu Val Tyr Ser Phe Ile Val Ser Asn
        675                 680                 685
Trp Met Thr Lys Ile Asn Thr Gln Phe Asn Lys Arg Lys Glu Gln Met
    690                 695                 700
Tyr Gln Ala Leu Gln Asn Gln Val Asn Ala Ile Lys Thr Ile Ile Glu
705                 710                 715                 720
Ser Lys Tyr Asn Ser Tyr Thr Leu Glu Glu Lys Asn Glu Leu Thr Asn
                725                 730                 735
Lys Tyr Asp Ile Lys Gln Ile Glu Asn Glu Leu Asn Gln Lys Val Ser
            740                 745                 750
Ile Ala Met Asn Asn Ile Asp Arg Phe Leu Thr Glu Ser Ser Ile Ser
        755                 760                 765
```

-continued

```
Tyr Leu Met Lys Ile Ile Asn Glu Val Lys Ile Asn Lys Leu Arg Glu
    770                 775                 780
Tyr Asp Glu Asn Val Lys Thr Tyr Leu Leu Asn Tyr Ile Ile Gln His
785                 790                 795                 800
Gly Ser Ile Leu Gly Glu Ser Gln Gln Glu Leu Asn Ser Met Val Thr
                805                 810                 815
Asp Thr Leu Asn Asn Ser Ile Pro Phe Lys Leu Ser Ser Tyr Thr Asp
                    820                 825                 830
Asp Lys Ile Leu Ile Ser Tyr Phe Asn Lys Phe Phe Lys Arg Ile Lys
                835                 840                 845
Ser Ser Ser Val Leu Asn Met Arg Tyr Lys Asn Asp Lys Tyr Val Asp
    850                 855                 860
Thr Ser Gly Tyr Asp Ser Asn Ile Asn Ile Asn Gly Asp Val Tyr Lys
865                 870                 875                 880
Tyr Pro Thr Asn Lys Asn Gln Phe Gly Ile Tyr Asn Asp Lys Leu Ser
                885                 890                 895
Glu Val Asn Ile Ser Gln Asn Asp Tyr Ile Ile Tyr Asp Asn Lys Tyr
                900                 905                 910
Lys Asn Phe Ser Ile Ser Phe Trp Val Arg Ile Pro Asn Tyr Asp Asn
            915                 920                 925
Lys Ile Val Asn Val Asn Asn Glu Tyr Thr Ile Asn Cys Met Arg
        930                 935                 940
Asp Asn Asn Ser Gly Trp Lys Val Ser Leu Asn His Asn Glu Ile Ile
945                 950                 955                 960
Trp Thr Phe Glu Asp Asn Arg Gly Ile Asn Gln Lys Leu Ala Phe Asn
                965                 970                 975
Tyr Gly Asn Ala Asn Gly Ile Ser Asp Tyr Ile Asn Lys Trp Ile Phe
            980                 985                 990
Val Thr Ile Thr Asn Asp Arg Leu  Gly Asp Ser Lys Leu  Tyr Ile Asn
            995                 1000                1005
Gly Asn  Leu Ile Asp Gln Lys  Ser Ile Leu Asn Leu  Gly Asn Ile
    1010                1015                1020
His Val  Ser Asp Asn Ile Leu  Phe Lys Ile Val Asn  Cys Ser Tyr
    1025                1030                1035
Thr Arg  Tyr Ile Gly Ile Arg  Tyr Phe Asn Ile Phe  Asp Lys Glu
    1040                1045                1050
Leu Asp  Glu Thr Glu Ile Gln  Thr Leu Tyr Ser Asn  Glu Pro Asn
    1055                1060                1065
Thr Asn  Ile Leu Lys Asp Phe  Trp Gly Asn Tyr Leu  Leu Tyr Asp
    1070                1075                1080
Lys Glu  Tyr Tyr Leu Leu Asn  Val Leu Lys Pro Asn  Asn Phe Ile
    1085                1090                1095
Asp Arg  Arg Lys Asp Ser Thr  Leu Ser Ile Asn Asn  Ile Arg Ser
    1100                1105                1110
Thr Ile  Leu Leu Ala Asn Arg  Leu Tyr Ser Gly Ile  Lys Val Lys
    1115                1120                1125
Ile Gln  Arg Val Asn Asn Ser  Ser Thr Asn Asp Asn  Leu Val Arg
    1130                1135                1140
Lys Asn  Asp Gln Val Tyr Ile  Asn Phe Val Ala Ser  Lys Thr His
    1145                1150                1155
Leu Phe  Pro Leu Tyr Ala Asp  Thr Ala Thr Thr Asn  Lys Glu Lys
    1160                1165                1170
```

-continued

| | | | | | | | | | | |
|---|---|---|---|---|---|---|---|---|---|---|
| Thr | Ile | Lys | Ile | Ser | Ser | Ser | Gly | Asn | Arg | Phe | Asn | Gln | Val | Val |
| | 1175 | | | | 1180 | | | | | 1185 | | | | |
| Val | Met | Asn | Ser | Val | Gly | Asn | Cys | Thr | Met | Asn | Phe | Lys | Asn | Asn |
| 1190 | | | | | 1195 | | | | | 1200 | | | | |
| Asn | Gly | Asn | Asn | Ile | Gly | Leu | Leu | Gly | Phe | Lys | Ala | Asp | Thr | Val |
| | 1205 | | | | 1210 | | | | | 1215 | | | | |
| Val | Ala | Ser | Thr | Trp | Tyr | Tyr | Thr | His | Met | Arg | Asp | His | Thr | Asn |
| 1220 | | | | | 1225 | | | | | 1230 | | | | |
| Ser | Asn | Gly | Cys | Phe | Trp | Asn | Phe | Ile | Ser | Glu | Glu | His | Gly | Trp |
| | 1235 | | | | 1240 | | | | | 1245 | | | | |
| Gln | Glu | Lys | | | | | | | | | | | | |
| | 1250 | | | | | | | | | | | | | |

<210> SEQ ID NO 11
<211> LENGTH: 3843
<212> TYPE: DNA
<213> ORGANISM: Clostridium botulinum

<400> SEQUENCE: 11

```
atgccagttg taataaatag ttttaattat aatgaccctg ttaatgatga acaattttta    60
tacatgcaga aaccatatga agaaagaagt agaaaatatt ataaagcttt tgagattatg   120
cctaatgttt ggataatgcc tgagagagat acaataggaa ctaagcctga tgagtttcag   180
gtgccggatt cattaaagaa cggaagtagt gcttattatg atcctaatta tttaaccact   240
gatgctgaaa aagatagata tttaaaaaca atgataaaat tatttaatag aattaatagt   300
aatcctacag ggaaagtttt gttagaagaa gtatcaaatg ctagaccata tttaggagat   360
gatgacacgc taattaatga attccttcca gttaatgtaa ctacaagtgt taatataaaa   420
ttttcaactg atgttgaaag ttcaataata tcgaatcttc ttgtattggg agcaggacct   480
gatatattta agcttactg taccccctt gtaaggttta ataagtcaga taaattaatt   540
gaaccaagta atcatggttt tggatcaatt aatatcttga cattttcacc tgagtatgaa   600
catattttta atgatattag tggagggaat cataatagta cagaatcatt tattgcagat   660
cctgcaattt cactagctca tgaattgata catgcactac atggattata cgggctaag   720
gcagttactc ataaagagtc tctagtagca gagcgaggac ctcttatgat agccgaaaag   780
cccataaggc tagaagaatt tttaactttt ggaggtgagg atttaaatat cattcctagt   840
gctatgaagg aaaaaatata taacgatctt ttagctaact atgaaaaaat agctactaga   900
cttagagaag ttaatacggc tcctcctgga tatgatatta tgaatataa agattattt    960
caatggaagt atggactaga tagaaatgca gatggaagtt atactgtgaa tagaaataaa  1020
tttaatgaaa tttataaaaa attatatagc tttacagaga ttgacttagc aaataaattt  1080
aaagtaaaat gtagaaatac ttattttatt aaatatggat ttgtaaaagt tccaaatttg  1140
ttagatgatg atatttatac tgtatcagag gggtttaata taggtaattt agcagtaaac  1200
aatcgcggac aaaatataaa tttaaatcct aaaattattg attccattcc agataaaggt  1260
ttagtggaaa agattattaa attttgtaag agcattattc ctagaaaagg tacgaagcag  1320
tcaccgtcac tatgcattag agtaaataat agggagttat tttttgtagc ttcagaaagt  1380
agctataatg aaagtgatat taatacacct aaagaaattg acgatacaac aaatctaaat  1440
aataattata gaaataattt agatgaagtt attttagatt ataatagtga gacaatacct  1500
caaatatcaa atcgaacatt aaatacactt gtacaagaca atagttatgt gccaagatat  1560
gattctaatg gaacaagtga aatagaggaa tatgatgttg ttgactttaa tgtattttc   1620
```

```
tatttacatg cacaaaaagt accagaaggt gaaaccaata taagtttaac ttcttcaatt    1680
gatacagcat tattagaaga atccaaagta tatacatttt tttcttcaga gtttatcgat    1740
actatcaata aacctgtaaa tgcagcacta tttatagatt ggataagcaa agtaataaga    1800
gattttacca ctgaagctac acaaaaaagt actgttgata agattgcaga catatcttta    1860
attgtaccct atgtaggtct tgctttgaat atagttattg aggcagaaaa aggaaatttt    1920
gaggaggcat ttgaattatt aggagcgggt atttattag aatttgtgcc agagcttaca     1980
attcctgtaa ttttagtgtt tacgataaaa tcctatatag attcatatga gaataaaaat    2040
aaagcaatta aagcaataaa taattcatta atcgaaagag aagcaaagtg aaagaaata    2100 tatagttgga tagtatcaaa ttggcttact agaattaata cgcaatttaa taaaagaaaa    2160
gagcaaatgt atcaggcttt acaaaatcaa gtagatgcaa taaaaacagc aatagaatat    2220
aaatataata attatacttc agatgagaaa aatagacttg aatctaaata taatatcaat    2280
aatatagaag aagaattgaa taaaaaagtt tctttagcaa tgaaaaatat agaaagattt    2340
atgacagaaa gttctatatc ttatttaatg aaattaataa atgaagccga agttggtaaa    2400
ttaaaagaat atgataaaca tgttaagagc gatttattag actatattct ctaccataaa    2460
ttaatcttag gagagcagac aaaggaatta attgatttgg tgactagtac tttgaatagt    2520
agtattccat ttgaactttc ttcatatact aatgataaaa ttctaattat atattttaat    2580
agattatata aaaaaattaa agatagttct attttagata tgcgatatga aataataaaa    2640
tttatagata tctctggata tggttcaaat ataagcatta atggaaacgt atatatttat    2700
tcaacaaata gaaatcaatt tggaatatat agtggtaggc ttagtgaagt taatatagct    2760
caaaataatg atattatata caatagtaga tatcaaaatt ttagtattag tttctgggta    2820
accattccta aacactacag acctatgaat cgtaatcggg aatacactat aataaattgt    2880
atggggaata ataattcggg atggaaaata tcacttagaa ctattagaga ttgtgaaata    2940
atttggactt tacaagatac ttccggaaat aaggaaaaat taattttag gtatgaagaa    3000 cttgctagta tatctgatta tataaataaa tggattttg taactattac taataataga    3060
ttaggcaatt ctagaattta catcaatgga aatttaatag ttgaaaaatc aatttcgaat    3120
ttaggtgata ttcatgttag tgataatata ttatttaaaa ttgttggttg tgatgatgaa    3180
acgtatgttg gtataagata ttttaaagtt tttaatacgg aattagataa aacagaaatt    3240
gagactttat atagtaatga gccagatcca agtatcttaa aagactattg gggaaattat    3300
ttgctatata ataaaaaata ttatttattc aatttactaa gaaaagataa gtatattact    3360
cggaattcag gcatttttaaa tattaatcaa caaagaggtg ttactggagg catatctgtt    3420
tttttgaact ataaattata tgaaggagta gaagttatta taagaaaaaa tgctcctata    3480
gatatatcta atacagataa ttttgttaga aaaaacgatc tagcatacat taatgtagta    3540
gatcatggtg tagaatatcg gttatatgct gatatatcaa ttacaaaatc agagaaaata    3600
ataaaattaa taagaacatc taatccaaac gatagcttag gtcaaattat agttatggat    3660
tcaataggaa ataattgcac aatgaatttt caaaacaatg atgggagcaa tataggatta    3720
ctaggttttc attcagatga tttggttgct agtagttggt attataacca tatacgaaga    3780
aacactagca gtaatggatg cttttggagt tttatttcta aagagcatgg ttggaaagaa    3840
taa                                                                 3843
```

<210> SEQ ID NO 12

<211> LENGTH: 1280
<212> TYPE: PRT
<213> ORGANISM: Clostridium botulinum

<400> SEQUENCE: 12

```
Met Pro Val Val Ile Asn Ser Phe Asn Tyr Asn Asp Pro Val Asn Asp
1               5                   10                  15

Glu Thr Ile Leu Tyr Met Gln Lys Pro Tyr Glu Glu Arg Ser Arg Lys
            20                  25                  30

Tyr Tyr Lys Ala Phe Glu Ile Met Pro Asn Val Trp Ile Met Pro Glu
        35                  40                  45

Arg Asp Thr Ile Gly Thr Lys Pro Asp Glu Phe Gln Val Pro Asp Ser
50                  55                  60

Leu Lys Asn Gly Ser Ser Ala Tyr Tyr Asp Pro Asn Tyr Leu Thr Thr
65                  70                  75                  80

Asp Ala Glu Lys Asp Arg Tyr Leu Lys Thr Met Ile Lys Leu Phe Asn
                85                  90                  95

Arg Ile Asn Ser Asn Pro Thr Gly Lys Val Leu Leu Glu Glu Val Ser
            100                 105                 110

Asn Ala Arg Pro Tyr Leu Gly Asp Asp Asp Thr Leu Ile Asn Glu Phe
        115                 120                 125

Leu Pro Val Asn Val Thr Thr Ser Val Asn Ile Lys Phe Ser Thr Asp
130                 135                 140

Val Glu Ser Ser Ile Ile Ser Asn Leu Leu Val Leu Gly Ala Gly Pro
145                 150                 155                 160

Asp Ile Phe Lys Ala Tyr Cys Thr Pro Leu Val Arg Phe Asn Lys Ser
                165                 170                 175

Asp Lys Leu Ile Glu Pro Ser Asn His Gly Phe Gly Ser Ile Asn Ile
            180                 185                 190

Leu Thr Phe Ser Pro Glu Tyr Glu His Ile Phe Asn Asp Ile Ser Gly
        195                 200                 205

Gly Asn His Asn Ser Thr Glu Ser Phe Ile Ala Asp Pro Ala Ile Ser
210                 215                 220

Leu Ala His Glu Leu Ile His Ala Leu His Gly Leu Tyr Gly Ala Lys
225                 230                 235                 240

Ala Val Thr His Lys Glu Ser Leu Val Ala Glu Arg Gly Pro Leu Met
                245                 250                 255

Ile Ala Glu Lys Pro Ile Arg Leu Glu Glu Phe Leu Thr Phe Gly Gly
            260                 265                 270

Glu Asp Leu Asn Ile Ile Pro Ser Ala Met Lys Glu Lys Ile Tyr Asn
        275                 280                 285

Asp Leu Leu Ala Asn Tyr Glu Lys Ile Ala Thr Arg Leu Arg Glu Val
290                 295                 300

Asn Thr Ala Pro Pro Gly Tyr Asp Ile Asn Glu Tyr Lys Asp Tyr Phe
305                 310                 315                 320

Gln Trp Lys Tyr Gly Leu Asp Arg Asn Ala Asp Gly Ser Tyr Thr Val
                325                 330                 335

Asn Arg Asn Lys Phe Asn Glu Ile Tyr Lys Lys Leu Tyr Ser Phe Thr
            340                 345                 350

Glu Ile Asp Leu Ala Asn Lys Phe Lys Val Lys Cys Arg Asn Thr Tyr
        355                 360                 365

Phe Ile Lys Tyr Gly Phe Val Lys Val Pro Asn Leu Leu Asp Asp Asp
370                 375                 380

Ile Tyr Thr Val Ser Glu Gly Phe Asn Ile Gly Asn Leu Ala Val Asn
```

```
                385                 390                 395                 400
Asn Arg Gly Gln Asn Ile Asn Leu Asn Pro Lys Ile Ile Asp Ser Ile
                    405                 410                 415
Pro Asp Lys Gly Leu Val Glu Lys Ile Ile Lys Phe Cys Lys Ser Ile
                420                 425                 430
Ile Pro Arg Lys Gly Thr Lys Gln Ser Pro Ser Leu Cys Ile Arg Val
            435                 440                 445
Asn Asn Arg Glu Leu Phe Phe Val Ala Ser Glu Ser Tyr Asn Glu
        450                 455                 460
Ser Asp Ile Asn Thr Pro Lys Glu Ile Asp Thr Thr Asn Leu Asn
465                 470                 475                 480
Asn Asn Tyr Arg Asn Asn Leu Asp Glu Val Ile Leu Asp Tyr Asn Ser
                485                 490                 495
Glu Thr Ile Pro Gln Ile Ser Asn Arg Thr Leu Asn Thr Leu Val Gln
                500                 505                 510
Asp Asn Ser Tyr Val Pro Arg Tyr Asp Ser Asn Gly Thr Ser Glu Ile
                515                 520                 525
Glu Glu Tyr Asp Val Val Asp Phe Asn Val Phe Phe Tyr Leu His Ala
            530                 535                 540
Gln Lys Val Pro Glu Gly Glu Thr Asn Ile Ser Leu Thr Ser Ser Ile
545                 550                 555                 560
Asp Thr Ala Leu Leu Glu Glu Ser Lys Val Tyr Thr Phe Phe Ser Ser
                565                 570                 575
Glu Phe Ile Asp Thr Ile Asn Lys Pro Val Asn Ala Ala Leu Phe Ile
                580                 585                 590
Asp Trp Ile Ser Lys Val Ile Arg Asp Phe Thr Thr Glu Ala Thr Gln
            595                 600                 605
Lys Ser Thr Val Asp Lys Ile Ala Asp Ile Ser Leu Ile Val Pro Tyr
            610                 615                 620
Val Gly Leu Ala Leu Asn Ile Val Ile Glu Ala Glu Lys Gly Asn Phe
625                 630                 635                 640
Glu Glu Ala Phe Glu Leu Leu Gly Ala Gly Ile Leu Leu Glu Phe Val
                645                 650                 655
Pro Glu Leu Thr Ile Pro Val Ile Leu Val Phe Thr Ile Lys Ser Tyr
                660                 665                 670
Ile Asp Ser Tyr Glu Asn Lys Asn Lys Ala Ile Lys Ala Ile Asn Asn
            675                 680                 685
Ser Leu Ile Glu Arg Glu Ala Lys Trp Lys Glu Ile Tyr Ser Trp Ile
        690                 695                 700
Val Ser Asn Trp Leu Thr Arg Ile Asn Thr Gln Phe Asn Lys Arg Lys
705                 710                 715                 720
Glu Gln Met Tyr Gln Ala Leu Gln Asn Gln Val Asp Ala Ile Lys Thr
                725                 730                 735
Ala Ile Glu Tyr Lys Tyr Asn Asn Tyr Thr Ser Asp Glu Lys Asn Arg
                740                 745                 750
Leu Glu Ser Lys Tyr Asn Ile Asn Asn Ile Glu Glu Glu Leu Asn Lys
            755                 760                 765
Lys Val Ser Leu Ala Met Lys Asn Ile Glu Arg Phe Met Thr Glu Ser
770                 775                 780
Ser Ile Ser Tyr Leu Met Lys Leu Ile Asn Glu Ala Glu Val Gly Lys
785                 790                 795                 800
Leu Lys Glu Tyr Asp Lys His Val Lys Ser Asp Leu Leu Asp Tyr Ile
                805                 810                 815
```

-continued

Leu Tyr His Lys Leu Ile Leu Gly Glu Gln Thr Lys Glu Leu Ile Asp
              820                 825                 830

Leu Val Thr Ser Thr Leu Asn Ser Ser Ile Pro Phe Glu Leu Ser Ser
              835                 840                 845

Tyr Thr Asn Asp Lys Ile Leu Ile Ile Tyr Phe Asn Arg Leu Tyr Lys
    850                 855                 860

Lys Ile Lys Asp Ser Ser Ile Leu Asp Met Arg Tyr Glu Asn Asn Lys
865                 870                 875                 880

Phe Ile Asp Ile Ser Gly Tyr Gly Ser Asn Ile Ser Ile Asn Gly Asn
                885                 890                 895

Val Tyr Ile Tyr Ser Thr Asn Arg Asn Gln Phe Gly Ile Tyr Ser Gly
    900                 905                 910

Arg Leu Ser Glu Val Asn Ile Ala Gln Asn Asn Asp Ile Ile Tyr Asn
        915                 920                 925

Ser Arg Tyr Gln Asn Phe Ser Ile Ser Phe Trp Val Thr Ile Pro Lys
    930                 935                 940

His Tyr Arg Pro Met Asn Arg Asn Arg Glu Tyr Thr Ile Ile Asn Cys
945                 950                 955                 960

Met Gly Asn Asn Asn Ser Gly Trp Lys Ile Ser Leu Arg Thr Ile Arg
                965                 970                 975

Asp Cys Glu Ile Ile Trp Thr Leu Gln Asp Thr Ser Gly Asn Lys Glu
            980                 985                 990

Lys Leu Ile Phe Arg Tyr Glu Glu Leu Ala Ser Ile Ser Asp Tyr Ile
        995                 1000                1005

Asn Lys Trp Ile Phe Val Thr Ile Thr Asn Asn Arg Leu Gly Asn
    1010                1015                1020

Ser Arg Ile Tyr Ile Asn Gly Asn Leu Ile Val Glu Lys Ser Ile
    1025                1030                1035

Ser Asn Leu Gly Asp Ile His Val Ser Asp Asn Ile Leu Phe Lys
    1040                1045                1050

Ile Val Gly Cys Asp Asp Glu Thr Tyr Val Gly Ile Arg Tyr Phe
    1055                1060                1065

Lys Val Phe Asn Thr Glu Leu Asp Lys Thr Glu Ile Glu Thr Leu
    1070                1075                1080

Tyr Ser Asn Glu Pro Asp Pro Ser Ile Leu Lys Asp Tyr Trp Gly
    1085                1090                1095

Asn Tyr Leu Leu Tyr Asn Lys Lys Tyr Tyr Leu Phe Asn Leu Leu
    1100                1105                1110

Arg Lys Asp Lys Tyr Ile Thr Arg Asn Ser Gly Ile Leu Asn Ile
    1115                1120                1125

Asn Gln Gln Arg Gly Val Thr Gly Gly Ile Ser Val Phe Leu Asn
    1130                1135                1140

Tyr Lys Leu Tyr Glu Gly Val Glu Val Ile Ile Arg Lys Asn Ala
    1145                1150                1155

Pro Ile Asp Ile Ser Asn Thr Asp Asn Phe Val Arg Lys Asn Asp
    1160                1165                1170

Leu Ala Tyr Ile Asn Val Val Asp His Gly Val Glu Tyr Arg Leu
    1175                1180                1185

Tyr Ala Asp Ile Ser Ile Thr Lys Ser Glu Lys Ile Ile Lys Leu
    1190                1195                1200

Ile Arg Thr Ser Asn Pro Asn Asp Ser Leu Gly Gln Ile Ile Val
    1205                1210                1215

```
Met Asp Ser Ile Gly Asn Asn Cys Thr Met Asn Phe Gln Asn Asn
    1220                1225                1230

Asp Gly Ser Asn Ile Gly Leu Leu Gly Phe His Ser Asp Asp Leu
    1235                1240                1245

Val Ala Ser Ser Trp Tyr Tyr Asn His Ile Arg Arg Asn Thr Ser
    1250                1255                1260

Ser Asn Gly Cys Phe Trp Ser Phe Ile Ser Lys Glu His Gly Trp
    1265                1270                1275

Lys Glu
    1280

<210> SEQ ID NO 13
<211> LENGTH: 3894
<212> TYPE: DNA
<213> ORGANISM: Clostridium botulinum
<220> FEATURE:
<221> NAME/KEY: misc_feature
<222> LOCATION: (20)..(20)
<223> OTHER INFORMATION: n is a, c, g, or t

<400> SEQUENCE: 13
```

| | | | | | |
|---|---|---|---|---|---|
| atgccagtta | atataaaaan | ctttaattat | aatgacccta | ttaataatga | tgacattatt    60 |
| atgatggaac | cattcaatga | cccagggcca | ggaacatatt | ataaagcttt | taggattata   120 |
| gatcgtattt | ggatagtacc | agaaaggttt | acttatggat | tcaacctga | ccaatttaat   180 |
| gccagtacag | gagttttag | taaagatgtc | tacgaatatt | acgatccaac | ttatttaaaa   240 |
| accgatgctg | aaaagataa | attttaaaa | acaatgatta | aattatttaa | tagaattaat   300 |
| tcaaaccat | caggacagag | attactggat | atgatagtag | atgctatacc | ttatcttgga   360 |
| aatgcatcta | caccgcccga | caaatttgca | gcaaatgttg | caaatgtatc | tattaataaa   420 |
| aaaattatcc | aacctggagc | tgaagatcaa | ataaaaggtt | taatgacaaa | tttaataata   480 |
| tttggaccag | gaccagttct | aagtgataat | tttactgata | gtatgattat | gaatggccat   540 |
| tccccaatat | cagaaggatt | tggtgcaaga | atgatgataa | gattttgtcc | tagttgttta   600 |
| aatgtattta | ataatgttca | ggaaaataaa | gatacatcta | tatttagtag | acgcgcgtat   660 |
| tttgcagatc | cagctctaac | gttaatgcat | gaacttatac | atgtgttaca | tggattatat   720 |
| ggaattaaga | taagtaattt | accaattact | ccaaatacaa | aagaattttt | catgcaacat   780 |
| agcgatcctg | tacaagcaga | agaactatat | acattcggag | acatgatcc | tagtgttata   840 |
| agtccttcta | cggatatgaa | tatttataat | aaagcgttac | aaaattttca | agatatagct   900 |
| aataggctta | atattgtttc | aagtgcccaa | gggagtggaa | ttgatatttc | cttatataaa   960 |
| caaatatata | aaaataaata | tgattttgtt | gaagatccta | atggaaaata | tagtgtagat  1020 |
| aaggataagt | ttgataaatt | atataaggcc | ttaatgtttg | gctttactga | aactaatcta  1080 |
| gctggtgaat | atggaataaa | aactaggtat | tcttatttta | gtgaatattt | gccaccgata  1140 |
| aaaactgaaa | aattgttaga | caatacaatt | tatactcaaa | atgaaggctt | taacatagct  1200 |
| agtaaaaatc | tcaaaacgga | atttaatggt | cagaataagg | cggtaaataa | agaggcttat  1260 |
| gaagaaatca | gcctagaaca | tctcgttata | tatagaatag | caatgtgcaa | gcctgtaatg  1320 |
| tacaaaaata | ccggtaaatc | tgaacagtgt | attattgtta | ataatgagga | tttatttttc  1380 |
| atagctaata | agatagtttt | ttcaaaagat | ttagctaaag | cagaaactat | agcatataat  1440 |
| acacaaaata | atactataga | aaataatttt | tctatagatc | agttgatttt | agataatgat  1500 |
| ttaagcagtg | gcatagactt | accaaatgaa | aacacagaac | catttacaaa | ttttgacgac  1560 |

```
atagatatcc ctgtgtatat taaacaatct gctttaaaaa aaattttgt ggatggagat    1620 agcctttttg aatatttaca tgctcaaaca tttccttcta atatagaaaa tctacaacta    1680
acgaattcat taaatgatgc tttaagaaat aataataaag tctatacttt tttttctaca    1740
aaccttgttg aaaaagctaa tacagttgta ggtgcttcac tttttgtaaa ctgggtaaaa    1800
ggagtaatag atgattttac atctgaatcc acacaaaaaa gtactataga taaagtttca    1860
gatgtatcca taattattcc ctatatagga cctgctttga atgtaggaaa tgaaacagct    1920
aaagaaaatt ttaaaaatgc ttttgaaata ggtggagccg ctatcttaat ggagtttatt    1980
ccagaactta ttgtacctat agttggattt tttacattag aatcatatgt aggaaataaa    2040
gggcatatta ttatgacgat atccaatgct ttaaagaaaa gggatcaaaa atggacagat    2100
atgtatggtt tgatagtatc gcagtggctc tcaacggtta atactcaatt ttatacaata    2160
aaagaaagaa tgtacaatgc tttaaataat caatcacaag caatagaaaa aataatagaa    2220
gatcaatata atagatatag tgaagaagat aaaatgaata ttaacattga ttttaatgat    2280
atagatttta aacttaatca aagtataaat ttagcaataa acaatataga tgattttata    2340
aaccaatgtt ctatatcata tctaatgaat agaatgattc cattagctgt aaaaaagtta    2400
aaagactttg atgataatct taagagagat ttattggagt atatagatac aaatgaacta    2460
tatttacttg atgaagtaaa tattctaaaa tcaaaagtaa atagacacct aaaagacagt    2520
ataccatttg atctttcact atataccaag gacacaattt taatacaagt ttttaataat    2580
tatattagta atattagtag taatgctatt ttaagtttaa gttatagagg tgggcgttta    2640
atagattcat ctggatatgg tgcaactatg aatgtaggtt cagatgttat ctttaatgat    2700
ataggaaatg gtcaatttaa attaaataat tctgaaaata gtaatattac ggcacatcaa    2760
agtaaattcg ttgtatatga tagtatgttt gataatttta gcattaactt tgggtaagg    2820 actcctaaat ataataataa tgatatacaa acttatcttc aaaatgagta tacaataatt    2880
agttgtataa aaaatgactc aggatggaaa gtatctatta agggaaatag aataatatgg    2940
acattaatag atgttaatgc aaaatctaaa tcaatatttt tcgaatatag tataaaagat    3000
aatatatcag attatataaa taaatggttt tccataacta ttactaatga tagattaggt    3060
aacgcaaata tttatataaa tggaagtttg aaaaaagtg aaaaattttt aaacttagat    3120
agaattaatt ctagtaatga tatagacttc aaattaatta attgtacaga tactactaaa    3180
tttgtttgga ttaaggattt taatattttt ggtagagaat taaatgctac agaagtatct    3240
tcactatatt ggattcaatc atctacaaat acttttaaaag attttttgggg gaatccttta    3300 agatacgata cacaatacta tctgtttaat caaggtatgc aaaatatcta tataaagtat    3360
tttagtaaag cttctatggg ggaaactgca ccacgtacaa actttaataa tgcagcaata    3420
aattatcaaa atttatatct tggtttacga tttattataa aaaaagcatc aaattctcgg    3480
aatataaata atgataatat agtcagagaa ggagattata tatatcttaa tattgataat    3540
atttctgatg aatcttacag agtatatgtt ttggtgaatt ctaaagaaat tcaaactcaa    3600
ttatttttag cacccataaa tgatgatcct acgttctatg atgtactaca aataaaaaaa    3660
tattatgaaa aaacaacata taattgtcag atactttgcg aaaaagatac taaaacatttt    3720 gggctgtttg gaattggtaa atttgttaaa gattatggat atgtttggga tacctatgat    3780
aattattttt gcataagtca gtggtatctc agaagaatat ctgaaaatat aaataaatta    3840
aggttgggat gtaattggca attcattccc gtggatgaag gatggacaga ataa          3894
```

```
<210> SEQ ID NO 14
<211> LENGTH: 1297
<212> TYPE: PRT
<213> ORGANISM: Clostridium botulinum
<220> FEATURE:
<221> NAME/KEY: misc_feature
<222> LOCATION: (7)..(7)
<223> OTHER INFORMATION: Xaa can be any naturally occurring amino acid

<400> SEQUENCE: 14
```

| Met | Pro | Val | Asn | Ile | Lys | Xaa | Phe | Asn | Tyr | Asn | Asp | Pro | Ile | Asn | Asn |
|---|---|---|---|---|---|---|---|---|---|---|---|---|---|---|---|
| 1 | | | | 5 | | | | | 10 | | | | | 15 | |

| Asp | Asp | Ile | Ile | Met | Met | Glu | Pro | Phe | Asn | Asp | Pro | Gly | Pro | Gly | Thr |
|---|---|---|---|---|---|---|---|---|---|---|---|---|---|---|---|
| | | | 20 | | | | | 25 | | | | | 30 | | |

| Tyr | Tyr | Lys | Ala | Phe | Arg | Ile | Ile | Asp | Arg | Ile | Trp | Ile | Val | Pro | Glu |
|---|---|---|---|---|---|---|---|---|---|---|---|---|---|---|---|
| | | | 35 | | | | | 40 | | | | | 45 | | |

| Arg | Phe | Thr | Tyr | Gly | Phe | Gln | Pro | Asp | Gln | Phe | Asn | Ala | Ser | Thr | Gly |
|---|---|---|---|---|---|---|---|---|---|---|---|---|---|---|---|
| | 50 | | | | | 55 | | | | | 60 | | | | |

| Val | Phe | Ser | Lys | Asp | Val | Tyr | Glu | Tyr | Tyr | Asp | Pro | Thr | Tyr | Leu | Lys |
|---|---|---|---|---|---|---|---|---|---|---|---|---|---|---|---|
| 65 | | | | | 70 | | | | | 75 | | | | | 80 |

| Thr | Asp | Ala | Glu | Lys | Asp | Lys | Phe | Leu | Lys | Thr | Met | Ile | Lys | Leu | Phe |
|---|---|---|---|---|---|---|---|---|---|---|---|---|---|---|---|
| | | | | 85 | | | | | 90 | | | | | 95 | |

| Asn | Arg | Ile | Asn | Ser | Lys | Pro | Ser | Gly | Gln | Arg | Leu | Leu | Asp | Met | Ile |
|---|---|---|---|---|---|---|---|---|---|---|---|---|---|---|---|
| | | | 100 | | | | | 105 | | | | | 110 | | |

| Val | Asp | Ala | Ile | Pro | Tyr | Leu | Gly | Asn | Ala | Ser | Thr | Pro | Pro | Asp | Lys |
|---|---|---|---|---|---|---|---|---|---|---|---|---|---|---|---|
| | | | 115 | | | | | 120 | | | | | 125 | | |

| Phe | Ala | Ala | Asn | Val | Ala | Asn | Val | Ser | Ile | Asn | Lys | Lys | Ile | Ile | Gln |
|---|---|---|---|---|---|---|---|---|---|---|---|---|---|---|---|
| | 130 | | | | | 135 | | | | | 140 | | | | |

| Pro | Gly | Ala | Glu | Asp | Gln | Ile | Lys | Gly | Leu | Met | Thr | Asn | Leu | Ile | Ile |
|---|---|---|---|---|---|---|---|---|---|---|---|---|---|---|---|
| 145 | | | | | 150 | | | | | 155 | | | | | 160 |

| Phe | Gly | Pro | Gly | Pro | Val | Leu | Ser | Asp | Asn | Phe | Thr | Asp | Ser | Met | Ile |
|---|---|---|---|---|---|---|---|---|---|---|---|---|---|---|---|
| | | | | 165 | | | | | 170 | | | | | 175 | |

| Met | Asn | Gly | His | Ser | Pro | Ile | Ser | Glu | Gly | Phe | Gly | Ala | Arg | Met | Met |
|---|---|---|---|---|---|---|---|---|---|---|---|---|---|---|---|
| | | | 180 | | | | | 185 | | | | | 190 | | |

| Ile | Arg | Phe | Cys | Pro | Ser | Cys | Leu | Asn | Val | Phe | Asn | Asn | Val | Gln | Glu |
|---|---|---|---|---|---|---|---|---|---|---|---|---|---|---|---|
| | | | 195 | | | | | 200 | | | | | 205 | | |

| Asn | Lys | Asp | Thr | Ser | Ile | Phe | Ser | Arg | Arg | Ala | Tyr | Phe | Ala | Asp | Pro |
|---|---|---|---|---|---|---|---|---|---|---|---|---|---|---|---|
| | 210 | | | | | 215 | | | | | 220 | | | | |

| Ala | Leu | Thr | Leu | Met | His | Glu | Leu | Ile | His | Val | Leu | His | Gly | Leu | Tyr |
|---|---|---|---|---|---|---|---|---|---|---|---|---|---|---|---|
| 225 | | | | | 230 | | | | | 235 | | | | | 240 |

| Gly | Ile | Lys | Ile | Ser | Asn | Leu | Pro | Ile | Thr | Pro | Asn | Thr | Lys | Glu | Phe |
|---|---|---|---|---|---|---|---|---|---|---|---|---|---|---|---|
| | | | | 245 | | | | | 250 | | | | | 255 | |

| Phe | Met | Gln | His | Ser | Asp | Pro | Val | Gln | Ala | Glu | Leu | Tyr | Thr | Phe |
|---|---|---|---|---|---|---|---|---|---|---|---|---|---|---|
| | | | 260 | | | | | 265 | | | | | 270 | |

| Gly | Gly | His | Asp | Pro | Ser | Val | Ile | Ser | Pro | Ser | Thr | Asp | Met | Asn | Ile |
|---|---|---|---|---|---|---|---|---|---|---|---|---|---|---|---|
| | | | 275 | | | | | 280 | | | | | 285 | | |

| Tyr | Asn | Lys | Ala | Leu | Gln | Asn | Phe | Gln | Asp | Ile | Ala | Asn | Arg | Leu | Asn |
|---|---|---|---|---|---|---|---|---|---|---|---|---|---|---|---|
| | 290 | | | | | 295 | | | | | 300 | | | | |

| Ile | Val | Ser | Ser | Ala | Gln | Gly | Ser | Gly | Ile | Asp | Ile | Ser | Leu | Tyr | Lys |
|---|---|---|---|---|---|---|---|---|---|---|---|---|---|---|---|
| 305 | | | | | 310 | | | | | 315 | | | | | 320 |

| Gln | Ile | Tyr | Lys | Asn | Lys | Tyr | Asp | Phe | Val | Glu | Asp | Pro | Asn | Gly | Lys |
|---|---|---|---|---|---|---|---|---|---|---|---|---|---|---|---|
| | | | | 325 | | | | | 330 | | | | | 335 | |

| Tyr | Ser | Val | Asp | Lys | Asp | Lys | Phe | Asp | Lys | Leu | Tyr | Lys | Ala | Leu | Met |
|---|---|---|---|---|---|---|---|---|---|---|---|---|---|---|---|
| | | | 340 | | | | | 345 | | | | | 350 | | |

| Phe | Gly | Phe | Thr | Glu | Thr | Asn | Leu | Ala | Gly | Glu | Tyr | Gly | Ile | Lys | Thr |
|---|---|---|---|---|---|---|---|---|---|---|---|---|---|---|---|
| | | | 355 | | | | | 360 | | | | | 365 | | |

```
Arg Tyr Ser Tyr Phe Ser Glu Tyr Leu Pro Pro Ile Lys Thr Glu Lys
    370                 375                 380

Leu Leu Asp Asn Thr Ile Tyr Thr Gln Asn Glu Gly Phe Asn Ile Ala
385                 390                 395                 400

Ser Lys Asn Leu Lys Thr Glu Phe Asn Gly Gln Asn Lys Ala Val Asn
                405                 410                 415

Lys Glu Ala Tyr Glu Glu Ile Ser Leu Glu His Leu Val Ile Tyr Arg
                420                 425                 430

Ile Ala Met Cys Lys Pro Val Met Tyr Lys Asn Thr Gly Lys Ser Glu
            435                 440                 445

Gln Cys Ile Ile Val Asn Asn Glu Asp Leu Phe Phe Ile Ala Asn Lys
        450                 455                 460

Asp Ser Phe Ser Lys Asp Leu Ala Lys Ala Glu Thr Ile Ala Tyr Asn
465                 470                 475                 480

Thr Gln Asn Asn Thr Ile Glu Asn Asn Phe Ser Ile Asp Gln Leu Ile
                485                 490                 495

Leu Asp Asn Asp Leu Ser Ser Gly Ile Asp Leu Pro Asn Glu Asn Thr
                500                 505                 510

Glu Pro Phe Thr Asn Phe Asp Asp Ile Asp Ile Pro Val Tyr Ile Lys
            515                 520                 525

Gln Ser Ala Leu Lys Lys Ile Phe Val Asp Gly Asp Ser Leu Phe Glu
        530                 535                 540

Tyr Leu His Ala Gln Thr Phe Pro Ser Asn Ile Glu Asn Leu Gln Leu
545                 550                 555                 560

Thr Asn Ser Leu Asn Asp Ala Leu Arg Asn Asn Asn Lys Val Tyr Thr
                565                 570                 575

Phe Phe Ser Thr Asn Leu Val Glu Lys Ala Asn Thr Val Val Gly Ala
                580                 585                 590

Ser Leu Phe Val Asn Trp Val Lys Gly Val Ile Asp Asp Phe Thr Ser
            595                 600                 605

Glu Ser Thr Gln Lys Ser Thr Ile Asp Lys Val Ser Asp Val Ser Ile
        610                 615                 620

Ile Ile Pro Tyr Ile Gly Pro Ala Leu Asn Val Gly Asn Glu Thr Ala
625                 630                 635                 640

Lys Glu Asn Phe Lys Asn Ala Phe Glu Ile Gly Gly Ala Ala Ile Leu
                645                 650                 655

Met Glu Phe Ile Pro Glu Leu Ile Val Pro Ile Val Gly Phe Phe Thr
            660                 665                 670

Leu Glu Ser Tyr Val Gly Asn Lys Gly His Ile Ile Met Thr Ile Ser
        675                 680                 685

Asn Ala Leu Lys Lys Arg Asp Gln Lys Trp Thr Asp Met Tyr Gly Leu
690                 695                 700

Ile Val Ser Gln Trp Leu Ser Thr Val Asn Thr Gln Phe Tyr Thr Ile
705                 710                 715                 720

Lys Glu Arg Met Tyr Asn Ala Leu Asn Asn Gln Ser Gln Ala Ile Glu
                725                 730                 735

Lys Ile Ile Glu Asp Gln Tyr Asn Arg Tyr Ser Glu Glu Asp Lys Met
                740                 745                 750

Asn Ile Asn Ile Asp Phe Asn Asp Ile Asp Phe Lys Leu Asn Gln Ser
            755                 760                 765

Ile Asn Leu Ala Ile Asn Asn Ile Asp Asp Phe Ile Asn Gln Cys Ser
        770                 775                 780
```

-continued

Ile Ser Tyr Leu Met Asn Arg Met Ile Pro Leu Ala Val Lys Lys Leu
785                 790                 795                 800

Lys Asp Phe Asp Asp Asn Leu Lys Arg Asp Leu Leu Glu Tyr Ile Asp
            805                 810                 815

Thr Asn Glu Leu Tyr Leu Leu Asp Glu Val Asn Ile Leu Lys Ser Lys
        820                 825                 830

Val Asn Arg His Leu Lys Asp Ser Ile Pro Phe Asp Leu Ser Leu Tyr
            835                 840                 845

Thr Lys Asp Thr Ile Leu Ile Gln Val Phe Asn Asn Tyr Ile Ser Asn
        850                 855                 860

Ile Ser Ser Asn Ala Ile Leu Ser Leu Ser Tyr Arg Gly Gly Arg Leu
865                 870                 875                 880

Ile Asp Ser Ser Gly Tyr Gly Ala Thr Met Asn Val Gly Ser Asp Val
            885                 890                 895

Ile Phe Asn Asp Ile Gly Asn Gly Gln Phe Lys Leu Asn Asn Ser Glu
            900                 905                 910

Asn Ser Asn Ile Thr Ala His Gln Ser Lys Phe Val Val Tyr Asp Ser
            915                 920                 925

Met Phe Asp Asn Phe Ser Ile Asn Phe Trp Val Arg Thr Pro Lys Tyr
930                 935                 940

Asn Asn Asn Asp Ile Gln Thr Tyr Leu Gln Asn Glu Tyr Thr Ile Ile
945                 950                 955                 960

Ser Cys Ile Lys Asn Asp Ser Gly Trp Lys Val Ser Ile Lys Gly Asn
            965                 970                 975

Arg Ile Ile Trp Thr Leu Ile Asp Val Asn Ala Lys Ser Lys Ser Ile
            980                 985                 990

Phe Phe Glu Tyr Ser Ile Lys Asp Asn Ile Ser Asp Tyr Ile Asn Lys
            995                 1000                1005

Trp Phe Ser Ile Thr Ile Thr Asn Asp Arg Leu Gly Asn Ala Asn
            1010                1015                1020

Ile Tyr Ile Asn Gly Ser Leu Lys Lys Ser Glu Lys Ile Leu Asn
            1025                1030                1035

Leu Asp Arg Ile Asn Ser Ser Asn Asp Ile Asp Phe Lys Leu Ile
            1040                1045                1050

Asn Cys Thr Asp Thr Thr Lys Phe Val Trp Ile Lys Asp Phe Asn
            1055                1060                1065

Ile Phe Gly Arg Glu Leu Asn Ala Thr Glu Val Ser Ser Leu Tyr
            1070                1075                1080

Trp Ile Gln Ser Ser Thr Asn Thr Leu Lys Asp Phe Trp Gly Asn
            1085                1090                1095

Pro Leu Arg Tyr Asp Thr Gln Tyr Tyr Leu Phe Asn Gln Gly Met
            1100                1105                1110

Gln Asn Ile Tyr Ile Lys Tyr Phe Ser Lys Ala Ser Met Gly Glu
            1115                1120                1125

Thr Ala Pro Arg Thr Asn Phe Asn Asn Ala Ala Ile Asn Tyr Gln
            1130                1135                1140

Asn Leu Tyr Leu Gly Leu Arg Phe Ile Ile Lys Lys Ala Ser Asn
            1145                1150                1155

Ser Arg Asn Ile Asn Asn Asp Asn Ile Val Arg Glu Gly Asp Tyr
            1160                1165                1170

Ile Tyr Leu Asn Ile Asp Asn Ile Ser Asp Glu Ser Tyr Arg Val
            1175                1180                1185

Tyr Val Leu Val Asn Ser Lys Glu Ile Gln Thr Gln Leu Phe Leu

| | | | | | | | | | | |
|---|---|---|---|---|---|---|---|---|---|---|
| Ala | Pro | Ile | Asn | Asp | Asp | Pro | Thr | Phe | Tyr | Asp | Val | Leu | Gln | Ile |
| 1205 | | | | | 1210 | | | | | 1215 |

Ala Pro Ile Asn Asp Asp Pro Thr Phe Tyr Asp Val Leu Gln Ile
 1205                 1210                1215

Lys Lys Tyr Tyr Glu Lys Thr Thr Tyr Asn Cys Gln Ile Leu Cys
 1220                1225                1230

Glu Lys Asp Thr Lys Thr Phe Gly Leu Phe Gly Ile Gly Lys Phe
 1235                1240                1245

Val Lys Asp Tyr Gly Tyr Val Trp Asp Thr Tyr Asp Asn Tyr Phe
 1250                1255                1260

Cys Ile Ser Gln Trp Tyr Leu Arg Arg Ile Ser Glu Asn Ile Asn
 1265                1270                1275

Lys Leu Arg Leu Gly Cys Asn Trp Gln Phe Ile Pro Val Asp Glu
 1280                1285                1290

Gly Trp Thr Glu
 1295

```
<210> SEQ ID NO 15
<211> LENGTH: 4400
<212> TYPE: DNA
<213> ORGANISM: Clostridium tetani

<400> SEQUENCE: 15
tagcattaaa aaaattagaa cctatagtaa ataaattaat taatatatag tttttataat      60
ttaattatga ataatattct taagataaaa agtaaatttt taaaaattta aattttcagt     120
ttacaaaaaa taacctgatt atgttatatg taattgtaaa aaacatataa aaaatcagaa     180
aaatttagga ggtatattat taatggatta aataataatt ttttaattta cttttgatta     240
ataaatatta aatgtttatt ttaattagga gatgatacgt atgccaataa ccataaataa     300
ttttagatat agtgatcctg ttaataatga tacaattatt atgatggagc caccatactg     360
taagggtcta gatatctatt ataaggcttt caaaataaca gatcgtattt ggatagtgcc     420
ggaaaggtat gaatttggga caaaacctga agattttaac ccaccatctt cattaataga     480
aggtgcatct gagtattacg atccaaatta tttaaggact gattctgata agatagatt      540
tttacaaacc atggtaaaac tgtttaacag aattaaaaac aatgtagcag gtgaagcctt     600
attagataag ataataaatg ccataccctta ccttggaaat tcatattcct tactagacaa     660
gtttgataca aactctaatt cagtatcttt taatttatta gaacaagacc ccagtggagc     720
aactacaaaa tcagcaatgc tgacaaattt aataatattt ggacctgggc tgttttaaa      780
taaaaatgag gttagaggta ttgtattgag ggtagataat aaaaattact cccatgtag      840
agatggtttt ggctcaataa tgcaaatggc attttgccca gaatatgtac ctacctttga     900
taatgtaata gaaatatta cgtcactcac tattggcaaa agcaaatatt ttcaagatcc      960
agcattacta ttaatgcacg aacttataca tgtactacat ggtttatacg aatgcaggt     1020
atcaagccat gaaattattc catccaaaca agaaatttat atgcagcata catatccaat    1080
aagtgctgaa gaactattca cttttggcgg acaggatgct aatcttataa gtattgatat    1140
aaaaaacgat ttatatgaaa aaactttaaa tgattataaa gctatagcta acaaacttag    1200
tcaagtcact agctgcaatg atcccaacat tgatattgat agctacaaac aaatatatca    1260
acaaaaatat caattcgata agatagcaa tggacaatat attgtaaatg aggataaatt    1320
tcagatacta tataatagca aatgtatgg ttttacagag attgaattgg gaaaaaaatt    1380
taatataaaa actagacttt cttattttag tatgaatcat gaccctgtaa aaattccaaa    1440
```

```
tttattagat gatacaattt acaatgatac agaaggattt aatatagaaa gcaaagatct   1500
gaaatctgaa tataaaggac aaaatatgag ggtaaataca aatgctttta gaaatgttga   1560
tggatcaggc ctagtttcaa aacttattgg cttatgtaaa aaaattatac caccaacaaa   1620
tataagagaa aatttatata atagaactgc atcattaaca gatttaggag gagaattatg   1680
tataaaaatt aaaaatgaag atttaacttt tatagctgaa aaaaatagct tttcagaaga   1740
accatttcaa gatgaaatag ttagttataa tacaaaaaat aaaccattaa attttaatta   1800
ttcgctagat aaaattattg tagattataa tctacaaagt aaaattacat tacctaatga   1860
taggacaacc ccagttacaa aaggaattcc atatgctcca gaatataaaa gtaatgctgc   1920
aagtacaata gaaatacata atattgatga caatacaata tatcaatatt tgtatgctca   1980
aaaatctcct acaactctac aaagaataac tatgactaat tctgttgatg acgcattaat   2040
aaattccacc aaaatatatt catattttcc atctgtaatc agtaaagtta accaaggtgc   2100
acaaggaatt ttattcttac agtgggtgag agatataatt gatgatttta ccaatgaatc   2160
ttcacaaaaa actactattg ataaaatttc agatgtatcc actattgttc cttatatagg   2220
acccgcatta acattgtaa acaaggcta tgagggaaac tttataggcg ctttagaaac    2280
taccggagtg gtttttattat tagaatatat tccagaaatt actttaccag taattgcagc   2340
tttatctata gcagaaagta gcacacaaaa agaaaagata taaaaacaa tagataactt    2400 tttagaaaaa agatatgaaa aatggattga agtatataaa ctagtaaaag caaatggtt    2460 aggcacagtt aatacgcaat tccaaaaaag aagttatcaa atgtatagat ctttagaata   2520
tcaagtagat gcaataaaaa aataatagaa ctatgaatat aaaatatatt caggacctga   2580
taaggaacaa attgccgacg aaattaataa tctgaaaaac aaacttgaag aaaaggctaa   2640
taaagcaatg ataaacataa atatatttat gagggaaagt tctagatcat ttttagttaa   2700
tcaaatgatt aacgaagcta aaaagcagtt attagagttt gatactcaaa gcaaaaatat   2760
tttaatgcag tatataaaag caaattctaa atttataggt ataactgaac taaaaaaatt   2820
agaatcaaaa ataaacaaag ttttttcaac accaattcca ttttcttatt ctaaaaatct   2880
ggattgttgg gttgataatg aagaagatat agatgttata ttaaaaaaga gtacaatttt   2940
aaatttagat attaataatg atattatatc agatatatct gggtttaatt catctgtaat   3000
aacatatcca gatgctcaat tggtgcccgg aataaatggc aaagcaatac atttagtaaa   3060
caatgaatct tctgaagtta tagtgcataa agctatggat attgaatata atgatatgtt   3120
taataatttt accgttagct tttggttgag ggttcctaaa gtatctgcta gtcatttaga   3180
acaatatggc acaaatgagt attcaataat tagctctatg aaaaaacata gtctatcaat   3240
aggatctggt tggagtgtat cacttaaagg taataactta atatggactt taaaagattc   3300
cgcgggagaa gttagacaaa taacttttag ggatttaccct gataaattta atgcttattt   3360
agcaaataaa tgggttttta taactattac taatgataga ttatcttctg ctaatttgta   3420
tataaatgga gtacttatgg gaagtgcaga aattactggt ttaggagcta ttagagagga   3480
taataatata acattaaaac tagatagatg taataataat aatcaatacg tttctattga   3540
taaatttagg atattttgca aagcattaaa tccaaaagag attgaaaaat tatacacaag   3600
ttatttatct ataacctttt taagagactt ctggggaaac cctttacgat atgatacaga   3660
atattattta ataccagtag cttctagttc taaagatgtt caattgaaaa atataacaga   3720
ttatatgtat ttgacaaatg cgccatcgta tactaacgga aaattgaata tatattatag   3780
aaggttatat aatggactaa aatttattat aaaaagatat acacctaata atgaaataga   3840
```

-continued

```
ttcttttgtt aaatcaggtg attttattaa attatatgta tcatataaca ataatgagca    3900
cattgtaggt tatccgaaag atggaaatgc ctttaataat cttgatagaa ttctaagagt    3960
aggttataat gccccaggta tccctcttta taaaaaaatg gaagcagtaa aattgcgtga    4020
tttaaaaacc tattctgtac aacttaaatt atatgatgat aaaaatgcat ctttaggact    4080
agtaggtacc cataatggtc aaataggcaa cgatccaaat agggatatat taattgcaag    4140
caactggtac tttaatcatt taaaagataa aattttagga tgtgattggt actttgtacc    4200
tacagatgaa ggatggacaa atgattaaac agattgatat gttcatgatt actctatata    4260
aaaaattaaa taatataaca atctagctat attattttg attattttct taatatatac     4320
taataaaata atcaaaatag agcctatctt aaattactga agggctgtgt caaaataaga    4380
ttttgacaca gcctctactt                                                4400
```

<210> SEQ ID NO 16
<211> LENGTH: 1315
<212> TYPE: PRT
<213> ORGANISM: Clostridium tetani

<400> SEQUENCE: 16

```
Met Pro Ile Thr Ile Asn Asn Phe Arg Tyr Ser Asp Pro Val Asn Asn
1               5                   10                  15

Asp Thr Ile Ile Met Met Glu Pro Pro Tyr Cys Lys Gly Leu Asp Ile
            20                  25                  30

Tyr Tyr Lys Ala Phe Lys Ile Thr Asp Arg Ile Trp Ile Val Pro Glu
        35                  40                  45

Arg Tyr Glu Phe Gly Thr Lys Pro Glu Asp Phe Asn Pro Pro Ser Ser
    50                  55                  60

Leu Ile Glu Gly Ala Ser Glu Tyr Tyr Asp Pro Asn Tyr Leu Arg Thr
65                  70                  75                  80

Asp Ser Asp Lys Asp Arg Phe Leu Gln Thr Met Val Lys Leu Phe Asn
                85                  90                  95

Arg Ile Lys Asn Asn Val Ala Gly Glu Ala Leu Leu Asp Lys Ile Ile
            100                 105                 110

Asn Ala Ile Pro Tyr Leu Gly Asn Ser Tyr Ser Leu Leu Asp Lys Phe
        115                 120                 125

Asp Thr Asn Ser Asn Ser Val Ser Phe Asn Leu Leu Glu Gln Asp Pro
    130                 135                 140

Ser Gly Ala Thr Thr Lys Ser Ala Met Leu Thr Asn Leu Ile Ile Phe
145                 150                 155                 160

Gly Pro Gly Pro Val Leu Asn Lys Asn Glu Val Arg Gly Ile Val Leu
                165                 170                 175

Arg Val Asp Asn Lys Asn Tyr Phe Pro Cys Arg Asp Gly Phe Gly Ser
            180                 185                 190

Ile Met Gln Met Ala Phe Cys Pro Glu Tyr Val Pro Thr Phe Asp Asn
        195                 200                 205

Val Ile Glu Asn Ile Thr Ser Leu Thr Ile Gly Lys Ser Lys Tyr Phe
    210                 215                 220

Gln Asp Pro Ala Leu Leu Leu Met His Glu Leu Ile His Val Leu His
225                 230                 235                 240

Gly Leu Tyr Gly Met Gln Val Ser Ser His Glu Ile Ile Pro Ser Lys
                245                 250                 255

Gln Glu Ile Tyr Met Gln His Thr Tyr Pro Ile Ser Ala Glu Glu Leu
            260                 265                 270
```

Phe Thr Phe Gly Gly Gln Asp Ala Asn Leu Ile Ser Ile Asp Ile Lys
            275                 280                 285

Asn Asp Leu Tyr Glu Lys Thr Leu Asn Asp Tyr Lys Ala Ile Ala Asn
    290                 295                 300

Lys Leu Ser Gln Val Thr Ser Cys Asn Asp Pro Asn Ile Asp Ile Asp
305                 310                 315                 320

Ser Tyr Lys Gln Ile Tyr Gln Gln Lys Tyr Gln Phe Asp Lys Asp Ser
                325                 330                 335

Asn Gly Gln Tyr Ile Val Asn Glu Asp Lys Phe Gln Ile Leu Tyr Asn
                340                 345                 350

Ser Ile Met Tyr Gly Phe Thr Glu Ile Glu Leu Gly Lys Lys Phe Asn
                355                 360                 365

Ile Lys Thr Arg Leu Ser Tyr Phe Ser Met Asn His Asp Pro Val Lys
            370                 375                 380

Ile Pro Asn Leu Leu Asp Asp Thr Ile Tyr Asn Asp Thr Glu Gly Phe
385                 390                 395                 400

Asn Ile Glu Ser Lys Asp Leu Lys Ser Glu Tyr Lys Gly Gln Asn Met
                405                 410                 415

Arg Val Asn Thr Asn Ala Phe Arg Asn Val Asp Gly Ser Gly Leu Val
                420                 425                 430

Ser Lys Leu Ile Gly Leu Cys Lys Lys Ile Ile Pro Pro Thr Asn Ile
            435                 440                 445

Arg Glu Asn Leu Tyr Asn Arg Thr Ala Ser Leu Thr Asp Leu Gly Gly
            450                 455                 460

Glu Leu Cys Ile Lys Ile Lys Asn Glu Asp Leu Thr Phe Ile Ala Glu
465                 470                 475                 480

Lys Asn Ser Phe Ser Glu Glu Pro Phe Gln Asp Glu Ile Val Ser Tyr
                485                 490                 495

Asn Thr Lys Asn Lys Pro Leu Asn Phe Asn Tyr Ser Leu Asp Lys Ile
            500                 505                 510

Ile Val Asp Tyr Asn Leu Gln Ser Lys Ile Thr Leu Pro Asn Asp Arg
            515                 520                 525

Thr Thr Pro Val Thr Lys Gly Ile Pro Tyr Ala Pro Glu Tyr Lys Ser
            530                 535                 540

Asn Ala Ala Ser Thr Ile Glu Ile His Asn Ile Asp Asp Asn Thr Ile
545                 550                 555                 560

Tyr Gln Tyr Leu Tyr Ala Gln Lys Ser Pro Thr Thr Leu Gln Arg Ile
                565                 570                 575

Thr Met Thr Asn Ser Val Asp Asp Ala Leu Ile Asn Ser Thr Lys Ile
                580                 585                 590

Tyr Ser Tyr Phe Pro Ser Val Ile Ser Lys Val Asn Gln Gly Ala Gln
                595                 600                 605

Gly Ile Leu Phe Leu Gln Trp Val Arg Asp Ile Asp Asp Phe Thr
            610                 615                 620

Asn Glu Ser Ser Gln Lys Thr Thr Ile Asp Lys Ile Ser Asp Val Ser
625                 630                 635                 640

Thr Ile Val Pro Tyr Ile Gly Pro Ala Leu Asn Ile Val Lys Gln Gly
                645                 650                 655

Tyr Glu Gly Asn Phe Ile Gly Ala Leu Glu Thr Thr Gly Val Val Leu
                660                 665                 670

Leu Leu Glu Tyr Ile Pro Glu Ile Thr Leu Pro Val Ile Ala Ala Leu
            675                 680                 685

-continued

Ser Ile Ala Glu Ser Ser Thr Gln Lys Glu Lys Ile Ile Lys Thr Ile
690                     695                 700

Asp Asn Phe Leu Glu Lys Arg Tyr Glu Lys Trp Ile Glu Val Tyr Lys
705                     710                 715                 720

Leu Val Lys Ala Lys Trp Leu Gly Thr Val Asn Thr Gln Phe Gln Lys
            725                 730                 735

Arg Ser Tyr Gln Met Tyr Arg Ser Leu Glu Tyr Gln Val Asp Ala Ile
        740                 745                 750

Lys Lys Ile Ile Asp Tyr Glu Tyr Lys Ile Tyr Ser Gly Pro Asp Lys
            755                 760                 765

Glu Gln Ile Ala Asp Glu Ile Asn Asn Leu Lys Asn Lys Leu Glu Glu
    770                 775                 780

Lys Ala Asn Lys Ala Met Ile Asn Ile Asn Ile Phe Met Arg Glu Ser
785                 790                 795                 800

Ser Arg Ser Phe Leu Val Asn Gln Met Ile Asn Glu Ala Lys Lys Gln
            805                 810                 815

Leu Leu Glu Phe Asp Thr Gln Ser Lys Asn Ile Leu Met Gln Tyr Ile
            820                 825                 830

Lys Ala Asn Ser Lys Phe Ile Gly Ile Thr Glu Leu Lys Lys Leu Glu
            835                 840                 845

Ser Lys Ile Asn Lys Val Phe Ser Thr Pro Ile Pro Phe Ser Tyr Ser
850                 855                 860

Lys Asn Leu Asp Cys Trp Val Asp Asn Glu Glu Asp Ile Asp Val Ile
865                 870                 875                 880

Leu Lys Lys Ser Thr Ile Leu Asn Leu Asp Ile Asn Asn Asp Ile Ile
                885                 890                 895

Ser Asp Ile Ser Gly Phe Asn Ser Ser Val Ile Thr Tyr Pro Asp Ala
            900                 905                 910

Gln Leu Val Pro Gly Ile Asn Gly Lys Ala Ile His Leu Val Asn Asn
            915                 920                 925

Glu Ser Ser Glu Val Ile Val His Lys Ala Met Asp Ile Glu Tyr Asn
    930                 935                 940

Asp Met Phe Asn Asn Phe Thr Val Ser Phe Trp Leu Arg Val Pro Lys
945                 950                 955                 960

Val Ser Ala Ser His Leu Glu Gln Tyr Gly Thr Asn Glu Tyr Ser Ile
            965                 970                 975

Ile Ser Ser Met Lys Lys His Ser Leu Ser Ile Gly Ser Gly Trp Ser
            980                 985                 990

Val Ser Leu Lys Gly Asn Asn Leu Ile Trp Thr Leu Lys Asp Ser Ala
            995                 1000                1005

Gly Glu Val Arg Gln Ile Thr Phe Arg Asp Leu Pro Asp Lys Phe
    1010                1015                1020

Asn Ala Tyr Leu Ala Asn Lys Trp Val Phe Ile Thr Ile Thr Asn
    1025                1030                1035

Asp Arg Leu Ser Ser Ala Asn Leu Tyr Ile Asn Gly Val Leu Met
    1040                1045                1050

Gly Ser Ala Glu Ile Thr Gly Leu Gly Ala Ile Arg Glu Asp Asn
    1055                1060                1065

Asn Ile Thr Leu Lys Leu Asp Arg Cys Asn Asn Asn Asn Gln Tyr
    1070                1075                1080

Val Ser Ile Asp Lys Phe Arg Ile Phe Cys Lys Ala Leu Asn Pro
    1085                1090                1095

Lys Glu Ile Glu Lys Leu Tyr Thr Ser Tyr Leu Ser Ile Thr Phe

|  | 1100 |  |  |  | 1105 |  |  |  | 1110 |  |  |
|---|---|---|---|---|---|---|---|---|---|---|---|
| Leu | Arg | Asp | Phe | Trp | Gly | Asn | Pro | Leu | Arg | Tyr | Asp | Thr | Glu | Tyr |
| | 1115 | | | | 1120 | | | | 1125 | | |
| Tyr | Leu | Ile | Pro | Val | Ala | Ser | Ser | Ser | Lys | Asp | Val | Gln | Leu | Lys |
| | 1130 | | | | 1135 | | | | 1140 | | |
| Asn | Ile | Thr | Asp | Tyr | Met | Tyr | Leu | Thr | Asn | Ala | Pro | Ser | Tyr | Thr |
| | 1145 | | | | 1150 | | | | 1155 | | |
| Asn | Gly | Lys | Leu | Asn | Ile | Tyr | Tyr | Arg | Arg | Leu | Tyr | Asn | Gly | Leu |
| | 1160 | | | | 1165 | | | | 1170 | | |
| Lys | Phe | Ile | Ile | Lys | Arg | Tyr | Thr | Pro | Asn | Asn | Glu | Ile | Asp | Ser |
| | 1175 | | | | 1180 | | | | 1185 | | |
| Phe | Val | Lys | Ser | Gly | Asp | Phe | Ile | Lys | Leu | Tyr | Val | Ser | Tyr | Asn |
| | 1190 | | | | 1195 | | | | 1200 | | |
| Asn | Asn | Glu | His | Ile | Val | Gly | Tyr | Pro | Lys | Asp | Gly | Asn | Ala | Phe |
| | 1205 | | | | 1210 | | | | 1215 | | |
| Asn | Asn | Leu | Asp | Arg | Ile | Leu | Arg | Val | Gly | Tyr | Asn | Ala | Pro | Gly |
| | 1220 | | | | 1225 | | | | 1230 | | |
| Ile | Pro | Leu | Tyr | Lys | Lys | Met | Glu | Ala | Val | Lys | Leu | Arg | Asp | Leu |
| | 1235 | | | | 1240 | | | | 1245 | | |
| Lys | Thr | Tyr | Ser | Val | Gln | Leu | Lys | Leu | Tyr | Asp | Asp | Lys | Asn | Ala |
| | 1250 | | | | 1255 | | | | 1260 | | |
| Ser | Leu | Gly | Leu | Val | Gly | Thr | His | Asn | Gly | Gln | Ile | Gly | Asn | Asp |
| | 1265 | | | | 1270 | | | | 1275 | | |
| Pro | Asn | Arg | Asp | Ile | Leu | Ile | Ala | Ser | Asn | Trp | Tyr | Phe | Asn | His |
| | 1280 | | | | 1285 | | | | 1290 | | |
| Leu | Lys | Asp | Lys | Ile | Leu | Gly | Cys | Asp | Trp | Tyr | Phe | Val | Pro | Thr |
| | 1295 | | | | 1300 | | | | 1305 | | |
| Asp | Glu | Gly | Trp | Thr | Asn | Asp | | | | | |
| | 1310 | | | | 1315 | | | | | | |